(12) United States Patent
Ono et al.

(10) Patent No.: US 12,000,844 B2
(45) Date of Patent: Jun. 4, 2024

(54) DIAGNOSTIC DRUG AND DIAGNOSTIC METHOD FOR ALZHEIMER'S DISEASE

(71) Applicant: SUMITOMO PHARMA CO., LTD., Osaka (JP)

(72) Inventors: Atsushi Ono, Osaka (JP); Yasuhiro Teranishi, Osaka (JP); Masanori Kusumoto, Osaka (JP); Masakazu Hashimoto, Osaka (JP); Shoji Kashiwabara, Suita (JP); Maki Hashimoto, Suita (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 794 days.

(21) Appl. No.: 17/265,805

(22) PCT Filed: Aug. 6, 2019

(86) PCT No.: PCT/JP2019/030904
§ 371 (c)(1),
(2) Date: Feb. 3, 2021

(87) PCT Pub. No.: WO2020/032027
PCT Pub. Date: Feb. 13, 2020

(65) Prior Publication Data
US 2021/0165002 A1 Jun. 3, 2021

(30) Foreign Application Priority Data
Aug. 7, 2018 (JP) .................. 2018-148924

(51) Int. Cl.
*C07K 16/18* (2006.01)
*G01N 33/15* (2006.01)
*G01N 33/531* (2006.01)
*G01N 33/68* (2006.01)

(52) U.S. Cl.
CPC ......... *G01N 33/6896* (2013.01); *C07K 16/18* (2013.01); *G01N 33/15* (2013.01); *G01N 33/531* (2013.01)

(58) Field of Classification Search
None
See application file for complete search history.

(56) References Cited

U.S. PATENT DOCUMENTS
2013/0280732 A1 10/2013 Hashimoto et al.

FOREIGN PATENT DOCUMENTS
WO WO 2010/048497 A1 4/2010
WO WO 2012/091138 A1 7/2012
WO 2021/157634 A1 8/2021

OTHER PUBLICATIONS

Atlas Antibodies, "Anti-SLC38A10 Product Datasheet," Product No. HPA023161 (Dec. 2012).
(Continued)

*Primary Examiner* — Aurora M Fontainhas
(74) *Attorney, Agent, or Firm* — Leydig, Voit & Mayer, Ltd.

(57) ABSTRACT

The present invention provides a polypeptide consisting of any of the following amino acid sequences and useful for determining Alzheimer's disease:
(1) the amino acid sequence shown in SEQ ID NO: 1; and
(2) an amino acid sequence resulting from substitution, deletion, addition or insertion of one to several amino acids in the amino acid sequence shown in SEQ ID NO: 1.

17 Claims, 9 Drawing Sheets
Specification includes a Sequence Listing.

```
  1 MTAAAASNWG LITNIVNSIV GVSVLTMPFC FKQCGIVLGA LLLVFCSWMT
 51 HQSCMFLVKS ASLSKRRTYA GLAFHAYGKA GKMLVETSMI GLMLGTCIAF
101 YVVIGDLGSN FFARLFGFQV GGTFRMFLLF AVSLCIVLPL SLQRNMMASI
151 QSFSAMALLF YTVFMFVIVL SSLKHGLFSG QWLRRVSYVR WEGVFRCIPI
201 FGMSFACQSQ VLPTYDSLDE PSVKTMSSIF ASSLNVVTTF YVMVGFFGYV
251 SFTEATAGNV LMHFPSNLVT EMLRVGFMMS VAVGFPMMIL PCRQALSTLL
301 CEQQQKDGTF AAGGYMPPLR FKALTLSVVF GTMVGGILIP NVETILGLTG
351 ATMGSLICFI CPALIYKKIH KNALSSQVVL WVGLGVLVVS TVTTLSVSEE
401 VPEDLAEEAP GGRLGEAEGL MKVEAARLSA QDPVVAVAED GREKPKLPKE
451 REELEQAQIK GPVDVPGRED GKEAPEEAQL DRPGQGIAVP VGEAHRHEPP
501 VPHDKVVVDE GQDREVPEEN KPFSRHAGGK APGVQGQMAP PLPDSEREKQ
551 EPEQGEVGKR PGQAQALEEA GDLPEDPQKV PEADGQPAVQ PAKEDLGPGD
601 RGLHPRPQAV LSEQQNGLAV GGGEKAKGGP PPGNAAGDTG QPAEDSDHGG
651 KPPLPAEKPA PGPGLPPEPR EQRDVERAGG NQAASQLEEA GRAEMLDHAV
701 LLQVIKEQQV QQKRLLDQQE KLLAVIEEQH KEIHQQRQED EEDKPRQVEV
751 HQEPGAAVPR GQEAPEGKAR ETVENLPPLP LDPVLRAPGG RPAPSQDLNQ
801 RSLEHSEGPV GRDPAGPPDG GPDTEPRAAQ AKLRDGQKDA APRAAGTVKE
851 LPKGPEQVPV PDPAREAGGP EERLAEEFPG QSQDVTGGSQ DRKKPGKEVA
901 ATGTSILKEA NWLVAGPGAE TGDPRMKPKQ VSRDLGLAAD LPGGAEGAAA
951 QPQAVLRQPE LRVISDGEQG GQQGHRLDHG GHLEMRKARG GDHVPVSHEQ
1001 PRGGEDAAVQ EPRQRPEPEL GLKRAVPGGQ RPDNAKPNRD LKLQAGSDLR
1051 RRRRDLGPHA EGQLAPRDGV HGLNPLPDV QVNDLRGALD AQLRQAAGGA
1101 LQVVHSRQLR QAPGPPEES
```

(56) References Cited

OTHER PUBLICATIONS

Doody et al., "Predicting Progression of Alzheimer's Disease," *Alzheimer's Research & Therapy*, 2: 2 (2010).
Godyń et al., "Therapeutic Strategies for Alzheimer's Disease in Clinical Trials," *Pharmacological Reports*, 68(1): 127-138 (2016).
European Patent Office, Extended European Search Report in European Patent Application No. 19846675.7 (Apr. 5, 2022).
Corder et al., "Density profiles of Alzheimer disease regional brain pathology for the Huddinge brain bank: pattern recognition emulates and expands upon Braak staging," *Experimental Gerontology*, 35: 851-864 (2000).
Hashimoto et al., "A Fragment of S38AA is a Novel Plasma Biomarker of Alzheimer's Disease," *J. Alzheimer Dis.*, 71(4): 1163-1174 (2019).
Hellsten et al., "The neuronal and astrocytic protein SLC38A10 transports glutamine, glutamate, and aspartate, suggesting a role in neurotransmission," *FEBS Open Bio.*, 7(6): 730-746 (2017).
Tripathi et al., "SLC38A10 (SNAT10) is Located in ER and Golgi Compartments and Has a Role in Regulating Nascent Protein Synthesis," *Int. J. Mol. Sci.*, 20(24): 6265 (2019).
Japanese Patent Office, International Search Report in International Patent Application No. PCT/JP2019/030904 (Oct. 29, 2019).

Fig. 1

```
  1  MTAAAASNWG LITNIVNSIV GVSVLTMPFC FKQCGIVLGA LLLVFCSWMT
 51  HQSCMFLVKS ASLSKRRTYA GLAFHAYGKA GKMLVETSMI GLMLGTCIAF
101  YVVIGDLGSN FFARLFGFQV GGTFRMFLLF AVSLCIVLPL SLQRNMMASI
151  QSFSAMALLF YTVFMFVIVL SSLKHGLFSG QWLRRVSYVR WEGVFRCIPI
201  FGMSFACQSQ VLPTYDSLDE PSVKTMSSIF ASSLNVVTTF YVMVGFFGYV
251  SFTEATAGNV LMHFPSNLVT EMLRVGFMMS VAVGFPMMIL PCRQALSTLL
301  CEQQQKDGTF AAGGYMPPLR FKALTLSVVF GTMVGGILIP NVETILGLTG
351  ATMGSLICFI CPALIYKKIH KNALSSQVVL WVGLGVLVVS TVTTLSVSEE
401  VPEDLAEEAP GGRLGEAEGL MKVEAARLSA QDPVVAVAED GREKPKLPKE
451  REELEQAQIK GPVDVPGRED GKEAPEEAQL DRPGQGIAVP VGEAHRHEPP
501  VPHDKVVVDE GQDREVPEEN KPPSRHAGGK APGVQGQMAP PLPDSEREKQ
551  EPEQGEVGKR PGQAQALEEA GDLPEDPQKV PEADGQPAVQ PAKEDLGPGD
601  RGLHPRPQAV LSEQQNGLAV GGGEKAKGGP PPGNAAGDTG QPAEDSDHGG
651  KPPLPAEKPA PGPGLPPEPR EQRDVERAGG NQAASQLEEA GRAEMLDHAV
701  LLQVIKEQQV QQKRLLDQQE KLLAVIEEQH KEIHQQRQED EEDKPRQVEV
751  HQEPGAAVPR GQEAPEGKAR ETVENLPPLP LDPVLRAPGG RPAPSQDLNQ
801  RSLEHSEGPV GRDPAGPPDG GPDTEPRAAQ AKLRDGQKDA APRAAGTVKE
851  LPKGPEQVPV PDPAREAGGP EERLAEEFPG QSQDVTGGSQ DRKKPGKEVA
901  ATGTSILKEA NWLVAGPGAE TGDPRMKPKQ VSRDLGLAAD LPGGAEGAAA
951  QPQAVLRQPE LRVISDGEQG GQQGHRLDHG GHLEMRKARG GDHVPVSHEQ
1001 PRGGEDAAVQ EPRQRPEPEL GLKRAVPGGQ RPDNAKPNRD LKLQAGSDLR
1051 RRRRDLGPHA EGQLAPRDGV IIGLNPLPDV QVNDLRGALD AQLRQAAGGA
1101 LQVVHSRQLR QAPGPPEES
```

Fig. 2

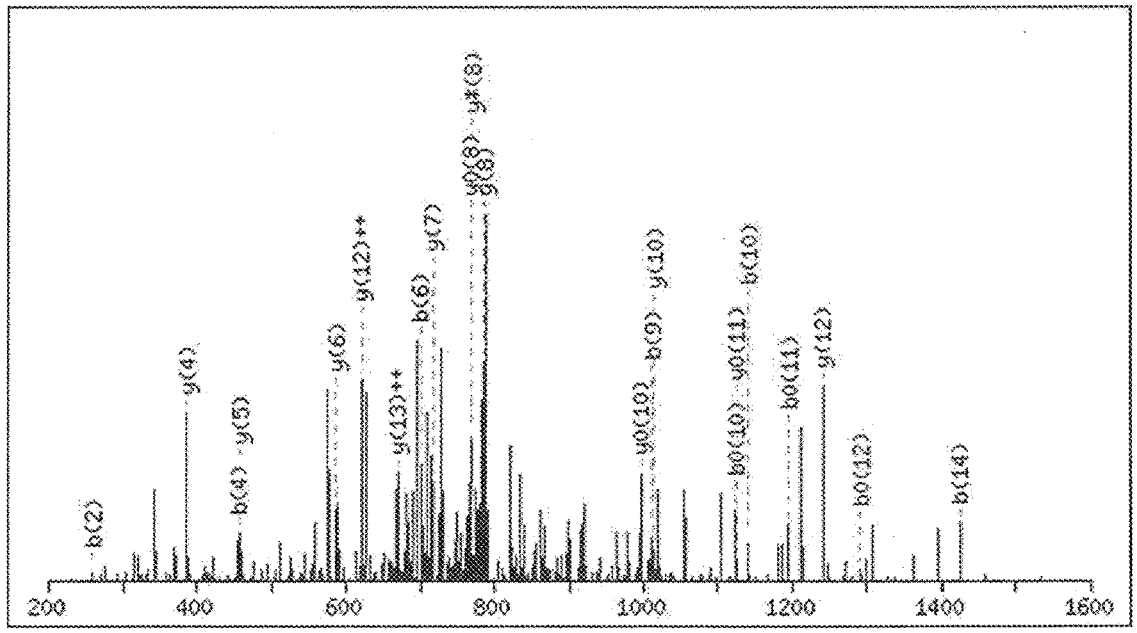

Fig. 3

```
1    MTAAAASNWG LITNIVNSIV GVSVLTMPFC FKQCGIVLGA LLLVFCSWMT
51   HQSCMFLVKS ASLSKRRTYA GLAFHAYGKA GKMLVETSMI GLMLGTCIAF
101  YVVIGDLGSN FFARLFGFQV GGTFRMFLLF AVSLCIVLPL SLQRNMMASI
151  QSFSAMALLF YTVFMFVIVL SSLKHGLFSG QWLRRVSYVR WEGVFRCIPI
201  FGMSFACQSQ VLPTYDSLDE PSVKTMSSIF ASSLNVVTTF YVMVGFFGYV
251  SFTEATAGNV LMHFPSNLVT EMLRVGFMMS VAVGFPMMIL PCRQALSTLL
301  CEQQKDGTF  AAGGYMPPLR FKALTLSVVF GTMVGGILIP NVETILGLTG
351  ATMGSLICFI CPALIYKKIH KNALSSQVVL WVGLGVLVVS TVTTLSVSEE
401  VPEDLAEEAP GGRLGEAEGL MKVEAARLSA QDPVVAVAED GREKPKLPKE
451  REELEQAQIK GPVDVPGRED GKEAPEEAQL DRPGQGIAVP VGEAHRHEPP
501  VPHDKVVVDE GQDREVPEEN KPPSRHAGGK APGVQGQMAP PLPDSEREKQ
551  EPEQGEVGKR PGQAQALEEA GDLPEDPQKV PEADGQPAVQ PAKEDLGPGD
601  RGLHPRPQAV LSEQQNGLAV GGGEKAKGGP PPGNAAGDTG QPAEDSDHGG
651  KPPLPAEKPA PGPGLPPEPR EQRDVERAGG NQAASQLEEA GRAEMLDHAV
701  LLQVIKEQQV QQKRLLDQQE KLLAVIEEQH KEIHQQRQED EEDKPRQVEV
751  HQEPGAAVPR GQEAPEGKAR ETVENLPPLP LDPVLRAPGG RPAPSQDLNQ
801  RSLEHSEGPV GRDPAGPPDG GPDTEPRAAQ AKLRDGQKDA APRAAGTVKE
851  LPKGPEQVPV PDPAREAGGP EERLAEEFPG QSQDVTGGSQ DRKKPGKEVA
901  ATGTSILKEA NWLVAGPGAE TGDPRMKPKQ VSRDLGLAAD LPGGAEGAAA
951  QPQAVLRQPE LRVISDGEQG GQQGHRLDHG GHLEMRKARG GDHVPVSHEQ
1001 PRGGEDAAVQ EPRQRPEPEL GLKRAVPGGQ RPDNAKPNRD LKLQAGSDLR
1051 RRRRDLGPHA EGQLAPRDGV IIGLNPLPDV QVNDLRGALD AQLRQAAGGA
1101 LQVVHSRQLR QAPGPPEES
```

Fig. 4

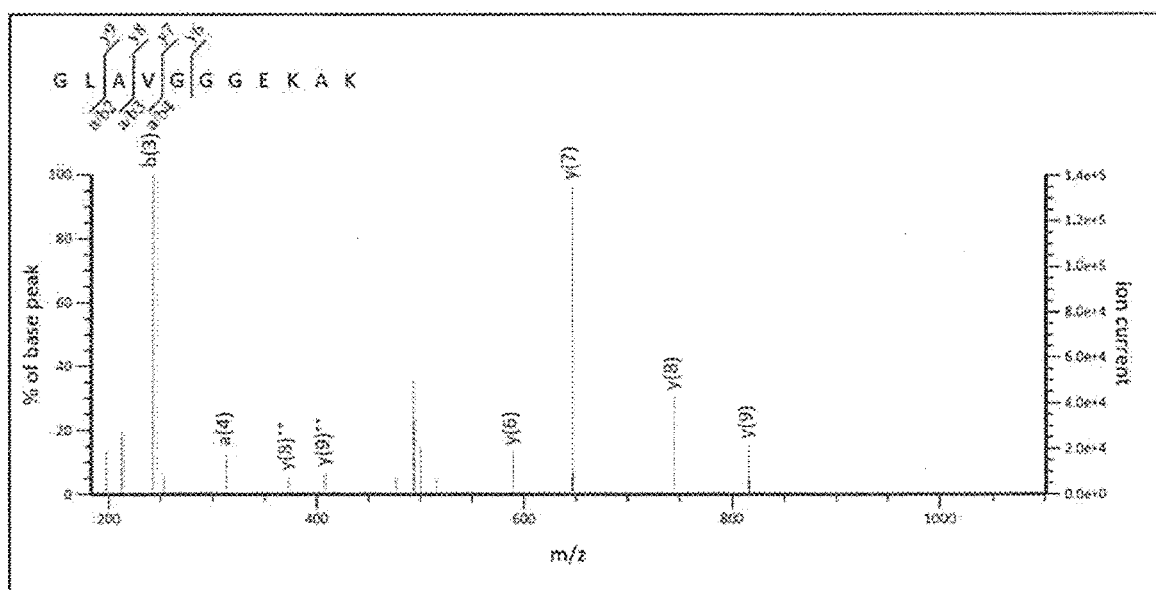

Fig. 5

```
1    MTAAAASNWG  LITNIVNSIV  GVSVLTMPFC  FKQCGIVLGA  LLLVFCSWMT
51   HQSCMFLVKS  ASLSKRRTYA  GLAFHAYGKA  GKMLVETSMI  GLMLGTCIAF
101  YVVIGDLGSN  FFARLFGFQV  GGTFRMFLLF  AVSLCIVLPL  SLQRNMMASI
151  QSFSAMALLF  YTVFMFVIVL  SSLKHGLFSG  QWLRRVSYVR  WEGVFRCIPI
201  FGMSFACQSQ  VLPTYDSLDE  PSVKTMSSIF  ASSLNVVTTF  YVMVGFFGYV
251  SFTEATAGNV  LMHFPSNLVT  EMLRVGFMMS  VAVGFPMMIL  PCRQALSTLL
301  CEQQQKDGTF  AAGGYMPPLR  FKALTLSVVF  GTMVGGILIP  NVETILGLTG
351  ATMGSLICFI  CPALIYKKIH  KNALSSQVVL  WVGLGVLVVS  TVTTLSVSEE
401  VPEDLAEEAP  GGRLGEAEGL  MKVEAARLSA  QDPVVAVAED  GREKPKLPKE
451  REELEQAQIK  GPVDVPGRED  GKEAPEEAQL  DRPGQGIAVP  VGEAHRHEPP
501  VPHDKVVVDE  GQDREVPEEN  KPPSRHAGGK  APGVQGQMAP  PLPDSEREKQ
551  EPEQGEVGKR  PGQAQALEEA  GDLPEDPQKV  PEADGQPAVQ  PAKEDLPGPD
601  RGLHPRPQAV  LSEQQNGLAV  GGGEKAKGGP  PPGNAAGDTG  QPAEDSDHGG
651  KPPLPAEKPA  PGPGLPPEPR  EQRDVERAGG  NQAASQLEEA  GRAEMLDHAV
701  LLQVIKEQQV  QQKRLLDQQE  KLLAVIEEQH  KEIHQQRQED  EEDKPRQVEV
751  HQEPGAAVPR  GQEAPEGKAR  ETVENLPPLP  LDPVLRAPGG  RPAPSQDLNQ
801  RSLEHSEGPV  GRDPAGPPDG  GPDTEPRAAQ  AKLRDGQKDA  APRAAGTVKE
851  LPKGPEQVPV  PDPAREAGGP  EERLAEEFPG  QSQDVTGGSQ  DRKKPGKEVA
901  ATGTSILKEA  NWLVAGPGAE  TGDPRMKPKQ  VSRDLGLAAD  LPGGAEGAAA
951  QPQAVLRQPE  LRVISDGEQG  GQQGHRLDHG  GHLEMRKARG  GDHVPVSHEQ
1001 PRGGEDAAVQ  EPRQRPEPEL  GLKRAVPGGQ  RPDNAKPNRD  LKLQAGSDLR
1051 RRRRDLGPHA  EGQLAPRDGV  IIGLNPLPDV  QVNDLRGALD  AQLRQAAGGA
1101 LQVVHSRQLR  QAPGPPEES
```

Fig. 6

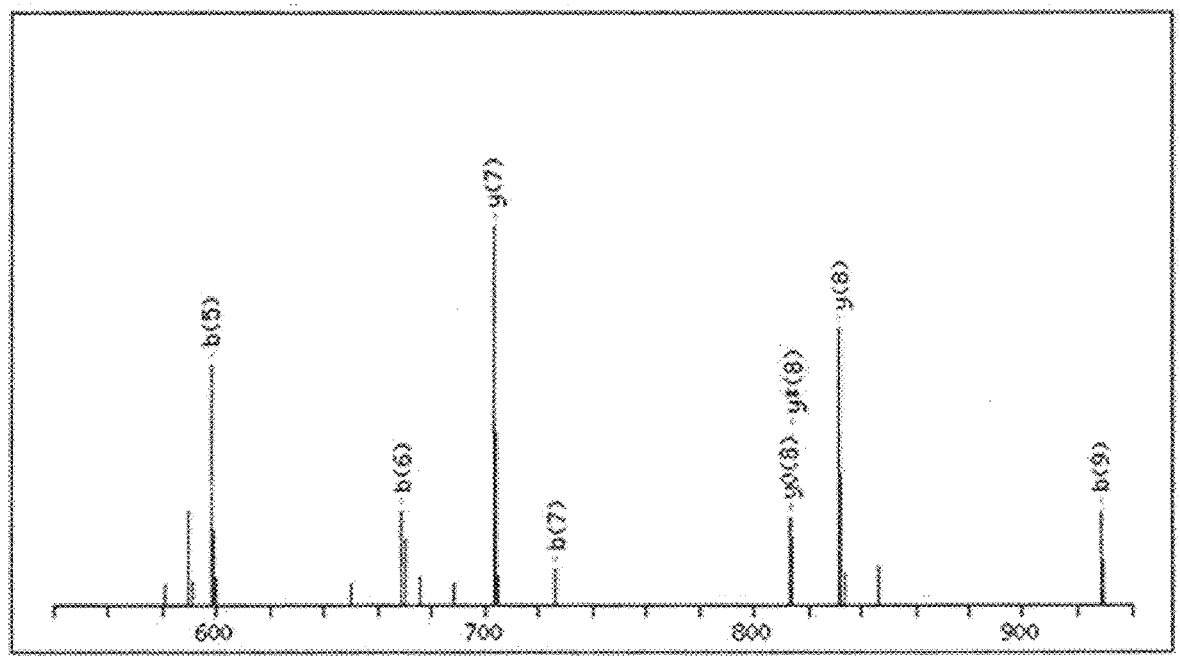

DIAGNOSTIC DRUG AND DIAGNOSTIC METHOD FOR ALZHEIMER'S DISEASE

CROSS-REFERENCE TO RELATED APPLICATIONS

This patent application is the U.S. national phase of International Patent Application No. PCT/JP2019/030904, filed on Aug. 6, 2019, which claims the benefit of Japanese Patent Application No. 2018-148924 filed on Aug. 7, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 54,590 bytes ASCII (Text) file named "752249Sequence-Listing.txt," Feb. 3, 2021.

TECHNICAL FIELD

The present invention relates to an agent for determining Alzheimer's disease, a method for determining Alzheimer's disease, a method for treating Alzheimer's disease, a method for screening for a candidate substance for a therapeutic drug for Alzheimer's disease, a novel anti-S38AA antibody, and the like.

BACKGROUND ART

Alzheimer's disease is a progressive dementia that starts with decrease of short term memory and mild learning disability, develops higher brain dysfunction, particularly visuospatial agnosia, ideational apraxia, constructive apraxia and the like, and finally reaches movement disorder and so-called personality destruction, for which a method of radical treatment has not been found to date. There are predicted to be 2.4 million patients with Alzheimer's disease in the world in 2040, and the importance of a radical treatment method therefor or an early diagnosis thereof is increasing. The progression thereof is different from angiopathic dementia often found in Japan and is considered to continue over several years to ten years or more. In the case of a patient with familial Alzheimer's disease caused by abnormal gene mutation, which is one of the Alzheimer's diseases, the condition of many of the patients rapidly worsens in several years, and the disease is characterized by an early onset since the age at onset is in their 30's-40's. Age, family history, genotype, hypertension, diabetes, smoking and the like are known as the risk factors of Alzheimer's disease other than the gene mutation.

As pathological changes characteristic in Alzheimer's disease, extracellular accumulation of amyloid plaque containing amyloid beta as a main constituent component, and accumulation of highly phosphorylated tau protein in nerve cells are widely known to occur. As for spatial and temporal pathological changes in brain, since accumulation of phosphorylated tau in the pyramidal cells in the hippocampus, particularly the region called CA1, is already observed in patients with early-onset Alzheimer's disease, the pyramidal cells in this region are considered to be spatially and temporally exposed to the strong influence of Alzheimer's disease in early stages, namely show fragility (non-patent document 2). On the other hand, since the movement disorder emerges almost at the final stage of Alzheimer's disease as mentioned above, the purkinje cells in the cerebellum are considered to be most resistant to Alzheimer's disease.

The incidence rate of Alzheimer's disease is considered to rapidly increase after 75 years old, and early detection and early start of the treatment are important for suppressing the pathological progression by a symptomatic drug therapy. Due to the absence of a radical cure for Alzheimer's disease at present, a diagnostic marker for early detection of Alzheimer's disease is energetically searched for, and the measurement of amyloid beta (Aβ40, Aβ42) and phosphorylated tau protein in blood or cerebrospinal fluid is considered to be the most promising. However, it is still difficult to clearly find acquisition of Alzheimer's disease in the future, that is, potential patients with Alzheimer's disease, even when these markers are used alone or in combination (for example, ratio of Aβ40 and Aβ42).

On the other hand, S38AA, particularly an extracellular domain thereof, has been reported as a diagnostic marker for Alzheimer's disease (patent document 1).

However, since early detection and early start of the treatment are important for Alzheimer's disease, a method capable of determining the onset of Alzheimer's disease and people at risk of Alzheimer's disease with higher sensitivity has been demanded.

DOCUMENT LIST

Patent Document patent document 1: WO 2012/091138

Non-Patent Document non-patent document 1: Exp Gerontol. (2000)35:851-64

SUMMARY OF INVENTION

Technical Problem

The present invention aims to provide an agent for determining Alzheimer's disease, a method for determining Alzheimer's disease, a method for treating Alzheimer's disease, a method for screening for a candidate substance for a therapeutic drug for Alzheimer's disease, and the like.

Solution to Problem

S38AA fragment is known to increase in cerebrospinal fluid and plasma of Alzheimer's disease patients (hereinafter sometimes to be referred to as "AD patients"). The present inventors have found two kinds of S38AA fragments (S38AA short fragment (hereinafter sometimes to be abbreviated as "short fragment") and S38AA long fragment (hereinafter sometimes to be abbreviated as "long fragment") having particularly high correlation with Alzheimer's disease. The present inventors have further conducted intensive studies and found that the S38AA short fragments have extremely high reliability as an index for highly accurate determination of the onset of and people at risk of Alzheimer's disease, and the degree of progression of the disease, which resulted in the completion of the present invention.

That is, the present invention relates to the following.

[1] A polypeptide consisting of any of the following amino acid sequences:

(1) the amino acid sequence shown in SEQ ID NO: 1; and
(2) an amino acid sequence resulting from substitution, deletion, addition or insertion of one to several amino acids in the amino acid sequence shown in SEQ ID NO: 1.

[2] An antibody that specifically recognizes the polypeptide of [1].

[3] A nucleic acid encoding the polypeptide of [1].

[4] A kit comprising the antibody of [2].

[5] The kit of [4] further comprising the polypeptide of [1].

[6] A method for detecting the polypeptide of [1], comprising a step of contacting a test sample with the antibody of [2].

[7] The kit of [4] or [5] for use in determining Alzheimer's disease.

[8] An agent for determining Alzheimer's disease, comprising a single or plural kinds of anti-S38AA antibodies capable of measuring the amount of the polypeptide of [1].

[9] The agent of [8], wherein the aforementioned anti-S38AA antibody is the antibody of [2].

[10] Use of the antibody of [2] for the manufacture of an agent for determining Alzheimer's disease.

[11] A method for determining the possibility that a test animal is affected with Alzheimer's disease at present or the animal may be affected with Alzheimer's disease in the future, comprising detecting the polypeptide of [1] in a sample collected from the animal.

[12] The method of [11], comprising the following steps (i) to (iii):
(i) a step of quantifying the polypeptide of [1] in a sample collected from a test animal,
(ii) a step of comparing the amount of the aforementioned polypeptide quantified in (i) with the amount of the aforementioned polypeptide in a sample collected from a healthy animal (hereinafter to be referred to as control value), and
(iii) a step of determining based on the results of (ii) that the aforementioned test animal may be affected with Alzheimer's disease at present or that the animal may be affected with Alzheimer's disease in the future, when the amount of the aforementioned polypeptide quantified in (i) is higher than the control value.

[13] A method for assisting in determining progression of Alzheimer's disease, comprising the following steps (i) to (iii):
(i) a step of quantifying the polypeptide of [1] in a sample collected from a test animal that is or may be affected with Alzheimer's disease,
(ii) a step of comparing the amount of the aforementioned polypeptide quantified in (i) with the amount of the aforementioned polypeptide in a sample collected in the past from the test animal (hereinafter to be referred to as control value), and
(iii) a step of determining based on the results of (ii) that the Alzheimer's disease in the aforementioned test animal is progressing when the amount of the aforementioned polypeptide quantified in (i) is higher than the control value, and the Alzheimer's disease of the aforementioned test animal is improving when the amount is smaller than the control value.

[14] The method of any one of [11] to [13], wherein the test animal is a human.

[15] The method of any one of [11] to [14], wherein the sample is blood, cerebrospinal fluid, saliva, lacrimal fluid or urine.

[16] The method of any one of [11] to [15], further comprising detecting other one or more Alzheimer's disease diagnosis markers.

[17] A method for treating or preventing Alzheimer's disease, comprising the following steps (i)-(iv):
(i) a step of quantifying the polypeptide of [1] in a sample collected from a test animal,
(ii) a step of comparing the amount of the aforementioned polypeptide quantified in (i) with the amount of the aforementioned polypeptide in a sample collected from a healthy animal (hereinafter to be referred to as control value),
(iii) a step of determining based on the results of (ii) that, when the amount of the aforementioned polypeptide quantified in (i) is higher than the control value, the aforementioned test animal is or may be affected with Alzheimer's disease at present, or the animal may be affected with Alzheimer's disease in the future, and
(iv) a step of administering a therapeutic or prophylactic drug for Alzheimer's disease to a test animal determined based on the results of (iii) that it is or may be affected with Alzheimer's disease at present, or may be affected with Alzheimer's disease in the future.

[18] A method for medication for the treatment or prophylaxis of Alzheimer's disease, comprising the following steps (i)-(v)
(i) a step of quantifying the polypeptide of [1] in a sample collected from a test animal that is or may be affected with Alzheimer's disease at present,
(ii) a step of comparing the amount of the aforementioned polypeptide quantified in (i) with the amount of the aforementioned polypeptide in a sample collected in the past from the test animal (hereinafter control value),
(iii) a step of determining based on the results of (ii) that the Alzheimer's disease in the aforementioned test animal is progressing when the amount of the aforementioned polypeptide quantified in (i) is higher than the control value, and the Alzheimer's disease of the aforementioned test animal is improving when the amount is smaller than the control value,
(iv) a step of selecting a therapeutic or prophylactic drug for Alzheimer's disease based on the results of (iii), and
(v) a step of administering the therapeutic drug for Alzheimer's disease selected in (iv) to a test animal.

[19] The method of [17] or [18], wherein the therapeutic drug for Alzheimer's disease is selected from the group consisting of a cholinesterase inhibitor, an NMDA receptor antagonist, an amyloid β remover and accumulation inhibitor, and a tau protein remover and accumulation inhibitor.

[20] The method of [19], wherein the cholinesterase inhibitor is donepezil, galanthamine, rivastigmine, Huperzine A, or tacrine, and the NMDA receptor antagonist is memantine.

[21] A therapeutic drug for Alzheimer's disease for use for a patient whose progression of Alzheimer's disease is determined by the following steps (i)-(iv):
(i) a step of quantifying the polypeptide of [1] in a sample collected from a test animal that is or may be affected with Alzheimer's disease at present,
(ii) a step of comparing the amount of the aforementioned polypeptide quantified in (i) with the amount of the aforementioned polypeptide in a sample collected in the past from the test animal (hereinafter control value),
(iii) a step of determining based on the results of (ii) that the Alzheimer's disease in the aforementioned test animal is progressing when the amount of the aforementioned polypeptide quantified in (i) is higher than the control value, and the Alzheimer's disease of the aforementioned test animal is improving when the amount is smaller than the control value, and
(iv) a step of selecting a therapeutic or prophylactic drug for Alzheimer's disease based on the results of (iii).

[22] A therapeutic or prophylactic drug for Alzheimer's disease, comprising, as an active ingredient, a medicament that decreases the amount of polypeptide of [1] in the body of an Alzheimer's disease patient or a person who may be affected with Alzheimer's disease, or a medicament that inhibits production of the polypeptide in the body of an Alzheimer's disease patient or a person who may be affected with Alzheimer's disease.

[23] A method for screening for a candidate substance for a therapeutic or prophylactic drug for Alzheimer's disease, comprising using, as an index, reduction of the amount of polypeptide of [1] in the body of an Alzheimer's disease patient or a person who may be affected with Alzheimer's disease, or inhibition of production of the polypeptide in the body of an Alzheimer's disease patient or a person who may be affected with Alzheimer's disease.

[24] An antibody that recognizes the polypeptide of SEQ ID NO: 1 or 2, comprising a heavy chain variable region having an amino acid sequence having at least 95% homology with
  SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, and
  a light chain variable region having an amino acid sequence having at least 95% homology with SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

[25] An antibody that recognizes the polypeptide of SEQ ID NO: 1 or 2, comprising
(1) the heavy chain variable region of SEQ ID NO: 4, and the light chain variable region of SEQ ID NO: 5,
(2) the heavy chain variable region of SEQ ID NO: 6, and the light chain variable region of SEQ ID NO: 7,
(3) the heavy chain variable region of SEQ ID NO: 8, and the light chain variable region of SEQ ID NO: 9,
(4) the heavy chain variable region of SEQ ID NO: 10, and the light chain variable region of SEQ ID NO: 11,
(5) the heavy chain variable region of SEQ ID NO: 12, and the light chain variable region of SEQ ID NO: 13,
(6) the heavy chain variable region of SEQ ID NO: 14, and the light chain variable region of SEQ ID NO: 15,
(7) the heavy chain variable region of SEQ ID NO: 16, and the light chain variable region of SEQ ID NO: 17,
(8) the heavy chain variable region of SEQ ID NO: 18, and the light chain variable region of SEQ ID NO: 19,
(9) the heavy chain variable region of SEQ ID NO: 20, and the light chain variable region of SEQ ID NO: 21, or
(10) the heavy chain variable region of SEQ ID NO: 22, and the light chain variable region of SEQ ID NO: 23.

[26] A kit comprising the antibody of [24] or [25].
[27] The kit of [26] further comprising the polypeptide of SEQ ID NO: 1.
[28] A method for detecting the polypeptide of SEQ ID NO: 1, comprising a step of contacting a test sample with the antibody of [24] or [25].
[29] The kit of [26] or [27] for use in determining Alzheimer's disease.
[30] An agent for determining Alzheimer's disease, comprising the antibody of [24] or [25] capable of measuring the amount of the polypeptide of SEQ ID NO: 1.
[31] A method for determining the possibility that a test animal is affected with Alzheimer's disease at present or the animal may be affected with Alzheimer's disease in the future, comprising detecting the polypeptide of SEQ ID NO: 1 in a sample collected from the animal by using the antibody of [24] or [25].
[32] The method of [31], comprising the following steps (i) to (iii):
(i) a step of quantifying the polypeptide of SEQ ID NO: 1 in a sample collected from a test animal by using the antibody of [24] or [25],
(ii) a step of comparing the amount of the aforementioned polypeptide quantified in (i) with the amount of the aforementioned polypeptide in a sample collected from a healthy animal (hereinafter to be referred to as control value), and
(iii) a step of determining based on the results of (ii) that the aforementioned test animal may be affected with Alzheimer's disease at present or that the animal may be affected with Alzheimer's disease in the future, when the amount of the aforementioned polypeptide quantified in (i) is higher than the control value.

[33] A method for determining progression of Alzheimer's disease, comprising the following steps (i) to (iii):
(i) a step of quantifying the polypeptide of claim 1 in a sample collected from a test animal that is or may be affected with Alzheimer's disease by using the antibody of [24] or [25],
(ii) a step of comparing the amount of the aforementioned polypeptide quantified in (i) with the amount of the aforementioned polypeptide in a sample collected in the past from the test animal (hereinafter to be referred to as control value), and
(iii) a step of determining based on the results of (ii) that the Alzheimer's disease in the aforementioned test animal is progressing when the amount of the aforementioned polypeptide quantified in (i) is higher than the control value, and the Alzheimer's disease of the aforementioned test animal is improving when the amount is smaller than the control value.

[34] The method of any one of [31] to [33], wherein the test animal is a human.
[35] The method of any one of [31] to [34], wherein the sample is blood, cerebrospinal fluid, saliva, lacrimal fluid or urine.
[36] The method of any one of [31] to [35], further comprising detecting other one or more Alzheimer's disease diagnosis markers.
[37] A method for treating Alzheimer's disease comprising administering a therapeutic drug for Alzheimer's disease to a patient with determined progression of Alzheimer's disease, comprising the following steps (i)-(iv): (i) a step of quantifying the polypeptide of SEQ ID NO: 1 in a sample collected from a test animal that is or may be affected with Alzheimer's disease by using the antibody of any of [24] and [25],
(ii) a step of comparing the amount of the aforementioned polypeptide quantified in (i) with the amount of the aforementioned polypeptide in a sample collected in the past from the test animal (hereinafter to be referred to as control value), and (iii) a step of determining based on the results of (ii) that the Alzheimer's disease in the aforementioned test animal is progressing when the amount of the aforementioned polypeptide quantified in (i) is higher than the control value, and the Alzheimer's disease of the aforementioned test animal is improving when the amount is smaller than the control value, and (iv) a step of administering a therapeutic drug for Alzheimer's disease to a test animal in need thereof based on the results of (iii).

[38] A method for treating or preventing Alzheimer's disease, comprising, as an active ingredient, a medicament that decreases the amount of polypeptide of SEQ ID NO: 1 in the body of an Alzheimer's disease patient or a person who may be affected with Alzheimer's disease diagnosed using the antibody of any of [24] and [25], or a medicament that inhibits production of the polypeptide in the body of the aforementioned Alzheimer's disease patient or the aforementioned person who may be affected with Alzheimer's disease.

[39] A method for screening for a candidate substance for a therapeutic or prophylactic drug for Alzheimer's disease by using the antibody of any of [24] and [25], comprising using, as an index, reduction of the amount of polypeptide of SEQ ID NO: 1 in the body of an Alzheimer's disease patient or a person who may be affected with Alzheimer's disease, or inhibition of production of the polypeptide in the body of an Alzheimer's disease patient or a person who may be affected with Alzheimer's disease.

[item 1] A polypeptide consisting of any of the following amino acid sequences:

(1) the amino acid sequence shown in SEQ ID NO: 1; and (2) an amino acid sequence resulting from substitution, deletion, addition or insertion of one to several amino acids in the amino acid sequence shown in SEQ ID NO: 1.

[item 2] The polypeptide of item 1, consisting of the amino acid sequence shown in SEQ ID NO: 1.

[item 3] A nucleic acid encoding the polypeptide of item 1 or 2.

[item 4] An antibody recognizing the polypeptide of item 1 or 2.

[item 5] The antibody of item 4, further recognizing the polypeptide of SEQ ID NO: 2.

[item 6] The antibody of item 4 or 5, comprising a heavy chain variable region having an amino acid sequence having at least 95% homology with SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, and a light chain variable region having an amino acid sequence having at least 95% homology with SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

[item 7] The antibody of any one of items 4 to 6, comprising a heavy chain variable region having an amino acid sequence having at least 99% homology with SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, and a light chain variable region having an amino acid sequence having at least 99% homology with SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

[item 8] The antibody of any one of items 4 to 6, wherein the amino acid sequence of the heavy chain variable region is SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, and the amino acid sequence of the light chain variable region is SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

[item 9] The antibody of any one of items 4-8, wherein the antibody is (1) an antibody comprising the heavy chain variable region of SEQ ID NO: 4, and the light chain variable region of SEQ ID NO: 5, (2) an antibody comprising the heavy chain variable region of SEQ ID NO: 6, and the light chain variable region of SEQ ID NO: 7, (3) an antibody comprising the heavy chain variable region of SEQ ID NO: 8, and the light chain variable region of SEQ ID NO: 9, (4) an antibody comprising the heavy chain variable region of SEQ ID NO: 10, and the light chain variable region of SEQ ID NO: 11, (5) an antibody comprising the heavy chain variable region of SEQ ID NO: 12, and the light chain variable region of SEQ ID NO: 13, (6) an antibody comprising the heavy chain variable region of SEQ ID NO: 14, and the light chain variable region of SEQ ID NO: 15, (7) an antibody comprising the heavy chain variable region of SEQ ID NO: 16, and the light chain variable region of SEQ ID NO: 17, (8) an antibody comprising the heavy chain variable region of SEQ ID NO: 18, and the light chain variable region of SEQ ID NO: 19, (9) an antibody comprising the heavy chain variable region of SEQ ID NO: 20, and the light chain variable region of SEQ ID NO: 21, or

(10) an antibody comprising the heavy chain variable region of SEQ ID NO: 22, and the light chain variable region of SEQ ID NO: 23.

[item 10] A method for detecting the polypeptide of item 1 or 2, comprising a step of contacting a test sample with the antibody of any one of items 4-9.

[item 11] A kit comprising the antibody of any one of items 4-9.

[item 12] The kit of item 11, further comprising the polypeptide of item 1 or 2.

[item 13] The kit of item 11 or 12 for use in determining Alzheimer's disease.

[item 14] An agent for determining Alzheimer's disease, comprising a single or plural kinds of anti-S38AA antibodies capable of measuring the amount of the polypeptide of item 1 or 2.

[item 15] The agent of item 14, wherein the aforementioned anti-S38AA antibody is the antibody of any one of items 4-9.

[item 16] Use of the antibody of any one of items 4-9 for the manufacture of an agent for determining Alzheimer's disease.

[item 17] A method for determining the possibility that a test animal is affected with Alzheimer's disease at present or the animal may be affected with Alzheimer's disease in the future, comprising detecting the polypeptide of item 1 or 2 in a sample collected from the animal.

[item 18] The method of item 17, wherein the aforementioned polypeptide of item 1 or 2 is detected using the antibody of any one of items 4-9.

[item 19] The method of item 17 or 18, comprising the following steps (i) to (iii):
(i) a step of quantifying the polypeptide of [1] in a sample collected from a test animal,
(ii) a step of comparing the amount of the aforementioned polypeptide quantified in (i) with the amount of the aforementioned polypeptide in a sample collected from a healthy animal (hereinafter to be referred to as control value), and
(iii) a step of determining that the aforementioned test animal may be affected with Alzheimer's disease at present or that the animal may be affected with Alzheimer's disease in the future, when the amount of the aforementioned polypeptide quantified in (i) is higher than the control value based on the results of (ii).

[item 20] The method of item 19, wherein the aforementioned amount of the aforementioned polypeptide quantified in (i) is not less than 1.1 times of the control value.

[item 21] The method of item 17 or 18, comprising the following steps (i) to (iii):
(i) a step of quantifying the polypeptide of item 1 or 2 in a sample collected from a test animal, and
(ii) a step of determining that the aforementioned test animal may be affected with Alzheimer's disease at present or that the animal may be affected with Alzheimer's disease in the future, when the amount of the aforementioned polypeptide quantified in (i) is higher than the cutoff value.

[item 22] The method of item 21, wherein the aforementioned cutoff value is 45-75 units.

[item 23] The method of item 21, wherein the aforementioned cutoff value is 45-75 ng/mL.

[item 24] The method of any one of items 17-23, wherein the aforementioned test animal is a human.

[item 25] The method of any one of items 17-24, wherein the aforementioned sample is blood, cerebrospinal fluid, saliva, lacrimal fluid or urine.

[item 26] The method of any one of items 17-25, further comprising detecting other one or more Alzheimer's disease diagnosis markers.

[item 27] A method for determining progression of Alzheimer's disease, comprising detecting the polypeptide of item 1 or 2 in a sample collected from a test animal.

[item 28] The method of item 27, wherein the aforementioned polypeptide of item 1 or 2 is detected using the antibody of any one of items 4-9.

[item 29] The method of item 27 or 28, comprising the following steps (i) to (iii):
(i) a step of quantifying the polypeptide of item 1 or 2 in a sample collected from a test animal,
(ii) a step of comparing the amount of the aforementioned polypeptide quantified in (i) with the amount of the aforementioned polypeptide in a sample collected from a healthy animal (hereinafter to be referred to as control value), and
(iii) a step of determining based on the results of (ii) that the aforementioned test animal may be affected with Alzheimer's disease at present or that the animal may be affected with Alzheimer's disease in the future, when the amount of the aforementioned polypeptide quantified in (i) is higher than the control value.

[item 30] The method of item 29, wherein the aforementioned amount of the aforementioned polypeptide quantified in the (i) is not less than 1.1 times the control value.

[item 31] The method of item 27 or 28, comprising the following steps (i) to (ii):
(i) a step of quantifying the polypeptide of item 1 or 2 in a sample collected from a test animal, and
(ii) a step of determining that the aforementioned test animal may be affected with Alzheimer's disease at present or that the animal may be affected with Alzheimer's disease in the future, when the amount of the aforementioned polypeptide quantified in (i) is higher than the cutoff value.

[item 32] The method of item 31, wherein the aforementioned cutoff value is 45-75 units.

[item 33] The method of item 31, wherein the aforementioned cutoff value is 45-75 ng/mL.

[item 34] The method of any one of items 27-34, wherein the aforementioned test animal is a human.

[item 35] The method of any one of items 27-34, wherein the aforementioned sample is blood, cerebrospinal fluid, saliva, lacrimal fluid or urine.

[item 36] The method of any one of items 27-35, further comprising detecting other one or more Alzheimer's disease diagnosis markers.

[item 37] A method for treating or preventing Alzheimer's disease, comprising detecting the polypeptide of item 1 or 2 in a sample collected from a test animal and administering a therapeutic drug for Alzheimer's disease to the test animal.

[item 38] The method of item 37, wherein the aforementioned polypeptide of item 1 or 2 is detected using the antibody of any one of items 4-9.

[item 39] The method of item 37 or 38, comprising the following steps (i)-(iv):
(i) a step of quantifying the polypeptide of item 1 or 2 in a sample collected from a test animal,
(ii) a step of comparing the amount of the aforementioned polypeptide quantified in (i) with the amount of the aforementioned polypeptide in a sample collected from a healthy animal (hereinafter to be referred to as control value),
(iii) a step of determining based on the results of (ii) that, when the amount of the aforementioned polypeptide quantified in (i) is higher than the control value, the aforementioned test animal is or may be affected with Alzheimer's disease at present, or the animal may be affected with Alzheimer's disease in the future, and
(iv) a step of administering a therapeutic or prophylactic drug for Alzheimer's disease to the test animal determined based on the results of (iii) that it is or may be affected with Alzheimer's disease at present, or may be affected with Alzheimer's disease in the future.

[item 40] The method of item 39, wherein the aforementioned amount of the aforementioned polypeptide quantified in the (i) is not less than 1.1 times the control value.

[item 41] The method of item 37 or 38, comprising the following steps (i) to (ii):
(i) a step of quantifying the polypeptide of item 1 or 2 in a sample collected from a test animal, and
(ii) a step of determining that the aforementioned test animal may be affected with Alzheimer's disease at present or that the animal may be affected with Alzheimer's disease in the future, when the amount of the aforementioned polypeptide quantified in (i) is higher than the cutoff value.

[item 42] The method of item 41, wherein the aforementioned cutoff value is 45-75 units.

[item 43] The method of item 41, wherein the aforementioned cutoff value is 45-75 ng/mL.

[item 44] The method of any one of items 37-43, wherein the aforementioned test animal is a human.

[item 45] The method of any one of items 37-44, wherein the aforementioned sample is blood, cerebrospinal fluid, saliva, lacrimal fluid or urine.

[item 46] The method of any one of items 37-45, further comprising detecting other one or more Alzheimer's disease diagnosis markers.

[item 47] The method of any one of items 37-46, wherein the therapeutic drug for Alzheimer's disease is at least one selected from the group consisting of cholinesterase inhibitor, NMDA receptor antagonist, amyloid β remover and production inhibitor, and tau protein remover and production inhibitor.

[item 48] The method of item 47, wherein the aforementioned cholinesterase inhibitor is at least one selected from the group consisting of donepezil, galanthamine, rivastigmine, Huperzine A, and tacrine.

[item 49] The method of item 47, wherein the aforementioned NMDA receptor antagonist is memantine.

[item 50] The method of item 47, wherein the aforementioned amyloid β remover and production inhibitor are at least one selected from the group consisting of amyloid β vaccine, amyloid β removing antibody, amyloid β production enzyme inhibitor, amyloid β coagulation inhibitor and amyloid β decomposition promoter.

[item 51] The method of item 47, wherein the aforementioned amyloid β remover and production inhibitor are at least one selected from the group consisting of CNP-520, E-2609, aducanumab, solanezumab, gantenerumab, crenezumab, amilomotide, ASD-005, HSH-971, ELND-005, ALZT-OP1, nilvadipine, ACI-24, UB-311, AFFITOPE AD-02, LY-3002813, BAN-2401, Neurostem-AD, CT-1812, ID-1201, NIC5-15, BI-425809, Posiphen, PQ-912, bryostatin-1, Apabetalone, PBT-2, RIV-1061-IR, MEDI-1814, PF-05236812, SAR-228810, Lu-AF20513, PRI-002, IRX-4204, GC-021109, AAD-2004, CTS-21166, LY-3323795, benfotiamine, bisnorcymserine, MDR-1339, KHK-6640, and NPT-088.

[item 52] The method of item 47, wherein the aforementioned tau protein remover and production inhibitor are at least one selected from the group consisting of tau protein vaccine, tau protein removing antibody, tau protein modifying inhibitor, tau protein coagulation inhibitor, and tau proteolysis promoter.

[item 53] The method of item 47, wherein the aforementioned tau protein remover and production inhibitor are at least one selected from the group consisting of TRx-237, TPI-287, ABBV-8E12, RG-6100, AADvac1, RO7105705, PTI-80, JNJ-63733657, UCB-0107, BIIB-076, MC-1, ACI-35, and AZP-2006.

[item 54] A method for medication for the treatment or prophylaxis of Alzheimer's disease, comprising quantifying the polypeptide of item 1 or 2 in a sample collected from a test animal, selecting a therapeutic or prophylactic drug for Alzheimer's disease, and administering the therapeutic drug for Alzheimer's disease to the test animal.

[item 55] The method of item 54, wherein the aforementioned polypeptide of item 1 or 2 is quantified using the antibody of any one of items 4-9.

[item 56] The method for item 54 or 55, comprising the following steps (i)-(v):
(i) a step of quantifying the polypeptide of [1] in a sample collected from a test animal that is or may be affected with Alzheimer's disease at present,
(ii) a step of comparing the amount of the aforementioned polypeptide quantified in (i) with the amount of the aforementioned polypeptide in a sample collected in the past from the test animal (hereinafter control value),
(iii) a step of determining based on the results of (ii) that the Alzheimer's disease in the aforementioned test animal is progressing when the amount of the aforementioned polypeptide quantified in (i) is higher than the control value, and the Alzheimer's disease of the aforementioned test animal is improving when the amount is smaller than the control value,
(iv) a step of selecting a therapeutic or prophylactic drug for Alzheimer's disease based on the results of (iii), and
(v) a step of administering the therapeutic drug for Alzheimer's disease selected in (iv) to the test animal.

[item 57] The method of item 56, wherein the Alzheimer's disease in the aforementioned test animal is determined to be progressing when the aforementioned amount of the aforementioned polypeptide quantified in (i) is not less than 1.1 times the control value.

[item 58] The method of item 56, wherein the Alzheimer's disease in the aforementioned test animal is determined to be improving when the aforementioned amount of the aforementioned polypeptide quantified in (i) is not more than 0.9 times the control value.

[item 59] The method of any one of items 54-58, wherein the aforementioned test animal is a human.

[item 60] The method of any one of items 54-59, wherein the aforementioned sample is blood, cerebrospinal fluid, saliva, lacrimal fluid or urine.

[item 61] The method of any one of [54] to [60], further comprising detecting one or more other diagnostic markers for Alzheimer's disease.

[item 62] The method of any one of item 54-61, wherein the therapeutic drug for Alzheimer's disease is selected from the group consisting of cholinesterase inhibitor, NMDA receptor antagonist, amyloid β remover and production inhibitor, and tau protein remover and production inhibitor.

[item 63] The method of item 62, wherein the aforementioned cholinesterase inhibitor is at least one selected from the group consisting of donepezil, galanthamine, rivastigmine, Huperzine A, and tacrine.

[item 64] The method of item 62, wherein the aforementioned NMDA receptor antagonist is memantine.

[item 65] The method of item 62, wherein the aforementioned amyloid β remover and production inhibitor are at least one selected from the group consisting of amyloid β vaccine, amyloid β removing antibody, amyloid β production enzyme inhibitor, amyloid β coagulation inhibitor and amyloid β decomposition promoter.

[item 66] The method of item 62, wherein the aforementioned amyloid β remover and production inhibitor are at least one selected from the group consisting of CNP-520, E-2609, aducanumab, solanezumab, gantenerumab, crenezumab, amilomotide, ASD-005, HSH-971, ELND-005, ALZT-OP1, nilvadipine, ACI-24, UB-311, AFFITOPE AD-02, LY-3002813, BAN-2401, Neurostem-AD, CT-1812, ID-1201, NIC5-15, BI-425809, Posiphen, PQ-912, bryostatin-1, Apabetalone, PBT-2, RIV-1061-IR, MEDI-1814, PF-05236812, SAR-228810, Lu-AF20513, PRI-002, IRX-4204, GC-021109, AAD-2004, CTS-21166, LY-3323795, benfotiamine, bisnorcymserine, MDR-1339, KHK-6640, and NPT-088.

[item 67] The method of item 62, wherein the aforementioned tau protein remover and production inhibitor are at least one selected from the group consisting of tau protein vaccine, tau protein removing antibody, tau protein modifying inhibitor, tau protein coagulation inhibitor, and tau proteolysis promoter.

[item 68] The method of item 62, wherein the aforementioned tau protein remover and production inhibitor are at least one selected from the group consisting of TRx-237, TPI-287, ABBV-8E12, RG-6100, AADvac1, RO7105705, PTI-80, JNJ-63733657, UCB-0107, BIIB-076, MC-1, ACI-35, and AZP-2006.

[item 69] A therapeutic drug for Alzheimer's disease for use for a patient with determined progression of Alzheimer's disease by quantifying the polypeptide of item 1 or 2 in a sample collected from a test animal.

[item 70] The drug of item 69, wherein the aforementioned polypeptide of item 1 or 2 is quantified using the antibody of any one of items 4-9.

[item 71] The drug of item 69 or item 70 for use for a patient whose progression of Alzheimer's disease is determined by the following steps (i)-(iv):
(i) a step of quantifying the polypeptide of item 1 or 2 in a sample collected from a test animal that is or may be affected with Alzheimer's disease,
(ii) a step of comparing the amount of the aforementioned polypeptide quantified in (i) with the amount of the aforementioned polypeptide in a sample collected in the past from the test animal (hereinafter to be referred to as control value),
(iii) a step of determining based on the results of (ii) that the Alzheimer's disease in the aforementioned test animal is progressing when the amount of the aforementioned polypeptide quantified in (i) is higher than the control value, and the Alzheimer's disease of the aforementioned test animal is improving when the amount is smaller than the control value, and
(iv) a step of determining administration of a therapeutic drug for Alzheimer's disease based on the results of (iii).

[item 72] The drug of item 71, wherein the Alzheimer's disease in the aforementioned test animal is determined to be progressing when the aforementioned amount of the aforementioned polypeptide quantified in (i) is not less than 1.1 times the control value.

[item 73] The drug of item 71, wherein the Alzheimer's disease in the aforementioned test animal is determined to be improving when the aforementioned amount of the aforementioned polypeptide quantified in (i) is not more than 0.9 times the control value.

[item 74] The drug of item 69 or item 70 for use for a patient determined to be possibly affected with Alzheimer's disease at present or possibly affected with Alzheimer's disease in the future by the following steps (i)-(iv):
(i) a step of quantifying the polypeptide of item 1 or 2 in a sample collected from a test animal that is or may be affected with Alzheimer's disease, and
(ii) a step of determining that the aforementioned test animal may be affected with Alzheimer's disease at present or that the animal may be affected with Alzheimer's disease in the future, when the amount of the aforementioned polypeptide quantified in (i) is higher than the cutoff value, and
(iii) a step of determining administration of a therapeutic drug for Alzheimer's disease based on the results of (ii).

[item 75] The drug of item 74, wherein the aforementioned cutoff value is 45-75 units.

[item 76] The drug of item 74, wherein the aforementioned cutoff value is 45-75 ng/mL.

[item 77] The drug of any one of items 69-76, wherein the aforementioned test animal is a human.

[item 78] The drug of any one of items 69-77, wherein the aforementioned sample is blood, cerebrospinal fluid, saliva, lacrimal fluid or urine.

[item 79] The drug of any one of items 69-78, further comprising detecting other one or more Alzheimer's disease diagnosis markers.

[item 80] The drug of any one of items 69-79, wherein the therapeutic drug for Alzheimer's disease is selected from the group consisting of cholinesterase inhibitor, NMDA receptor antagonist, amyloid β remover and production inhibitor, and tau protein remover and production inhibitor described in a for Alzheimer's disease.

[item 81] The drug of item 80, wherein the aforementioned cholinesterase inhibitor is at least one selected from the group consisting of donepezil, galanthamine, rivastigmine, Huperzine A, and tacrine.

[item 82] The drug of item 80, wherein the aforementioned NMDA receptor antagonist is memantine.

[item 83] The drug of item 80, wherein the aforementioned amyloid β remover and production inhibitor are at least one selected from the group consisting of amyloid β vaccine, amyloid β removing antibody, amyloid β production enzyme inhibitor, amyloid β coagulation inhibitor and amyloid β decomposition promoter.

[item 84] The drug of item 80, wherein the aforementioned amyloid β remover and production inhibitor are at least one selected from the group consisting of CNP-520, E-2609, aducanumab, solanezumab, gantenerumab, crenezumab, amilomotide, ASD-005, HSH-971, ELND-005, ALZT-OP1, nilvadipine, ACI-24, UB-311, AFFITOPE AD-02, LY-3002813, BAN-2401, Neurostem-AD, CT-1812, ID-1201, NIC5-15, BI-425809, Posiphen, PQ-912, bryostatin-1, Apabetalone, PBT-2, RIV-1061-IR, MEDI-1814, PF-05236812, SAR-228810, Lu-AF20513, PRI-002, IRX-4204, GC-021109, AAD-2004, CTS-21166, LY-3323795, benfotiamine, bisnorcymserine, MDR-1339, KHK-6640, and NPT-088.

[item 85] The drug of item 80, wherein the aforementioned tau protein remover and production inhibitor are at least one selected from the group consisting of tau protein vaccine, tau protein removing antibody, tau protein modifying inhibitor, tau protein coagulation inhibitor, and tau proteolysis promoter.

[item 86] The drug of item 80, wherein the aforementioned tau protein remover and production inhibitor are at least one selected from the group consisting of TRx-237, TPI-287, ABBV-8E12, RG-6100, AADvac1, RO7105705, PTI-80, JNJ-63733657, UCB-0107, BIIB-076, MC-1, ACI-35, and AZP-2006.

[item 87] A therapeutic or prophylactic drug for Alzheimer's disease, comprising, as an active ingredient, a medicament that decreases the amount of polypeptide of item 1 or item 2 in the body of an Alzheimer's disease patient or a person who may be affected with Alzheimer's disease, or a medicament that inhibits production of the polypeptide in the body of an Alzheimer's disease patient or a person who may be affected with Alzheimer's disease.

[item 88] The drug of item 87, wherein the aforementioned polypeptide of item 1 or 2 is detected using the antibody of any one of items 4-9.

[item 89] A method for screening for a candidate substance for a therapeutic or prophylactic drug for Alzheimer's disease, comprising using, as an index, reduction of the amount of polypeptide of item 1 or 2 in the body of an Alzheimer's disease patient or a person who may be affected with Alzheimer's disease, or inhibition of production of the polypeptide in the body of an Alzheimer's disease patient or a person who may be affected with Alzheimer's disease.

[item 90] The method of item 89, wherein a decrease in the amount of the aforementioned polypeptide of item 1 or 2 is detected using the antibody of any one of items 4-9.

Advantageous Effects of Invention

According to the present invention, an agent for determining Alzheimer's disease, a method for determining Alzheimer's disease, a method for treating Alzheimer's disease, a method for screening for a candidate compound for a therapeutic drug for Alzheimer's disease, a novel anti-S38AA antibody and the like can be provided.

BRIEF DESCRIPTION OF DRAWINGS

FIG. 1 shows the amino acid sequence of S38AA. The sequence of the peptide detected by the LC-MS/MS method in identifying the N-terminal of the S38AA long fragment is shown in bold letters.

FIG. 2 shows MS/MS peak spectrum of $^{399}$EEVPEDLAEEAPGGR$^{413}$ peptide detected by the LC-MS/MS method in identifying the N-terminus of the S38AA long fragment. The vertical axis shows the peak intensity of each ion, and the horizontal axis shows m/z.

FIG. 3 shows the amino acid sequence of S38AA. The sequence of the peptide detected by the LC-MS/MS method in identifying the N-terminal of the S38AA short fragment is shown in bold letters.

FIG. 4 shows the MS/MS peak spectrum of $^{617}$GLAVGGGEKAK$^{627}$ peptide detected by the LC-MS/MS method in identifying the N-terminus of the S38AA short fragment. The vertical axis shows the peak intensity of each ion, and the horizontal axis shows m/z.

FIG. 5 shows the amino acid sequence of S38AA. The sequence of peptide detected by the LC-MS/MS method in identifying the C-terminus of the S38AA long fragment is shown in bold letters.

FIG. 6 shows MS/MS peak spectrum of $^{1040}$DLKLQAGSDL$^{1049}$ peptide detected by the LC-MS/MS method in identifying the C-terminus of the S38AA long fragment. The vertical axis shows the peak intensity of each ion, and the horizontal axis shows m/z.

DESCRIPTION OF EMBODIMENTS

Figure 7:
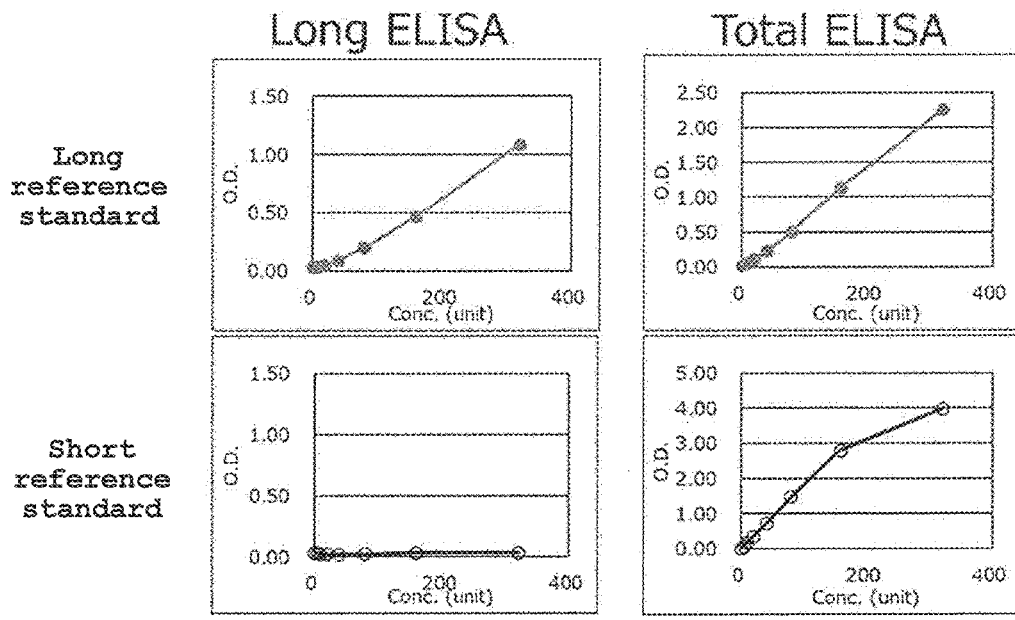
FIG. 7 shows the quantitativeness (calibration curve) when the expression levels of recombinant proteins of S38AA long fragment and S38AA short fragment in *Escherichia coli* were measured by Long ELISA and Total ELISA measurement systems, respectively. The vertical axis of each graph shows the absorbance at 450 nm, and the horizontal axis shows the concentration of each protein.

In the present specification, the "Alzheimer's disease" includes both the aforementioned "familial Alzheimer's disease" and "sporadic Alzheimer's disease".

In the present invention, "affected with Alzheimer's disease" namely, being an "Alzheimer's disease patient" refers to a condition that can be diagnosed as Alzheimer's disease by clinical diagnosis based on disorder of memory or cognitive function, or diagnostic imaging based on brain atrophy and the like.

In the present specification, "having Alzheimer's disease" means a condition diagnosed with Alzheimer's disease based on clinical diagnostic criteria for Alzheimer's disease, for example, the diagnostic criteria of the U.S. National Institute of Neurological Disorders and Stroke and Alzheimer's Disease and Related Disorders Association (NINCDS-ADRDA), or the Alzheimer's disease revised diagnostic criteria (hereinafter to be abbreviated as "Alzheimer's disease revised diagnostic criteria (2011)") by the U.S. National Institute on Aging and Alzheimer's Association (NIA-AA) and the like.

In all diagnostic criteria, the presence of cognitive dysfunction centering on memory disorder, slow onset and progressive process, impaired social life and activities of daily living which are associated with cognitive impairment, and differentiation/exclusion of non-AD type dementia, and the like are indicators of diagnosis.

The state of onset of Alzheimer's disease is divided into three stages (mild, moderate (or intermediate), higher (or severe), or first stage (or amnesia stage), second stage (or confusion period), third stage (or recumbency period)) depending on the severity of the symptoms. The severity can be evaluated using Mini Mental State Examination (MMSE), which measures the degree of cognitive dysfunction, Functional Assessment Staging (FAST) of dementia that determines the severity mainly based on activities of daily living, Clinical Dementia Rating (CDR) that clinically determines the severity, Alzheimer's Disease Assessment Scale-Cognitive (ADAS-cog) and Severe Impairment Battery (SIB) used in clinical test, and the like.

As a method of evaluating the degree of disorder of cognitive function in Alzheimer's disease, for example, the score of the Mini Mental State Examination (MMSE) can be used as one of the criteria. Of the scale of 0 to 30, as a guide, not more than 9 points is judged to be severe Alzheimer's disease, 10 to 19 points to be moderate Alzheimer's disease, 20 to 23 points to be mild Alzheimer's disease, and 24 points or more to be mild cognitive impairment or normal.

In the present specification, the "people at risk of Alzheimer's disease" (Pre-Alzheimer's disease), that is, "a person who may be affected with Alzheimer's disease (human)", "one (human) in high risk group of Alzheimer's disease" include humans in a state where accumulation of Aβ and tau protein in the brain tissue has started, and Alzheimer's disease is highly likely developed in the near future, that is, a state in which Aβ and tau protein are accumulated in brain tissue (also called Preclinical AD), even though the onset of Alzheimer's disease cannot be diagnosed according to the aforementioned diagnosis. Here, the accumulation of Aβ or tau protein in the brain tissue can be confirmed using amyloid PET or tau PET, Aβ or phosphorylated tau in the cerebral spinal fluid, and the like as biomarkers.

In the present specification, "Preclinical AD" is, as defined in the Preclinical AD research criteria in the aforementioned Alzheimer's disease revised diagnostic criteria (2011), a state in which the biomarker suggesting the pathology of Alzheimer's disease is positive, but the cognitive function is normal or only minor cognitive dysfunction that does not meet the diagnostic criteria of mild cognitive impairment (MCI) is found.

Humans who are not diagnosed with Alzheimer's disease but are diagnosed with mild cognitive impairment are included in "one (human) who may be affected with Alzheimer's disease" because the symptom is the sign of Alzheimer's disease and may cause Alzheimer's disease in the future.

In the present specification, the "mild cognitive impairment (or mild cognitive dysfunction)" (MCI) is an intermediate state between normal and dementia, where cognitive function is worse than normal, but daily life is maintained and dementia is not diagnosed, i.e., a precursor state to dementia.

The diagnosis of mild cognitive impairment can be performed based on, for example, the diagnostic criteria proposed at the 2003 MCI Key Symposium (Winblad B et al., (2004) J. Intern. Med. 256: 240-246), or the diagnostic criteria for mild cognitive impairment described in the aforementioned Alzheimer's disease revised diagnostic criteria (2011) by NIA-AA.

When the evaluation score of the severity of dementia is the index, as a guide, CDR (Clinical Dementia Rating) score of 0.5 (suspected dementia), or FAST (Functional Assessment Staging) stage of 3 (suspected dementia) corresponds to mild cognitive impairment. When the aforementioned MMSE score is the index, as a guide, a score of not less than 24 with no diagnosis of Alzheimer's disease corresponds to mild cognitive impairment. The score of 24-28 indicates high possibility of mild cognitive impairment.

1. Polypeptide of the Present Invention

The present inventors have first found that the amount of S38AA long fragment produced by cleavage in the extramembrane part of S38AA increases in the blood of AD patients, further that, in the blood of AD patients, an enzyme that specifically cleaves the C-terminal side of the long fragment is present, or the activity of the enzyme is high, and the amount of S38AA short fragment increases significantly, and that the amount of S38AA short fragment in blood is higher than that of healthy individuals regardless of whether the severity of Alzheimer's disease (progression of cognitive dysfunction) is mild, moderate or severe, and it is higher in moderate and severe than in mild. Thus, they have found that the amount of S38AA short fragment is extremely highly reliable as a highly accurate index for determining the onset of Alzheimer's disease and people at risk of the disease.

Therefore, the present invention first provides a polypeptide consisting of the amino acid sequence shown in SEQ ID NO: 1 as the S38AA short fragment (corresponding to the 617th-1049th amino acid sequence in the amino acid sequence (1-1119) of S38AA shown in SEQ ID NO: 3), and a polypeptide consisting of the amino acid sequence shown in SEQ ID NO: 2 as the S38AA long fragment (corresponding to the 399th-1049th amino acid sequence in the amino acid sequence (1-1119) of S38AA shown in SEQ ID NO: 3).

As long as recognized by an antibody that specifically binds to the polypeptide consisting of the amino acid sequence shown in the below-mentioned SEQ ID NO: 1, 1 to several amino acids in the amino acid sequence of S38AA short fragment may be substituted, deleted, added or inserted. Similarly, as long as recognized by an antibody that specifically binds to the polypeptide consisting of the amino acid sequence shown in the below-mentioned SEQ ID NO: 2, 1 to several amino acids in the amino acid sequence of S38AA long fragment may be substituted, deleted, added or inserted. As used herein, several is not particularly limited and may be, for example, 2-10, 2-8, 2-6, 2-4, 2-3, or 2.

The S38AA short fragment may be modified at its N-terminal, C-terminal, or side chain by a method well known to those skilled in the art, for example, N-terminal acetyl group modification, C-terminal amide group modification, addition of a protein tag (His tag, etc.) to the N terminus and/or C-terminus, addition of a sugar chain to the side chain, or the like.

The polypeptide of the present invention can be produced according to a known peptide synthesis method, for example, solid phase synthesis process, liquid phase synthesis process and the like. The obtained polypeptide can be purified and isolated by a known purification method, for example, solvent extraction, distillation, column chromatography, liquid chromatography, recrystallization, a combination of these, and the like.

The polypeptide of the present invention can also be produced by culturing a transformant containing the nucleic acids encoding the polypeptide and separating and purifying the polypeptide from the resulting culture. The nucleic acids encoding the polypeptide of the present invention may be DNA, RNA, or a DNA/RNA chimera, but is preferably DNA. The nucleic acids may be double-stranded or single-stranded. In the case of double strand, it may be double-stranded DNA, double-stranded RNA or a hybrid of DNA: RNA. In the case of a single strand, it may be either a sense strand (i.e., coding strand) or an antisense strand (i.e., non-coding strand).

In the present specification, "SEQ ID NO" and "SEQ ID NO:" are synonymous. For example, "SEQ ID NO 1" and "SEQ ID NO: 1" are synonymous.

The DNA encoding the polypeptide of the present invention includes synthetic DNA and the like, and can be obtained by a method known per se, for example, Reverse Transcriptase-PCR method, ODA-LA PCR method, Gapped duplex method, Kunkel method and the like, or colony or plaque hybridization method or PCR method.

2. Anti S38AA Antibody

The "anti-S38AA antibody" used in the present specification is not particularly limited as long as it is an antibody that specifically recognizes S38AA, or an antibody that specifically recognizes S38AA long fragment and/or S38AA short fragment. For example, an antibody that recognizes the N-terminal region of S38AA long fragment, an antibody that recognizes the C-terminal region of S38AA long fragment, an antibody that recognizes the C-terminal region common to S38AA long fragment and S38AA short fragment and the like can be mentioned.

The anti-S38AA antibody may also be a commercially available anti-S38AA antibody, a polyclonal or monoclonal antibody produced by using a known method, or a fragment thereof (e.g., Fab, F(ab')$_2$, ScFv, minibody, etc.).

As the anti-S38AA antibody to be used in the present invention, a monoclonal antibody and a polyclonal antibody derived from mammals are preferable.

Examples of the monoclonal antibody and polyclonal antibody derived from mammals include those produced in the blood of animal, those produced by hybridomas, and those produced by a host transformed with an expression vector containing an antibody gene by a genetic engineering means, those mass-produced in CHO cells having the gene of an optimal antibody screened for from an enormous clone library consisting of 1,000,000,000,000 molecules by phage display, or human antibody directly produced using transgenic mouse that produces human antibody, and the like.

Monoclonal antibody and polyclonal antibody can be produced by a known method to those of ordinary skill in the art.

(1) Production of Monoclonal Antibody

The polypeptide of the present invention is administered alone or together with a carrier or a diluent to a site where an antibody can be produced by administration to a mammal. To increase antibody producibility by administration, complete Freund's adjuvant or incomplete Freund's adjuvant may also be administered. The administration is generally performed once every 2-6 weeks, and about 2-10 times in total. Examples of the mammal to be used include monkey, rabbit, dog, guinea pig, mouse, rat, sheep and goat, with preference given to mouse and rat.

For the production of monoclonal antibody-producing cells, from mammals, for example, mice, immunized with an antigen, individuals found to show antibody titer are selected, the spleen or lymph node is collected 2-5 days after the final immunization, the antibody-producing cells contained therein are fused with myeloma cells, whereby a monoclonal antibody-producing hybridoma can be prepared. The antibody titer in antiserum can be measured by, for example, reacting the below-mentioned labeled S38AA with antiserum, and measuring the activity of the label bound to the antibody. A fusion operation can be performed by a known method, for example, the method of Köhler and Milstein [Nature, 256, 495 (1975)]. As the fusion stimulant, for example, polyethylene glycol (PEG), Sendai virus and the like can be mentioned, and PEG is preferably used. To enhance fusion efficiency, moreover, an adjuvant such as dimethyl sulfoxide and the like can also be used as appropriate.

As the myeloma cell, for example, NS-1, P3U1, SP2/0 and the like can be mentioned, and P3U1 is preferably used. A preferable ratio of the numbers of the antibody-producing cells (spleen cells) and myeloma cells to be used is about 1:1-20:1, PEG (preferably PEG 1000-PEG 6000) is added at a concentration of about 10-80%, and the cell fusion can be efficiently performed by incubating at about 20-40° C., preferably about 30-37° C., for about 1-10 min.

For screening for a monoclonal antibody-producing hybridoma, various methods can be used. Examples thereof include a method including adding a hybridoma culture supernatant to a solid phase (e.g., microplate) adsorbed with antigen such as protein and the like directly or together with carrier, adding anti-immunoglobulin antibody labeled with radioactive substance, enzyme or the like (when the cell used for cell fusion is from a mouse, anti-mouse immunoglobulin antibody is used) or protein A, and detecting monoclonal antibody bound to the solid phase, a method comprising adding a hybridoma culture supernatant to a solid phase adsorbed with anti-immunoglobulin antibody or protein A, adding protein labeled with radioactive substance, enzyme etc., and the like, and detecting monoclonal antibody bound to the solid phase, and the like.

The monoclonal antibody can be selected by a method known per se or a method analogous thereto, and can be generally selected using a medium for animal cells which is added with HAT (hypoxanthine, aminopterine, thymidine), and the like. As the medium for selection and growth, any medium can be used as long as hybridomas can grow. For example, RPMI 1640 medium containing 1-20%, preferably 10-20%, of fetal bovine serum, GIT medium containing 1-10% of fetal bovine serum (Wako Pure Chemical Industries, Ltd.), a serum-free medium for hybridoma culture (SFM-101, Nissui Pharmaceutical Co., Ltd.) and the like can be used. The culture temperature is generally 20-40° C., preferably about 37° C. The culture time is generally 5 days-3 weeks, preferably 1 week-2 weeks. Culture can be generally performed in 5% carbon dioxide gas. The antibody titer of the hybridoma culture supernatant can be measured in the same manner as in the above-mentioned measurement of the antibody titer of the antiserum.

The monoclonal antibody can be separated and purified according to a separation and purification method of immunoglobulin, in the same manner as in general separation and purification of polyclonal antibody [e.g., salting-out method, alcohol precipitation method, isoelectric point precipitation method, electrophoresis, adsorption and desorption method by ion exchanger (e.g., DEAE), ultracentrifugation method, gel filtration method, specific purification method including collecting only an antibody by an active adsorbent such as antigen-bound solid phase, protein A, protein G or the like, and dissociating the bond to give the antibody].

(2) Production of Polyclonal Antibody

Polyclonal antibody to the polypeptide of the present invention can be produced by a method known per se or a method analogous thereto. For example, a polyclonal antibody can be produced by producing a complex of an immunizing antigen (antigen such as protein and the like) and a carrier protein, immunizing a mammal in the same manner as in the above-mentioned production method of the monoclonal antibody or chicken, collecting a substance containing the antibodies to S38AA from the immunized animal, and separating and purifying the antibodies.

As for the complex of an immunizing antigen and a carrier protein to be used for immunizing a mammal or chicken, the kind of the carrier protein and the mixing ratio of the carrier and hapten may be any and any ratio as long as the antibody can be efficiently produced against hapten crosslinked with the carrier used for immunization. For example, a method including coupling bovine serum albumin, bovine thyroglobulin, keyhole limpet hemocyanin and the like at a weight ratio of about 0.1-20, preferably about 1-5, to hapten of 1 is used.

While various condensing agents can be used for coupling hapten with a carrier, an activated ester reagent containing glutaraldehyde, carbodiimide, maleimide activated ester, a thiol group and a dithiopyridyl group, and the like can be used.

The condensed product is administered to a mammal or chicken alone or together with a carrier and a diluent to a site where antibody can be produced. To increase antibody producibility by administration, a complete Freund's adjuvant or incomplete Freund's adjuvant may also be administered. The administration is generally performed once every 2-6 weeks, and about 3-10 times in total.

The polyclonal antibody can be collected from the blood, ascites, breast milk and the like of the mammal immunized by the above-mentioned method, preferably from the blood, and in the case of chicken, it can be collected from the blood and egg-yolk.

The titer of the polyclonal antibody in the antiserum can be measured in the same manner as in the above-mentioned measurement of the antibody titer of the antiserum. The polyclonal antibody can be separated and purified according to a separation and purification method of immunoglobulin, in the same manner as in the above-mentioned separation and purification of monoclonal antibody.

As the polyclonal antibody in the present invention, for example, rabbit-derived anti-S38AA polyclonal antibody (hereinafter to be also referred to as "MBL" or "antibody for long fragment") can be mentioned. The antibody for long fragment is characterized in that it specifically recognizes S38AA long fragment and does not recognize S38AA short fragment. The antibody for long fragment can be used for Long ELISA described later by using the antibody together with antibodies A, B, or C.

(3) Antibody that Specifically Recognizes S38AA Short Fragment

As one embodiment of the present invention, an antibody that specifically recognizes the S38AA short fragment shown in SEQ ID NO: 1 can be mentioned. As an antibody that specifically recognizes the S38AA short fragment, for example, an antibody that recognizes the C-terminal sequence or the N-terminal sequence of the S38AA short fragment can be mentioned. An antibody that specifically recognizes S38AA short fragment can be prepared by a method well known to those skilled in the art. For example, it can be obtained using a peptide consisting of several amino acids from the N-terminal of the S38AA short fragment (617th glycine in the amino acid sequence shown in SEQ ID NO: 3) as an immune antigen, and selecting an antibody that is negative for a peptide which is the immune antigen added with several amino acids to its N-terminal side, or S38AA long fragment. Specifically, a monoclonal antibody or a polyclonal antibody can be obtained according to the above-mentioned method (1) or (2), respectively.

Examples of the antibody that specifically recognizes S38AA short fragment include the below-mentioned antibody A, antibody B and antibody C.

Antibody A (hereinafter to be also referred to as "mouse-derived anti-S38AA monoclonal antibody A") is an antibody that recognizes the C-terminal region of S38AA, and means an antibody obtained by establishing an antibody-producing hybridoma by using a part of the peptide of the C-terminal amino acid sequence of the S38AA fragment as an immunogen, followed by separation and purification. Antibody A is characterized in that it specifically recognizes S38AA short fragment and S38AA long fragment. Antibody A can be used for Long ELISA together with the "antibody for long fragment". Antibody A can be used for Total ELISA described later by using the antibody together with antibody B or C.

Antibody A is preferably an antibody selected from the group consisting of the following:
(1) an antibody comprising the heavy chain variable region of SEQ ID NO: 4,
(2) an antibody comprising the heavy chain variable region of SEQ ID NO: 6,
(3) an antibody comprising the heavy chain variable region of SEQ ID NO: 8, and
(4) an antibody comprising the heavy chain variable region of SEQ ID NO: 10.

Another preferred embodiment of antibody A is an antibody selected from the group consisting of the following:
(1) an antibody comprising the light chain variable region of SEQ ID NO: 5,
(2) an antibody comprising the light chain variable region of SEQ ID NO: 7,
(3) an antibody comprising the light chain variable region of SEQ ID NO: 9, and
(4) an antibody comprising the light chain variable region of SEQ ID NO: 11.

More preferably, antibody A is an antibody selected from the group consisting of the following:
(1) an antibody comprising the heavy chain variable region of SEQ ID NO: 4, and the light chain variable region of SEQ ID NO: 5,
(2) an antibody comprising the heavy chain variable region of SEQ ID NO: 6, and the light chain variable region of SEQ ID NO: 7,
(3) an antibody comprising the heavy chain variable region of SEQ ID NO: 8, and the light chain variable region of SEQ ID NO: 9, and
(4) an antibody comprising the heavy chain variable region of SEQ ID NO: 10, and the light chain variable region of SEQ ID NO: 11.

Antibody B is an antibody that recognizes the C-terminal region of S38AA, and means an antibody obtained by establishing an antibody-producing hybridoma by using a part of the peptide of the C-terminal amino acid sequence of the S38AA fragment as an immunogen, followed by separation and purification. Antibody B is characterized in that it specifically recognizes S38AA short fragment and S38AA long fragment. Antibody B can be used for Long ELISA together with the "antibody for long fragment". Antibody B can be used for Total ELISA by using the antibody together with antibody A or C.

Antibody B is preferably an antibody selected from the group consisting of the following:
(5) an antibody comprising the heavy chain variable region of SEQ ID NO: 12,
(6) an antibody comprising the heavy chain variable region of SEQ ID NO: 14,
(7) an antibody comprising the heavy chain variable region of SEQ ID NO: 16, and
(8) an antibody comprising the heavy chain variable region of SEQ ID NO: 18.

Another preferred embodiment of antibody B is an antibody selected from the group consisting of the following:
(5) an antibody comprising the light chain variable region of SEQ ID NO: 13,
(6) an antibody comprising the light chain variable region of SEQ ID NO: 15,
(7) an antibody comprising the light chain variable region of SEQ ID NO: 17, and
(8) an antibody comprising the light chain variable region of SEQ ID NO: 19.

Antibody B is more preferably an antibody selected from the group consisting of the following:
(5) an antibody comprising the heavy chain variable region of SEQ ID NO: 12, and the light chain variable region of SEQ ID NO: 13,
(6) an antibody comprising the heavy chain variable region of SEQ ID NO: 14, and the light chain variable region of SEQ ID NO: 15,
(7) an antibody comprising the heavy chain variable region of SEQ ID NO: 16, and the light chain variable region of SEQ ID NO: 17, and
(8) an antibody comprising the heavy chain variable region of SEQ ID NO: 18, and the light chain variable region of SEQ ID NO: 19.

Antibody C is an antibody that recognizes the C-terminal region of S38AA, and means an antibody obtained by establishing an antibody-producing hybridoma by using recombinant protein of the S38AA long fragment in *Escherichia coli* as an immunogen, followed by separation and purification. Antibody C is characterized in that it specifically recognizes S38AA short fragment and S38AA long fragment. Antibody C can be used for Long ELISA together with the "antibody for long fragment". Antibody C can be used for Total ELISA by using the antibody together with antibody A or B.

Antibody C is preferably an antibody selected from the group consisting of the following:
(9) an antibody comprising the heavy chain variable region of SEQ ID NO: 20, and
(10) an antibody comprising the heavy chain variable region of SEQ ID NO: 22.

Another preferred embodiment of antibody C is an antibody selected from the group consisting of the following:
(9) an antibody comprising the light chain variable region of SEQ ID NO: 21, and
(10) an antibody comprising the light chain variable region of SEQ ID NO: 23.

Antibody C is more preferably an antibody selected from the group consisting of the following:
(9) an antibody comprising the heavy chain variable region of SEQ ID NO: 20, and the light chain variable region of SEQ ID NO: 21, and
(10) an antibody comprising the heavy chain variable region of SEQ ID NO: 22, and the light chain variable region of SEQ ID NO: 23.

As long as the antibodies A, B and C of the present invention can specifically recognize S38AA short fragment and S38AA long fragment, the respective antibodies may contain a variable region having a homology of not less than 90%, preferably not less than 95%, more preferably not less than 96%, still more preferably not less than 97%, further preferably 98%, further more preferably not less than 99%, most preferably not less than 99.5%, with the amino acid sequence of the above-mentioned variable region contained therein.

In the present specification, "homology" means the proportion (%) of the same amino acids and similar amino acid residues to the overlapping total amino acid residues in the optimal alignment (preferably, the algorithm can consider, for the optimal alignment, introduction of a gap into one or both of the sequences), when two amino acid sequences are aligned using mathematical algorithm known in the technical field.

The homology of the amino acid sequence in the present specification can be calculated using the homology calculation algorithm NCBI BLAST (National Center for Biotechnology Information Basic Local Alignment Search Tool) under the following conditions (expectancy=10; gap; matrix=BLOSUM62; filtering=OFF). Examples of other algorithm to determine the homology of amino acid sequence include the algorithm described in Karlin et al., Proc. Natl. Acad. Sci. USA, 90:5873-5877(1993) [the algorithm is incorporated in NBLAST and XBLAST program (version 2.0) (Altschul et al., Nucleic Acids Res., 25:3389-3402(1997))], the algorithm described in Needleman et al., J. Mol. Biol., 48:444-453(1970) [the algorithm is incorporated in GAP program in GCG software package], the algorithm described in Myers and Miller, CABIOS, 4:11-

17(1988) [the algorithm is incorporated in ALIGN program (version 2.0) which is a part of the CGC sequence alignment software package], the algorithm described in Pearson et al., Proc. Natl. Acad. Sci. USA, 85: 2444-2448(1988) [the algorithm is incorporated in FASTA program in the GCG software package] and the like, and they can also be preferably used in the same manner.

CDR contained in antibodies A, B and C of the present invention may contain 1 to several (2, 3, 4, 5, etc.), preferably within 2, more preferably one, amino acid substituted, deleted, inserted, and/or added in the amino acid sequence of one CDR as long as the antibodies can specifically recognize S38AA short fragment and S38AA long fragment. The number of CDRs in which amino acids of each of the above-mentioned antibodies are substituted, deleted, inserted, and/or added is not particularly limited as long as each antibody can specifically recognize S38AA short fragment and S38AA long fragment. It is preferably within 2, more preferably 1, per one light chain variable region, and preferably within 2, more preferably 1, per one heavy chain variable region. The substitution, deletion, insertion, and/or addition of the amino acids may be performed in both the light chain variable region and the heavy chain variable region, or either one alone.

For example, "similar amino acid" means amino acids similar in physicochemical properties and, for example, amino acids classified into the same group such as aromatic amino acid (Phe, Trp, Tyr), aliphatic amino acid (Ala, Leu, Ile, Val), polar amino acid (Gln, Asn), basic amino acid (Lys, Arg, His), acidic amino acid (Glu, Asp), amino acid having hydroxyl group (Ser, Thr), amino acid with small side chain (Gly, Ala, Ser, Thr, Met) and the like can be mentioned. Substitution with such similar amino acids is predicted to cause no change in the phenotype of the protein (i.e., conservative amino acid substitution). Specific examples of the conservative amino acid substitution are well known in the art and described in various documents (see, for example, Bowie et al., Science, 247:1306-1310(1990)).

Examples of the method for substituting one or more amino acid residues with other desired amino acids include Site-Directed Mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492). Using the method, desired amino acids of an antibody can be substituted with other desired amino acids. It is also possible to substitute amino acids in framework and CDR with other appropriate amino acids by using library techniques such as framework shuffling (Mol Immunol. 2007 April; 44(11):3049-60) and CDR repair (US2006/0122377) and the like.

3. Agent for Determining Alzheimer's Disease

The determining agent of the present invention contains one or plural kinds of anti-S38AA antibodies capable of detecting the amount of S38AA Short fragment, and can determine not only whether a person is affected with Alzheimer's disease and whether highly likely affected with the disease at present, but also people at risk of Alzheimer's disease, that is, whether the person has a high possibility of being affected with the disease in the near future, though the person is not yet suffering from the disease. In other words, the agent of the present invention can identify Alzheimer's disease irrespective of whether the severity is mild, moderate, or severe. Therefore, the "determination" of Alzheimer's disease in the present invention is used to mean not only determination of whether a person is already affected with Alzheimer's disease and whether highly likely affected with the disease at present, but encompass judgment of whether a person has a high possibility of being affected in the near future, though the person is not yet suffering from the disease.

4. Kit for Determining Alzheimer's Disease

The present invention provides a kit for determining Alzheimer's disease. The kit of the present invention contains a reagent for measuring the amount of the S38AA short fragment. By measuring the amount of the S38AA short fragment using the kit of the present invention, Alzheimer's disease can be determined.

The kit of the present invention contains an anti-S38AA antibody that is a single antibody or a combination of plural antibodies capable of quantifying S38AA short fragments and, specifically, an antibody that specifically recognizes S38AA short fragment, or an antibody that recognizes S38AA long fragment and does not recognize S38AA short fragment, and a combination of an antibody that recognizes both S38AA long fragment and S38AA short fragment can be mentioned. As the antibody that recognizes S38AA long fragment and does not recognize S38AA short fragment, for example, an antibody that recognizes the N-terminal side region of the aforementioned S38AA long fragment can be mentioned. As the antibody that recognizes both S38AA long fragment and S38AA short fragment, an antibody that recognizes the C-terminal side region common to S38AA long fragment and S38A short fragment can be mentioned.

The antibody used for the kit of the present invention is preferably an antibody for long fragment, antibody A, antibody B, and/or antibody C.

The antibody may be a fluorescence-labeled antibody, enzyme-labeled antibody, streptavidin-labeled antibody, biotin-labeled antibody or radioactive-labeled antibody.

The anti-S38AA antibody is generally contained in the kit of the present invention in the form of an aqueous solution thereof dissolved in water or a suitable buffer (e.g., TE buffer, PBS etc.) at a suitable concentration or a freeze-dried product.

For measurement of the S38AA short fragment and/or S38AA long fragment, one kind of antibody may be used for the measurement, and plural kinds, preferably two kinds, of antibodies may be used for the measurement (e.g., sandwich ELISA method and the like).

The kit of the present invention may further contain, in its constitution, other components necessary for performing the method, according to the measurement method of short S38AA fragment. For example, for measurement by Western blot, the kit of the present invention can further contain a blotting buffer, a labeling reagent, a blotting membrane and the like, a determination reagent, a standard solution and the like. Examples of the "standard solution" here include a purified reference standard of S38AA short fragment and/or S38AA long fragment, for example, an aqueous solution obtained by dissolving the peptide of the present invention in water or a suitable buffer (e.g., TE buffer, bovine fetal serum-containing PBS and the like) at a particular concentration.

For measurement by sandwich ELISA, the kit of the present invention can further contain, in addition to the above, an immobilized antibody measurement plate, a washing solution and the like. For measurement by an agglutination method including latex agglutination method, an antibody-coated latex, gelatin or the like can be contained. For measurement by a chemical fluorescence method or a chemical fluorescence electron method, antibody-conjugated magnetic particles and a suitable buffer can be contained. For detection of S38AA by using LC/MS, LC-MS/MS or an immunochromatography method, an antibody-coated column or micro column, and a micro chip can be contained as a part of the detection instrument. Furthermore, in a time-resolved fluorescence measurement method or a fluorescence measurement method similar thereto, a plurality of labeled anti-S38AA antibodies and other necessary components may be contained in the constitution.

As the kit of the present invention, for example, the following can be mentioned. The antibody contained in the following kits may be labeled (e.g., labeling with peroxidase, biotin, etc.). When the antibody is not labeled, a labeled antibody that labels the antibody by binding to the antibody may be contained separately.

1) one or two kinds of "antibody that specifically recognizes S38AA short fragment", washing solution, color development reagent, reaction quenching liquid, dilution buffer and standard solution;
2) one or two kinds of "antibody that recognizes the N-terminal side region of S38AA long fragment", one or two kinds of "antibody that recognizes C-terminal side region of S38AA long fragment (that is, antibody that recognizes the C-terminal side region common to S38AA long fragment and S38A short fragment)", washing solution, color development reagent, reaction quenching liquid, dilution buffer and standard solution;
3) "the first antibody that specifically recognizes S38AA short fragment", "the second antibody that specifically recognizes S38AA short fragment", washing solution, color development reagent, reaction quenching liquid, dilution buffer and standard solution;
4) "the first antibody that recognizes the N-terminal region of S38AA long fragment" and "the second antibody that specifically recognizes S38AA long fragment", one or two kinds of "antibody that recognizes C-terminal side region of S38AA long fragment (that is, antibody that recognizes the C-terminal side region common to S38AA long fragment and S38A short fragment)", washing solution, color development reagent, reaction quenching liquid, dilution buffer and standard solution.

As used herein, the "antibody that specifically recognizes S38AA short fragment", "the first antibody that specifically recognizes S38AA short fragment", and "the second antibody that specifically recognizes S38AA short fragment" are preferably antibody A, antibody B and antibody C.

As used herein, the "antibody that recognizes the N-terminal region of S38AA long fragment" and "the first antibody that recognizes N-terminal side region of S38AA long fragment" are preferably "antibody for long fragment".

As used herein, "antibody that recognizes C-terminal side region of S38AA long fragment (that is, antibody that recognizes the C-terminal side region common to S38AA long fragment and S38AA short fragment)" preferably include antibody A, antibody B and antibody C. Examples of the anti-S38AA long fragment antibody and anti-S38AA short fragment antibody that can specifically detect S38AA long fragment and S38AA short fragment include the antibodies described in detail in "2. Antibody of the present invention".

5. Method of the Present Invention (1) Determining and Test Method of Alzheimer's Disease As mentioned above, the present inventors have first found that the amount of S38AA long fragment produced by cleavage in the extramembrane part of S38AA increases in the blood of AD patients, further that, in the blood of AD patients, an enzyme that specifically cleaves the long fragment is present, or the activity of the enzyme is high, and the amount of S38AA short fragment produced by direct cleavage in the extramembrane part of S38AA increases significantly, and that the amount of S38AA short fragment in blood increases regardless of whether the severity of Alzheimer's disease (progression of cognitive dysfunction) is mild, moderate or severe, and it is higher in moderate and severe than in mild. Thus, they have found that the amount of S38AA short fragment is extremely highly reliable as a highly accurate index for determining the onset of Alzheimer's disease and people at risk of the disease, and an index for determining the degree of progression of Alzheimer's disease.

Thus, the present invention provides a method for determining Alzheimer's disease, for example, mild or moderate or severe Alzheimer's disease, comprising detecting an S38AA short fragment in a sample collected from a test animal.

The determination method of the present invention can determine not only whether a person is affected with Alzheimer's disease and whether highly likely affected with the disease at present, but also whether the person has a high possibility of being affected with the disease in the near future, though the person is not yet suffering from the disease.

The present invention also provides a method for testing the possibility of being affected with Alzheimer's disease at present or the possibility of being affected with Alzheimer's disease in the future, the method comprising detecting an S38AA short fragment in a sample collected from a test animal.

The above-mentioned determination and test (results) of the possibility are useful for assisting at least definitive diagnosis of Alzheimer's disease by a doctor.

The determining and test method of the present invention is characterized by detection of S38AA short fragment in a sample collected from a test animal. In addition, the determining and test method of the present invention may include as a specific step, for example, (i) a step of quantifying S38AA short fragment in a sample collected from a test animal, and (ii) a step of comparing the amount of S38AA short fragment quantified in (i) with the amount of S38AA short fragment in a sample collected from a healthy animal (hereinafter to be referred to as "control value").

As the result of the comparison in (ii), it is shown that the aforementioned test animal is affected with Alzheimer's disease, or may be affected with Alzheimer's disease at present or may be affected with Alzheimer's disease in the future, when the amount of the S38AA short fragment quantified in (i) is higher than the control value.

Furthermore, the determining and test method of the present invention may include, in addition to the above-mentioned step, a step of determining based on the results of (ii) that the aforementioned test animal is affected with Alzheimer's disease, or may be affected with Alzheimer's disease at present or may be affected with Alzheimer's disease in the future, when the amount of the S38AA short fragment quantified in (i) is higher than the control value.

Furthermore, the present invention provides a method for assisting in determining the progression of Alzheimer's disease because the value of S38AA short fragment in blood increases regardless of whether the severity of Alzheimer's disease (progression of cognitive dysfunction) is mild, moderate or severe, and further, it is higher in moderate and severe than in mild, as described above.

The method for assisting in determining of the present invention characteristically detects S38AA short fragment in a sample collected from a test animal. The method for assisting in determining of the present invention may include as specific steps, for example, (i) a step of quantifying S38AA short fragment in a sample collected from a test animal that is or may be affected with Alzheimer's disease, and (ii) a step of comparing the amount of the S38AA short fragment quantified in (i) with the amount of the S38AA short fragment in a sample collected in the past from the test animal (hereinafter to be referred to as "control value").

As the result of the comparison in (ii), when the amount of the S38AA short fragment quantified in (i) is higher than the control value, it indicates that the Alzheimer's disease in the aforementioned test animal is progressing or the possibility of being affected with Alzheimer's disease is high, and when the amount is smaller than the control value, it indicates that the Alzheimer's disease of the aforementioned test animal is improving or the possibility of not being affected with Alzheimer's disease is high.

The method for assisting in determining of the present invention may include, in addition to the above-mentioned steps, (iii) a step of determining based on the results of (ii) that the Alzheimer's disease in the aforementioned test animal is progressing when the amount of the S38AA short fragment quantified in (i) is higher than the control value, and the Alzheimer's disease of the aforementioned test animal is improving when the amount is smaller than the control value.

Moreover, the present invention also provides a method for evaluating the treatment effect on the patients under treatment of Alzheimer's disease or people at risk of Alzheimer's disease who are under treatment to prevent the onset of Alzheimer, because the amount of S38AA short fragment in blood increases regardless of whether the severity of Alzheimer's disease (progression of cognitive dysfunction) is mild, moderate or severe, and it is higher in moderate and severe than in mild, as described above.

The method for evaluating the treatment effect of the present invention is also characterized by detection of S38AA short fragment in a sample collected from a test animal. In addition, the method for evaluating the treatment effect of the present invention may include as a specific step, for example, (i) a step of quantifying S38AA short fragment in a sample collected from a test animal that has started medication treatment of Alzheimer's disease or medication treatment to prevent the onset of Alzheimer's disease, and (ii) a step of comparing the amount of S38AA short fragment quantified in (i) with the amount of S38AA short fragment in a sample collected from the test animal (sample collected before the start of medication treatment, sample collected after the start of medication treatment and before the time of collection in (i)) hereinafter to be referred to as "control value").

As the result of the comparison in (ii), it is shown that the current medication treatment (or selected therapeutic drug) is not effective when the amount of the S38AA short fragment quantified in (i) higher than the control value, and that the current medication treatment (or selected therapeutic drug) is effective when the amount is smaller than the control value.

The method for evaluating the treatment effect of the present invention may include, in addition to the above-mentioned steps, (iii) a step of determining based on the results of (ii) that the current medication treatment (or selected therapeutic drug) is not effective when the amount of the S38AA short fragment quantified in (i) is higher than the control value, and the current medication treatment (or selected therapeutic drug) is effective when it is smaller than the control value.

In the present specification, the therapeutic drug used for the medication treatment is a concept that includes not only therapeutic drugs that have already been approved and marketed, but also clinical trial drugs under clinical tests. The method for evaluating the treatment effect of the present invention can also be utilized for monitoring the drug efficacy in clinical tests, and the like.

While the animal that can be a test subject for the method of the present invention is not particularly limited as long as it expresses S38AA, for example, mammals (e.g., human, monkey, bovine, swine, horse, dog, cat, sheep, goat, rabbit, hamster, guinea pig, mouse, rat etc.), birds (e.g., chicken etc.) and the like can be mentioned. Preferred is a mammal, and more preferred is a human.

While a biological sample derived from a test animal to be the sample is not particularly limited, for example, blood, serum, plasma, saliva, lacrimal fluid, urine, cerebrospinal fluid and the like can be mentioned. More preferred is plasma or cerebrospinal fluid.

Serum and plasma can be prepared by collecting blood from a test animal according to a conventional method, and separating the liquid component. The cerebrospinal fluid can be collected by a known means such as spinal tap and the like.

An S38AA long fragment and S38AA short fragment in a sample can be detected (quantified) by a known method. They can be detected by subjecting to, for example, Western blot, gel electrophoresis (e.g., SDS-PAGE, two-dimensional gel electrophoresis and the like), various separation and purification methods (e.g., ion exchange chromatography, hydrophobic chromatography, gel filtration chromatography, affinity chromatography, reversed-phase chromatography, isoelectric point chromatography, capillary electrophoresis and the like), ionization method (e.g., electron impact ionization method, field desorption method, secondary ionization method, fast atom bombardment, matrix assisted laser desorption/ionization (MALDI) method, electrospray ionization method and the like), mass spectrometer (e.g., double-focusing mass spectrometer, quadrupol mass spectrometer, time-of-flight mass spectrometer, Fourier-transform mass spectrometer, ion cyclotron mass spectrometer and the like) and the like. Detection (quantification) using a measurement device applying these measurement principles is also included in the method of the present invention.

In addition, an S38AA long fragment and S38AA short fragment can also be detected (quantified) by a known immunochemical method (nephelometry, competitive method, immunometric method, chemical fluorescence method, chemical fluorescence electron method, sandwich method etc.). As for these immunochemical methods, reference can be made to, for example, "Radioimmunoassay" edited by Hiroshi Irie (Kodansha, published in 1974), "radioimmunoassay (sequel)" edited by Hiroshi Irie (Kodansha, published in 1979), "Enzyme Immunoassay" edited by Eiji Ishikawa et al. (the 3rd edition, Igaku-Shoin, published in 1987), "Methods in ENZYMOLOGY" Vol. 121 (Immunochemical Techniques (Part I: Hybridoma Technology and Monoclonal Antibodies)) (published by Academic Press) and the like.

As a specific detection (quantification) method of S38AA long fragment and S38AA short fragment, the amount of S38AA short fragment may be quantified by subtracting the measurement value of S38AA long fragment sample obtained using an "antibody that recognizes N-terminal side region of S38AA long fragment" alone, or an "antibody that recognizes N-terminal side region of S38AA long fragment" and an "antibody that recognizes C-terminal side region of S38AA long fragment" in combination from the measurement values of S38AA long fragment and S38AA short fragment in a sample, which are obtained using an "antibody that recognizes the C-terminal side region common to S38AA long fragment and S38A short fragment", or a measurement value obtained by a similar method may be quantified as a ratio of the amount of S38AA short fragment to the amount of S38AA long fragment, or the amount of S38AA short fragment may be directly quantified using the "antibody that specifically recognizes S38AA short fragment" of the present invention. Examples of the anti-S38AA long fragment antibody and anti-S38AA short fragment antibody capable of specifically detecting S38AA long fragment and S38AA short fragment include the antibodies described in detail in "2. Antibody of the present invention".

As used herein, the "antibody that recognizes the C-terminal side region common to S38AA long fragment and S38A short fragment" is preferably antibody A, B, or C.

As the "antibody that recognizes the N-terminal side region of S38AA long fragment" is preferably "an antibody for long fragment".

The "antibody that recognizes the C-terminal side region of S38AA long fragment" is preferably antibody A, B, or C.

The "antibody that specifically recognizes S38AA short fragment" is preferably antibody A, B, or C.

As the measurement method in the present invention, for example, "Long ELISA" can be mentioned. The "Long ELISA" is a method for detecting (quantifying) the amount of S38AA long fragment, and is characteristically sandwich ELISA method using an "antibody for long fragment", and "at least one antibody selected from the group consisting of antibodies A, B and C".

As the measurement method in the present invention, for example, "Total ELISA" can be mentioned. The "Total ELISA" is a method for detecting (quantifying) "the total amount of S38AA long fragment and S38AA short fragment", and is characteristically sandwich ELISA method using "at least two antibodies selected from the group consisting of antibodies A, B and C".

As a "method for detecting (quantifying) the amount of S38AA short fragment" in the present invention, a method including subtracting "measurement results (quantified values) of Long ELISA" from the above-mentioned "measurement results (quantified values) of Total ELISA" can be mentioned.

As the "control value" used in the method of the present invention, the amount of S38AA short fragment in the control sample, or the amount of S38AA short fragment measured or set in advance for the control or the like may be used. It is not necessary to measure the value simultaneously with the method of the present invention.

To set the control value here, it is also possible to use a plurality of individuals as a control group and mean of the measurement values of the plurality of individuals as the control value. That is, the above-mentioned determination and the like performed using, as the control value, the amount of S38AA short fragment in the control sample derived from the control group (healthy animal, animal affected with Alzheimer's disease in specific degree of progression, etc.) is also encompassed in the scope of the method of the present invention.

For example, when a sample derived from a healthy animal is used as a control sample, it can be judged or determined that a person is affected with Alzheimer's disease or has a high possibility of being affected with Alzheimer's disease at present, or has the possibility of being affected with Alzheimer's disease in the future.

Also, when a sample derived from an animal affected with Alzheimer's disease in a specific degree of progression is used as a control sample, it can be judged or determined that the degree of progression of Alzheimer's disease is higher than that of a control animal affected with the disease when the amount of S38AA short fragment in the test sample is higher than the amount in the control sample.

Furthermore, when a sample collected in the past from a test animal from which test samples were collected is used as the control sample, it can be determined that Alzheimer's disease is progressing when the amount of S38AA short fragment in the test sample is higher than the amount in the control sample, and that the disease is improving when the amount is lower than the amount in the control sample.

Moreover, using a plurality of control samples such as a control sample derived from an animal with Alzheimer's disease, a control sample derived from a healthy animal, and the like, it is possible to determine people at risk of Alzheimer's disease, that is, people in whom accumulation of Aβ and tau protein has started and Alzheimer's disease is highly likely developed in the near future, even though the onset of the disease cannot be diagnosed definitely, by using the index that the amount of S38AA short fragment in the test sample is larger than that of the control sample derived from a healthy animal and smaller than that of the control sample derived from an animal with Alzheimer's disease.

In addition, using, as a control sample, a sample collected in the past from a test animal from which test samples were collected and for which a medication treatment of Alzheimer's disease has started, it can be evaluated that the current medication treatment is not effective when the amount of S38AA short fragment in the test sample is higher than the amount in the control sample, and that the medication treatment is effective when the amount is lower than the amount in the control sample.

When "the polypeptide of SEQ ID NO: 1 in a sample collected from a test animal" is larger than "the amount of polypeptide (control value) of SEQ ID NO: 1 in a sample collected from a healthy animal", the possibility that a test animal is affected with Alzheimer's disease at present or the animal may be affected with Alzheimer's disease in the future can be determined.

The amount of the "polypeptide of SEQ ID NO: 1 in a sample collected from a test animal" is preferably 1.1 to 10 times the control value. It is more preferably 1.1 to 8 times the control value. It is further preferably 1.2 to 5 times the control value. It is most preferably 1.2 to 3 times the control value.

When "the polypeptide of SEQ ID NO: 1 in a sample collected from a test animal" is larger than "the amount of aforementioned polypeptide (control value) in a sample collected in the past from a test animal", it can be determined that Alzheimer's disease in the test animal is progressing.

The amount of the "polypeptide of SEQ ID NO: 1 in a sample collected from a test animal" is preferably 1.1 to 10 times the control value. It is more preferably 1.1 to 8 times the control value. It is further preferably 1.2 to 5 times the control value. It is most preferably 1.2 to 3 times the control value.

When "the polypeptide of SEQ ID NO: 1 in a sample collected from a test animal" is smaller than "the amount of aforementioned polypeptide (control value) in a sample collected in the past from a test animal", it can be determined that Alzheimer's disease in the test animal is improving.

The amount of the "polypeptide of SEQ ID NO: 1 in a sample collected from a test animal" is preferably 0.1 to 0.9 times the control value. It is more preferably 0.2 to 0.9 times the control value. It is further preferably 0.3 to 0.9 times the control value. It is most preferably 0.4 to 0.9 times the control value.

Quantitative analysis of S38AA short fragment may be performed by standardizing the amount of S38AA short fragment in the sample by the amount of standard protein (internal standard protein). That is, after quantifying the amount of S38AA short fragment and the amount of standard protein in the sample by using the above-mentioned method, the ratio of the signals of the both (S38AA short fragment/standard protein) is calculated, and the amount of S38AA short fragment in the sample may be expressed as a ratio to the abundance of the standard protein.

The standard protein may be a protein that is constitutively expressed in a given amount, and a protein that is commonly expressed in many tissues and cells is preferable. For example, proteins essential for cell survival, such as proteins encoded by genes such as RNA synthase, energy-generating enzyme, ribosome protein, cellular skeleton protein and the like (housekeeping genes) can be mentioned. Specific examples thereof include, but are not limited to, proteins such as β-actin, glyceraldehyde-3-phosphate dehydrogenase (GAPDH), β-tubulin and the like. Particularly preferred is β-actin.

In addition, instead of the aforementioned control value, a cutoff value of the amount of S38AA short fragment in blood, which relates to Alzheimer's disease or mild cognitive impairment, may be set in advance, and the amount of S38AA short fragment in the blood of the test animal may be compared with the cutoff value.

For example, when the amount of the S38AA short fragment in the blood of a test animal is not less than the cutoff value, it can be determined that the test animal is affected with Alzheimer's disease, or may be affected with Alzheimer's disease at present or may be affected with Alzheimer's disease in the future.

The "cutoff value" is a value that can satisfy both high diagnostic sensitivity (true positive rate) and high diagnostic specificity (true negative rate) when a disease is determined using the value as the standard. For example, a value showing a high positive rate in an individual who has developed Alzheimer's disease and a high negative rate in an individual who has not developed Alzheimer's disease can be set as a cutoff value.

The method for calculating the cutoff value is well known in the art. For example, the amounts of S38AA short fragment in blood in an individual who developed Alzheimer's disease and an individual who has not developed Alzheimer's disease are calculated, and the diagnostic sensitivity and diagnosis specificity of the calculated values are obtained. Based on these values, a ROC (Receiver Operating Characteristic) curve is created using commercially available analysis software. Then, a value at which the diagnostic sensitivity and the diagnosis specificity are as close to 100% as possible is obtained, and the value can be used as the cutoff value. In addition, for example, it is preferable to set the "mean+2 standard deviation" of the amount of S38AA short fragment in blood of a large number of healthy animals as the cutoff value. Using this value, it can be determined with good sensitivity and specificity that Alzheimer's disease is developed. Furthermore, for example, it is possible to determine Alzheimer's disease with high sensitivity by obtaining a value that maximizes the likelihood ratio between the diagnostic sensitivity and the diagnosis specificity from the ROC curve and using the value as the cutoff value. Alternatively, a point with the lowest diagnosis ability on the ROC curve, that is, a point most distant from the line where the area under the ROC curve is 0.5, is set as the cutoff value, that is, "sensitivity+specificity −1" is calculated, and a point at which the value becomes the maximum value is preferably set as the cutoff value.

A cutoff value of the amount of S38AA short fragment converted with the recombinant protein of the present specification is, for example, 45-75 units. The cutoff value is preferably, for example, 49-69 units. The cutoff value is more preferably, for example, 54-64 units. The cutoff value is more preferably, for example, 56-62 units. The cutoff value is further preferably, for example, 58-61 units. The cutoff value is most preferably, for example, 59 units.

Another preferable value of the cutoff value includes 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75 units.

A cutoff value of the amount of S38AA short fragment contained in the body is, for example, 45-75 ng/mL. The cutoff value is preferably, for example, 49-69 ng/mL. The cutoff value is more preferably, for example, 54-64 ng/mL. The cutoff value is more preferably, for example, 56-62 ng/mL. The cutoff value is further preferably, for example, 58-61 ng/mL. The cutoff value is most preferably, for example, 59 ng/mL.

Another preferable value of the cutoff value includes 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75 ng/mL.

When determining Alzheimer's disease by the method of the present invention, changes in other diagnostic markers for Alzheimer's disease may be examined in addition to the S38AA short fragment. Other diagnostic markers for Alzheimer's disease include, for example, known markers such as Aβ whose potential as plasma biomarker has been studied, homocysteine, neurofilament, various inflammation-related proteins (C-reactive protein, IL-1β, TNF, IL-6 and TGFβ), cholesterol, tau, phosphorylated tau, and the like. These can be detected according to a conventional well-known detection method.

(2) Method for Treating and Preventing Alzheimer's Disease

When the above-mentioned method for determining Alzheimer's disease of the present invention and the like determine that a test animal is affected with Alzheimer's disease, or may be affected with Alzheimer's disease at present or may be affected with Alzheimer's disease in the future, Alzheimer's disease can be treated or prevented by determining, based on the results, a therapeutic or prophylactic drug for Alzheimer's disease to be administered to the test animal, and administering a therapeutically effective amount of the therapeutic or prophylactic drug to the test animal.

In the present specification, the "therapeutic drug for Alzheimer's disease" includes not only a medicament aiming at permanent cure treatment of Alzheimer's disease but also, for example, a medicament aiming at suppressing the progression of Alzheimer's disease. The medicament aiming at suppressing the progression may be used as an "Alzheimer's disease prophylactic drug".

Examples of the therapeutic drug for Alzheimer's disease include cholinesterase inhibitors, NMDA receptor antagonist, amyloid β remover and production inhibitor, and tau protein remover and production inhibitor.

Examples of the cholinesterase inhibitor include donepezil, galanthamine, rivastigmine, Huperzine A, and tacrine.

Examples of the NMDA receptor antagonist include memantine.

Examples of the amyloid β remover and production inhibitor include amyloid β vaccine, amyloid β removing antibody, amyloid β production enzyme inhibitor, amyloid β coagulation inhibitor and amyloid β degradation promoter. Specific examples include CNP-520, E-2609, aducanumab, solanezumab, gantenerumab, crenezumab, amilomotide, ASD-005, HSH-971, ELND-005, ALZT-OP1, nilvadipine, ACI-24, UB-311, AFFITOPE AD-02, LY-3002813, BAN-2401, Neurostem-AD, CT-1812, ID-1201, NIC5-15, BI-425809, Posiphen, PQ-912, bryostatin-1, Apabetalone, PBT-2, RIV-1061-IR, MEDI-1814, PF-05236812, SAR-228810, Lu-AF20513, PRI-002, IRX-4204, GC-021109, AAD-2004, CTS-21166, LY-3323795, benfotiamine, bisnorcymserine, MDR-1339, KHK-6640, and NPT-088.

Examples of the tau protein remover and production inhibitor include tau protein vaccine, tau protein removing antibody, tau protein modification inhibitor, tau protein coagulation inhibitor, and tau proteolysis promoter. Specific examples include TRx-237, TPI-287, ABBV-8E12, RG-6100, AADvac1, RO7105705, PTI-80, JNJ-63733657, UCB-0107, BIIB-076, MC-1, ACI-35, and AZP-2006.

The above-mentioned therapeutic drugs may be used in appropriate combinations according to the symptoms of the patients.

6. Therapeutic Drug of the Present Invention

The above-mentioned therapeutic drugs for Alzheimer that can be used vary depending on the severity of the symptoms (mild, moderate, severe etc.). Therefore, the therapeutic drug to be administered to the test animal may be determined using the determined results of the method for assisting in the determination of the degree of progression of Alzheimer's disease of the present invention described above. Therefore, the present invention provides a therapeutic drug for Alzheimer's disease that is used for a test animal (patient) whose degree of progression of Alzheimer's disease has been determined.

As mentioned above, the amount of S38AA short fragment markedly increases in the blood of AD patients, and a positive correlation exists between the amount of S38AA long fragment in blood and the severity of Alzheimer's disease (progression of cognitive dysfunction). Thus, the present invention provides a therapeutic or prophylactic drug for Alzheimer's disease that contains, as an active ingredient, a medicament that decreases the amount of S38AA short fragment in the body of patients with Alzheimer's disease or one (human) who may be affected with Alzheimer's disease, or a medicament that inhibits production of S38AA short fragment in the body of patients with Alzheimer's disease or one (human) who may be affected with Alzheimer's disease. As used herein, the amount of S38AA short fragment in the body of a patient with Alzheimer's disease or one who may be affected is, for example, the amount of S38AA short fragment contained in a biological tissue or body fluid of the patient or one who may be affected. Specifically, blood, cerebrospinal fluid, urine, saliva, lacrimal fluid and the like can be mentioned.

The medicament that decreases the amount of S38AA short fragment is, for example, a neutralizing antibody, and it can decrease free S38AA short fragment in the body by binding to the S38AA short fragment in the body of a patient or one who may be affected. The medicament that inhibits production of S38AA short fragment is, for example, an inhibitor of enzyme that produces 38AA short fragment by cleaving S38AA long fragment, and each of them can be obtained by methods known to those skilled in the art.

7. Method for Screening for Candidate Substance for Therapeutic or Prophylactic Drug for Alzheimer's Disease The present invention provides a method for selecting a candidate substance for a therapeutic or prophylactic drug for Alzheimer's disease by using whether or not a test substance removes S38AA short fragment or whether or not it inhibits the production of S38AA short fragment as an index, and a substance obtained by the method. In the screening method of the present invention, a substance that decreases the amount of an S38AA short fragment in blood, or down-regulates the production of an S38AA short fragment is selected as a candidate substance for a therapeutic or prophylactic drug for Alzheimer's disease.

The test substance to be subjected to the screening method of the present invention may be any known or novel compound. Examples thereof include nucleic acid, carbohydrate, lipid, protein, peptide, organic low-molecular-weight compound, compound library produced using a combinatorial chemistry technique, random peptide library, natural component derived from microorganism, animals and plants, marine organism etc., and the like.

For example, the screening method of the present invention may include:
(i) a step of contacting a test substance with a cell permitting measurement of production of a S38AA short fragment;
(ii) a step of measuring the production amount of the S38AA short fragment in the cell contacted with the test substance, and comparing the production amount with that of the S38AA short fragment in a control cell free of contact with the test substance; and (iii) a step of selecting a test substance that down-regulates the production amount of the S38AA short fragment as a candidate substance for a therapeutic or prophylactic drug for Alzheimer's disease, based on the comparison results of the above-mentioned (ii).

In addition, the screening method of the present invention may include:
(i) a step of contacting a test substance with an enzyme that forms an S38AA short fragment; (ii) a step of measuring the production amount of the S38AA short fragment in the enzyme contacted with the test substance, and comparing the production amount with that of the S38AA short fragment in a control enzyme free of contact with the test substance; and (iii) a step of selecting a test substance that down-regulates the production amount of the S38AA short fragment as a candidate substance for a therapeutic or prophylactic drug for Alzheimer's disease, based on the comparison results of the above-mentioned (ii). The above-mentioned enzyme substrate is not particularly limited as long as it produces S38AA short fragment and, for example, S38AA, S38AA long fragment, S38AA fragment and the like can be mentioned.

Furthermore, for example, (i) a step of contacting a test substance with a S38AA short fragment, (ii) a step of measuring the amount of free S38AA short fragment remaining after contact with the test substance, and comparing the amount with that of the free S38AA short fragment when the free S38AA short fragment is not contacted with the test substance, and (iii) a step of selecting a test substance that down-regulates the amount of the free S38AA short fragment by binding to S38AA short fragment as a candidate substance for a therapeutic or prophylactic drug for Alzheimer's disease, based on the comparison results of the above-mentioned (ii) may be included. The method may be performed by adding a test substance to a system containing an enzyme and a substrate thereof that produce the above-mentioned S38AA short fragment, or by adding a test substance to a system containing S38AA short fragment prepared in advance. Alternatively, in (i) a step of contacting a test substance with a S38AA short fragment, the S38AA short fragment may form sediments (e.g., immunoprecipitation, etc.) due to the contact.

The "cell" to be used for the screening method of the present invention means a cell permitting evaluation of the production level of the measurement target, an S38AA short fragment. Examples of the cell include a cell capable of naturally producing the S38AA short fragment of the measurement target, an S38AA-expressing cell capable of producing an S38AA short fragment by stimulation, and a genetically engineered cell to be able to produce an S38AA short fragment.

The cell capable of naturally producing an S38AA short fragment, is not particularly limited and, as such cell, a primary cultured cell of a mammal (for example, human, mouse etc.), a cell line induced from said primary cultured cell and the like can be used. S38AA is known to be expressed in U251 cell and SHSY-5Y cell, and also expressed in BE(2)-C cell and SK-N-MC cell. In addition, a genetically engineered cell overexpressing S38AA or labeled S38AA with FLAG tag etc., and the like can also be produced using a known technique. By culture, S38AA is cleaved from the S38AA expressing cell and the S38AA short fragment is liberated. When the amount of the produced S38AA short fragment is small, the production of the S38AA short fragment can be measured by cultivating, as appropriate, under conditions easily causing the cleavage of S38AA. Examples of the conditions easily causing the cleavage of S38AA include cultivating in a glucose depletion medium or a medium containing a substance known to physiologically stimulate the brain. Specific examples of such substance include cytokines such as TNFα, interferon-γ, interleukin-1, interleukin-6 and the like, amyloid beta or aggregate thereof and the like.

The test substance and the cell permitting measurement of the production of an S38AA short fragment are contacted in a culture medium. The culture medium is appropriately selected according to the cell permitting measurement of the production of an S38AA short fragment. Examples thereof include minimum essential medium (MEM), Dulbecco's modified Eagle medium (DMEM), containing about 5-20% of fetal bovine serum, and the like. The culture conditions are appropriately determined in the same manner. For example, the pH of the medium is about 6-about 8, the culture temperature is generally about 30-about 40° C., and the culture time is about 0.1-about 72 hr.

The contact between the test substance and an enzyme that forms S38AA short fragment is carried out in a reaction system containing the enzyme and a substrate thereof. The enzyme concentration, substrate concentration, pH, temperature, and the like of the reaction system, and enzyme substrate, reaction time and the like can be set as appropriate.

As used herein, as the enzyme that produces S38AA short fragment, a solution containing the enzyme can be used. Examples of the solution include body fluid (plasma, etc.), organ or tissue extract, cell extract, and the like that can form S38AA short fragment.

The production amount of the S38AA short fragment can be measured by measuring the amount of the S38AA short fragment liberated in the cell culture supernatant or in the reaction system according to the method described in the item of (5. Method of the present invention).

The production amount can be preferably compared based on the presence or absence of a significant difference. The production amount of an S38AA short fragment in the control cell or enzyme free of contact with the test substance may be measured before or simultaneously with the measurement of the production amount of the S38AA short fragment in the cell or enzyme contacted with the test substance.

The substance obtained by the screening method of the present invention is useful as a candidate substance for the development of a new therapeutic or preventive drug for Alzheimer's disease.

EXAMPLE

The present invention is explained in detail in the following by referring to Examples; however, the present invention is not limited thereto.

Example 1: Identification of N-Terminal Cleavage Site of S38AA Long Fragment in Human Plasma After separating plasma proteins derived from AD patients by polyacrylamide gel electrophoresis (SDS-PAGE), gel fragments containing S38AA fragments were cut out and, after in-gel digestion with trypsin, and analyzed by liquid chromatography-mass spectrometry (LC-MS/MS). The measurement data was subjected to MASCOT database search, and the N-terminal sequence of the S38AA fragment was determined.

Specifically, a mixed sample of the plasma of some AD patients was applied to 4-12% Bis-Tris Gel (invitrogen), and protein was separated by SDS-PAGE (25 mA, 110 min, MOPS buffer). After staining the gel with Coomassie Brilliant Blue staining, the band seen at 80-100 kDa was cut out and applied to the digestion process.

The cut gel fragments were placed in a 96-well microplate, acetonitrile was added, the mixture was centrifuged under reduced pressure, 10 mM DTT/100 mM $NH_4HCO_3$ was added, and incubation was performed. After removing the solvent, 55 mM $ICH_2CONH_2$/100 mM $NH_4HCO_3$ was added and the mixture was incubated. After removing the solvent, 100 mM $NH_4HCO_3$ was added, the gel was centrifuged under reduced pressure, 0.1% RapiGest/25 mM $NH_4HCO_3$ was added, and incubation was performed. Then, the mixture was centrifugally dried under reduced pressure, an enzyme solution (50 mM $NH_4HCO_3$, 12.5 ng/μL trypsin) was added, and enzyme digestion was performed. After the reaction, the peptide solution was transferred to another 96-well microplate, a mixed solvent of acetonitrile:milliQ:trifluoroacetic acid (TFA)=500:500:1 was added to the gel, and the obtained peptide extract was concentrated under reduced pressure. TFA was added thereto, and the mixture was concentrated under reduced pressure to give a sample for MS analysis.

The obtained sample was analyzed by LC-MS/MS. When the data obtained by the Orbitrap mass spectrometer was subjected to MASCOT database search for the amino acid sequence of S38AA protein, multiple peptide fragments were identified in the amino acid sequence of the S38AA protein (FIG. 1). Of these sequences, the peptide which is closest to the N-terminal side is the 399th to 413th amino acid sequence, and an MS/MS spectrum showing the sequence was observed (FIG. 2). This cleavage site was on the C-terminal side of the 398th serine (S). As for the cleavage of digestive enzyme trypsin, since the enzyme specifically cleaves the C-terminal of lysine (K) or arginine (R), and the cleavage reaction does not occur on the C-terminal side of serine (S) of the fragment, the cleavage having already been performed at this site was suggested. The detection of the peptide fragment revealed that the N-terminal side of the purified S38AA fragment was cleaved at the 398th to 399th S/E. The S38AA fragment identified here is referred to as S38AA long fragment.

Example 2: Identification of N-Terminal Cleavage Site of S38AA Short Fragment in Human Plasma After removing S38AA long fragment by immunoprecipitation method using rabbit-derived anti-S38AA polyclonal antibody that recognizes the N-terminal of S38AA Long fragment (to be also referred to as "MBL", "antibody for S38AA long fragment", or "antibody for long fragment"), remaining S38AA fragments were immunoprecipitated using mouse-derived anti-S38AA monoclonal antibody A (antibody-producing hybridoma was established using a part of the peptide of the C-terminal amino acid sequence of S38AA fragment as an immunogen, and separated and purified; antibody A), mouse-derived anti-S38AA monoclonal antibody B (antibody-producing hybridoma was established using a part of the peptide of the C-terminal amino acid sequence of S38AA fragment as an immunogen, and separated and purified; antibody B), or mouse-derived anti-S38AA monoclonal antibody C (antibody-producing hybridoma was established using recombinant protein of S38AA long fragment in *Escherichia coli* as immunogen, and separated and purified; antibody C), fractions thereof were purified by reverse-phase column, digested with trypsin, analyzed by LC-MS/MS, and the N-terminal sequence of the S38AA fragment was determined.

Specifically, to a pooled mixture of the plasma of AD patients was added PBS containing a protease inhibitor (cOmplete Tablets Mini, Roche), and Protein G Mag Sepharose Xtra (bead, GE HEALTHCARE) was further added and mixed to remove endogenous immunoglobulins. Antibody for long fragment was added to the supernatant after removal of beads, and antigen-antibody reaction was performed. After mixing, beads were newly added, and recovery protein containing antibody for long fragment and S38AA long fragment adsorbed to the antibody was removed. To the supernatant after removal of beads was added the aforementioned antibody A, B or C, and antigen-antibody reaction was performed. After mixing, beads were newly added, and the beads were collected to obtain the antibody and the S38AA fragment adsorbed on the antibody. An 8M urea/1% TFA solution was added to the beads recovered by immunoprecipitation, and the S38AA fragment was eluted. The obtained solution containing the S38AA fragment was concentrated, and the total amount was separated by reverse-phase column (ZORBAX 300SB-C3, 4.6× 150 mm with guard column, Agilent). The separation conditions are as shown in Table 1 below. The obtained each fraction was measured by sandwich ELISA using two antibodies recognizing the C-terminal side region of the S38AA fragment, fractions containing S38AA fragment were digested with an enzyme solution (1M $NH_4HCO_3$, 10 mM $CaCl_2$, 1 ng/μL trypsin), and the obtained peptide was concentrated with GL-tip SDB and GL-Tip GC (GL Sciences).

The obtained peptide was analyzed by LC-MS/MS. When the data obtained by the Q-Exactive HF mass spectrometer was subjected to MASCOT database search for the amino acid sequence of S38AA protein, S38AA was identified with the highest score and multiple peptide fragments were identified (FIG. 3). Of these sequences, the peptide which is the closest to the N-terminal side is the 617th to 627th sequence, and an MS/MS spectrum showing the sequence was observed (FIG. 4). This cleavage site was on the C-terminal side of the 616th asparagine (N). As for the cleavage of digestive enzyme trypsin, since the enzyme specifically cleaves the C-terminal of lysine (K) or arginine (R), and the cleavage reaction does not occur on the C-terminal side of asparagine (N) of the fragment, the cleavage having already been performed at this site was shown. The detection of the peptide fragment revealed that the purified S38AA fragment was cleaved at the 617th to 618th N/G. The S38AA fragment identified here is referred to as S38AA short fragment.

TABLE 1

| reverse-phase column purification separation conditions | | |
|---|---|---|
| Flow 1 ml/min | | Temp 70 |
| A: 0.1% TFA/$H_2O$ B: 0.1% TFA/acetonitrile | | |
| | min | % B |
| gradient conditions | 0 | 20 |
| | 40 | 80 |
| | 41 | 95 |
| | 46 | 95 |
| | 47 | 20 |
| | 57 | 20 |

Example 3: Identification of C-Terminal Cleavage Site of S38AA Long Fragment in Human Plasma S38AA long fragment was separated by the antibody column purification method using "polyclonal antibody for rabbit-derived S38AA long fragment (antibody for long fragment)" used in Example 2, gel fragments containing S38AA long fragments were cut out and, after in-gel digestion with trypsin, analyzed by LC-MS/MS. The measurement data was subjected to MASCOT database search, and the C-terminal fragment sequence of the S38AA long fragment was determined.

Specifically, to a mixed sample of the plasma of some AD patients was added 50 mM Tris-HCl/0.05% Tween-20 (pH 7.4), and the mixture was applied to anion exchange column purification (Hitrap Q FF, GE HEALTHCARE). Successively, it was eluted with 50 mM phosphoric acid/0.05% Tween-20/500 mM NaCl (pH 7.4). The eluted fraction was applied to a column (HiTrap NHS-activated HP column, GE HEALTHCARE) bound with antibody for long fragment. The column was washed with PBS-T, and eluted with 0.1 M Glycine-HCl/0.05% Tween-20 (pH2.7). The eluate was immediately returned to neutral with 1M Tris-HCl (pH9.0). The obtained sample was applied to HiTrap Q FF column (GE HEALTHCARE) equilibrated in advance with 50 mM Tris-HCl (pH 7.4), and the surfactant was removed. The sample was concentrated by centrifugation under reduced pressure, 50 mM DTT/LDS buffer was added, and the mixture was heated. The total amount of the sample was applied to 4-12% Bis-Tris Gel (Invitrogen), and protein was separated by SDS-PAGE (50 mA, 90 min, MOPS buffer). After staining the gel with Sypro Ruby (pierce), the band seen at 80-100 kDa was cut out and applied to the digestion process.

The cut gels were placed in a 96-well microplate, acetonitrile was added, and sonication was performed. Thereafter, the mixture was centrifugally dried under reduced pressure, 10 mM DTT/25 mM $NH_4HCO_3$ was added, and incubation was performed. After removing the solvent, 55 mM $ICH_2CONH_2$/25 mM $NH_4HCO_3$ was added, and incubation was performed under shading. After removing the solvent, 50 mM $NH_4HCO_3$ was added, the mixture was incubated, acetonitrile was added, and sonication was performed. After removing the solvent, the gel was centrifugally dried under reduced pressure, 0.1% RapiGest/25 mM $NH_4HCO_3$ was added, and incubation was performed. Thereafter, the mixture was centrifugally dried under reduced pressure, incubation was performed, an enzyme solution (50 mM $NH_4HCO_3$, 5 ng/µL trypsin) was added, and the mixture was incubated. After removing the solvent, 50 mM $NH_4HCO_3$ was added, the mixture was incubated, and enzyme digestion was performed. After the reaction, the peptide solution was transferred to another 96-well microplate, a mixed solvent of acetonitrile:milliQ:TFA=500:500:1 was added to the gel, and sonication was performed. This operation was repeated again, and the obtained peptide extract was concentrated under reduced pressure to give a sample for MS analysis.

The obtained peptide was analyzed by LC-MS/MS. When the data obtained by the Orbitrap mass spectrometer was subjected to MASCOT database search for the amino acid sequence of S38AA protein, multiple peptide fragments were identified in the amino acid sequence of the S38AA protein (FIG. 5). Of these sequences, the peptide which is the closest to the C-terminal side is the 1040th to 1049th sequence, and an MS/MS spectrum showing the sequence was observed (FIG. 6). This cleavage site was on the C-terminal side of the 1049th leucine (L). As for the cleavage of digestive enzyme trypsin, since the enzyme specifically cleaves the C-terminal of lysine (K) or arginine (R), and the cleavage reaction does not occur on the C-terminal side of leucine (L) of the fragment, the cleavage having already been performed at this site was suggested. The detection of the peptide fragment revealed that the C-terminal of S38AA long fragment was cleaved at the 1049th to 1050th L/R. Since the S38AA short fragment had the same reactivity to the "antibody (antibody A, antibody B, or antibody C) that recognizes the C-terminal of the S38AA long fragment" used in Example 2, it was considered that the C-terminal of the S38AA short fragment was also cleaved at the same site.

Example 4: Production of Recombinant Proteins of S38AA Long Fragment and S38AA Short Fragment in *Escherichia coli* and Measurement of them by ELISA Recombinant proteins in *Escherichia coli* of S38AA long fragment and S38AA short fragment were produced. Using them as the reference standard, Long ELISA that quantifies only S38AA long fragment and Total ELISA that quantifies both fragments were constructed.

Specifically, a transformant of *Escherichia coli* BL21 (DE3) into which plasmid DNAs of S38AA long fragment sequence (399-1049 amino acid sequence) and S38AA short fragment sequence (617-1049 amino acid sequence) were introduced was produced. Shaking culture was continued, and the cells were harvested by centrifugation. A protein extraction reagent B-PER (Thermo Fisher Scientific) was suspended in a small amount of bacterial bodies, the centrifugation supernatant was electrophoresed by SDS-PAGE, and the expression of the targeted protein was confirmed. The bacterial bodies were suspended in buffer A (20 mM Tris HCl pH 8.0, 200 mM NaCl, 10% glycerol, 20 mM imidazole), protease inhibitor cOmplete EDTA-free (Roche), and nuclease Benzonase to disrupt the bacterial bodies, and the suspension was centrifuged. Using a 0.22 µm filter, residual bacterial bodies were removed from the centrifugation supernatant, and Ni affinity purification was performed using HisTrap HP. Elution fractions of the object protein were brought together and used as the reference standard. The protein concentration of the reference standard was measured to fine 1.4 mg/mL (long fragment), and 1.6 mg/mL (short fragment), respectively.

Sandwich ELISA (Long ELISA) by "antibody that recognizes the N-terminal side region of S38AA long fragment (antibody for long fragment used in Example 2)", "antibody A that recognizes C-terminal side region", "antibody B", or "antibody C", and sandwich ELISA (Total ELISA) by two antibodies selected from "antibody A", "antibody B" and "antibody C" that recognizes the C-terminal side region common to both S38AA long fragment and S38AA short fragment were generated. As a reference standard for quantification, the above-mentioned recombinant protein in *Escherichia coli* (standard protein) was prepared and measured by the both ELISAs. The sample was applied to a plate on which each antibody was immobilized, and incubated. After washing 3 times, each HRP-labeled antibody was added and incubated. After washing three times, a 3% 3,3',5,5'-Tetramethylbenzidine (TMB) solution was added, and the mixture was incubated under shading. Finally, 8% sulfuric acid was added to discontinue the reaction, and the absorbance (O.D.) at 450 nm was measured. As a result, a standard protein concentration-dependent reaction was observed, and a good calibration curve was obtained (FIG. 7). In Long ELISA, no reaction to S38AA short fragment standard protein was observed.

Example 5: Quantification of S38AA Long Fragment and S38AA Short Fragment in Human Plasma (Total ELISA-Long ELISA Subtraction Method)

To quantify S38AA long fragment and S38AA short fragment contained in human plasma, quantification by ELISA using a subtraction method was performed.

Figure 8:
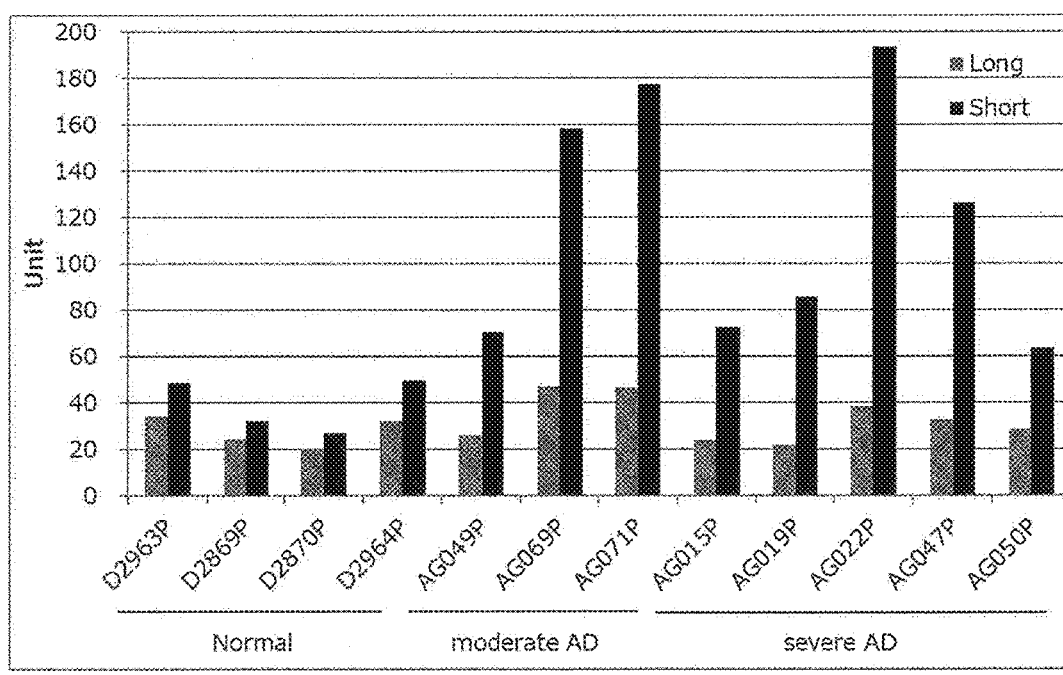
FIG. 8 shows the quantitative values in each sample when the S38AA long fragment and the S38AA short fragment in human plasma were quantified by the subtraction method. The vertical axis shows the quantitative values of S38AA long fragment and S38AA short fragment, and the horizontal axis shows each sample. Numbers starting with D indicate healthy individuals, and numbers starting with AG indicate patients with moderate and severe AD.

Specifically, the amount of S38AA short fragment contained in each plasma derived from 4 healthy subjects and 8 moderate and severe AD patients was quantified using the aforementioned Total ELISA and Long ELISA. Quantification was performed according to the method described in Example 4. The calibration curve of each ELISA was created by the measurement of S38AA long fragment standard protein. The amount of S38AA short fragment was calculated by subtracting the quantified value of Long ELISA from the quantified value of the Total ELISA. As a result, the quantified values of S38AA long fragment and S38AA short fragment in each sample were obtained (FIG. 8).

Figure 9:
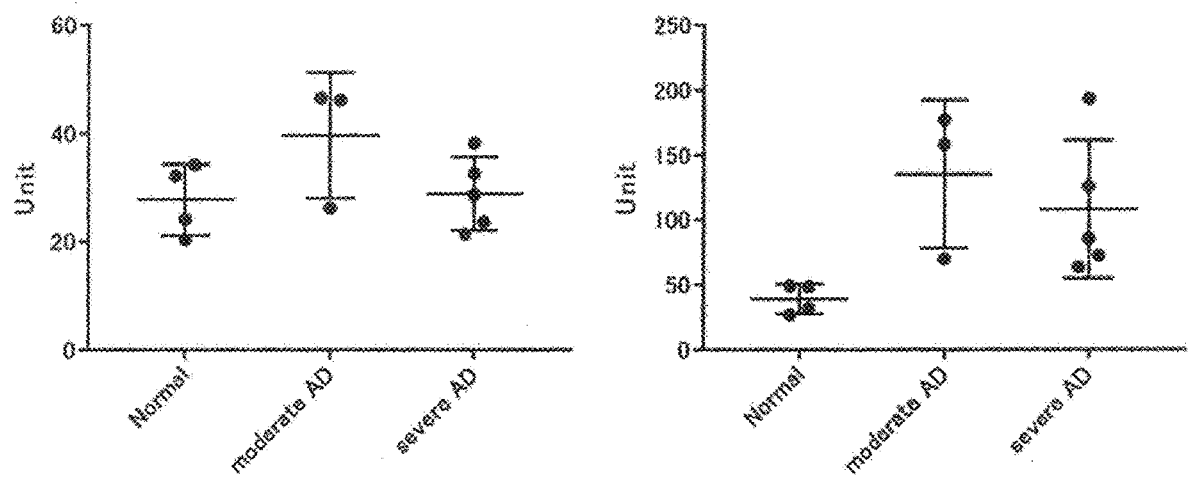
FIG. 9 shows the quantitative values in each group when the S38AA long fragment (left Figure) and the S38AA short fragment (right Figure) in human plasma were quantified by the subtraction method. The vertical axis shows the quantitative values of S38AA long fragment and S38AA short fragment, and the horizontal axis shows each group. Individual samples are shown in each plot. The graph bar shows (mean±standard deviation of each group).

Based on the obtained results, the amounts of S38AA short fragment and S38AA long fragment plasma derived from healthy human and AD patients were analyzed. As a result, it was found that the amount of S38AA short fragment is highly distinguishable between healthy subjects and AD patients, and can determine moderate and severe AD patients with high sensitivity compared to the amount of the S38AA long fragment (FIG. 9).

Example 6: Quantification of S38AA Long Fragment and S38AA Short Fragment in Human Plasma (Long Fragment Immunoprecipitation Removing Method)

To quantify S38AA long fragment and S38AA short fragment contained in human plasma, removal of S38AA long fragment using the immunoprecipitation method and ELISA quantification were performed.

Figure 10:
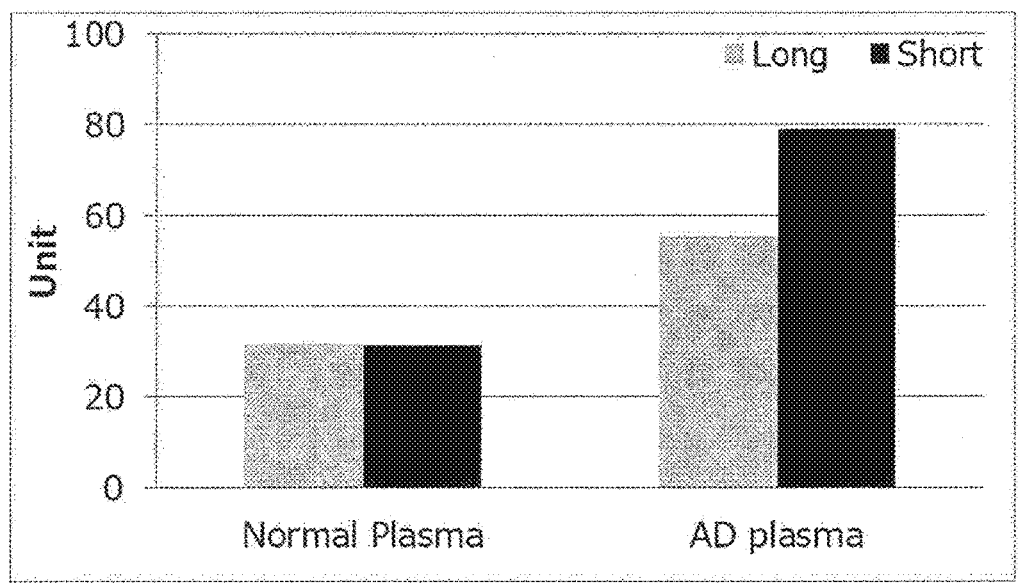
FIG. 10 shows the quantitative values in each group when the S38AA long fragment and the S38AA short fragment in human plasma were quantified by the immunoprecipitation removing method. The vertical axis shows the quantitative values of S38AA long fragment and S38AA short fragment, and the horizontal axis shows each group.

Specifically, PBS was added to each mixed sample of the plasma of some healthy subjects and AD patients, and Protein G Mag Sepharose Xtra (bead, GE HEALTHCARE) was further added and mixed to remove endogenous immunoglobulin. After the reaction, a polyclonal antibody for rabbit-derived S38AA long fragment (antibody for long fragment) was added to the supernatant, and antigen-antibody reaction was performed. After the reaction, the reaction solution was mixed with new beads, and the antigen-antibody complex was recovered on the beads. By adding 0.1M Gly-HCl (pH 2.8) to the recovered beads, the recovered protein containing S38AA long fragment was eluted. The eluate was immediately returned to neutral with 1M Tris-HCl (pH9.0). The amounts of the obtained eluate (S38AA long fragment fraction) and S38AA long fragment and S38AA short fragment contained in the supernatant (S38AA short fragment fraction) were each quantified by Total ELISA. Quantification was performed according to the method described in Example 4. The calibration curve of each ELISA was created by the measurement of S38AA long fragment standard protein. As a result, the quantified values of S38AA long fragment and S38AA short fragment in each sample were obtained (FIG. 10). From the results, it was suggested that the amount of S38AA short fragment was significantly increased in AD patients as compared with S38AA long fragment.

Example 7: Comparison of AD Diagnostic Performance by Quantification of Each S38AA Fragment (Total ELISA-Long ELISA Subtraction Method)

To compare the AD diagnostic performance by quantification of each S38AA fragment, ELISA quantification using the subtraction method was performed.

Figure 11:
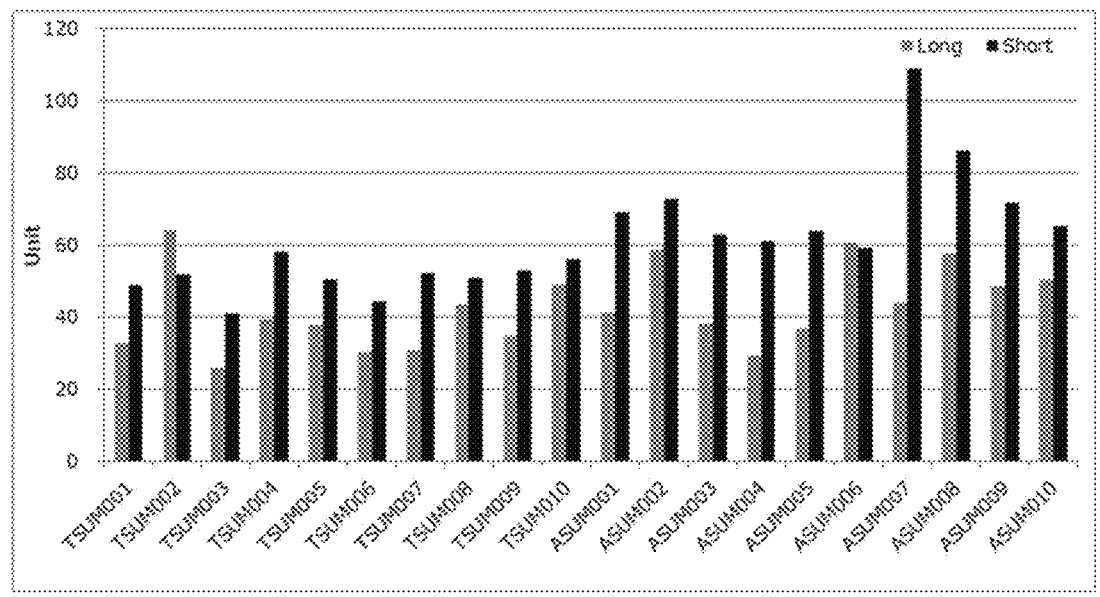
FIG. 11 shows the quantitative values in each sample when the S38AA long fragment and the S38AA short fragment in human plasma were quantified by the subtraction method. The vertical axis shows the quantitative values of S38AA long fragment and S38AA short fragment, and the horizontal axis shows each sample. Numbers starting with TSUM indicate healthy individuals, and numbers starting with ASUM indicate patients with mild AD.
Figure 12:
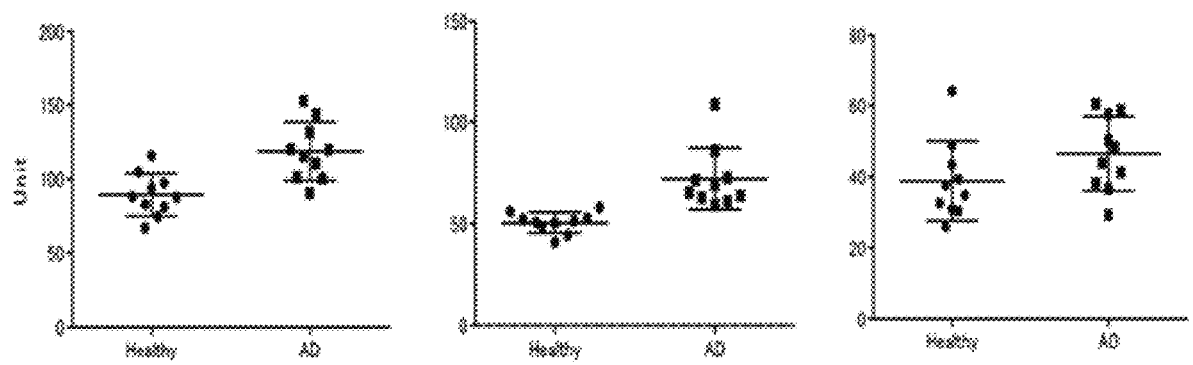
FIG. 12 shows the quantitative values in each group when the S38AA long fragment and S38AA short fragment (left Figure), S38AA short fragment (middle Figure) S38AA long fragment (right Figure) in human plasma were quantified by the subtraction method. The vertical axis shows the quantitative values of S38AA long fragment and S38AA short fragment, and the horizontal axis shows each group. Individual samples are shown in each plot. The graph bar shows (mean±standard deviation of each group).
Figure 13:
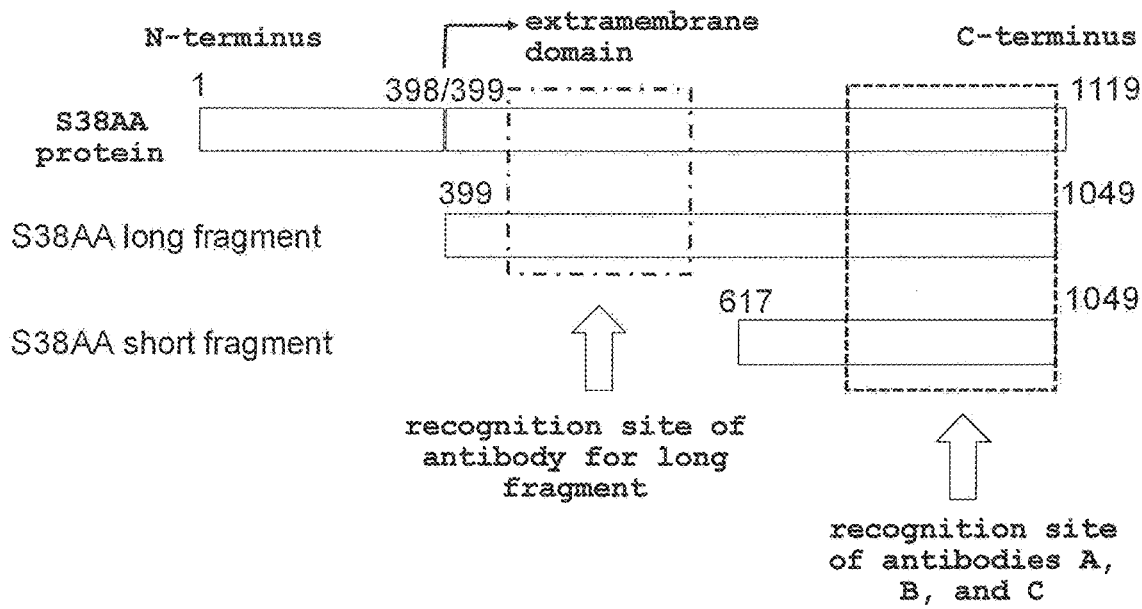
FIG. 13 shows recognition sites of antibody for long fragment, antibody A, antibody B and antibody C.

Specifically, the amount of S38AA short fragment and the amount of S38AA long fragment contained in each plasma derived from 10 healthy subjects and 10 mild AD patients were quantified using Total ELISA and Long ELISA. Quantification was performed according to the method described in Example 4. The calibration curve of each ELISA was created by the measurement of S38AA long fragment standard protein. The amount of S38AA short fragment was calculated by subtracting the quantified value of Long ELISA from the quantified value of the Total ELISA. As a result, the quantified values of S38AA long fragment and S38AA short fragment in each sample were obtained (FIG. 11). In addition, it was suggested that mild AD can be diagnosed with high sensitivity by quantifying only the amount of S38AA short fragment compared to the total amount or the amount of S38AA long fragment (FIG. 12).

Example 8: Quantification of S38AA Fragment in Human Plasma by Combining Various Anti-S38AA Fragment Antibodies—1

To quantify "the total amount of "the amount of S38AA short fragment" and "the amount of S38AA long fragment"" contained in human plasma, ELISA quantification using various anti-S38AA fragment antibodies in combination was performed.

Figure 14:
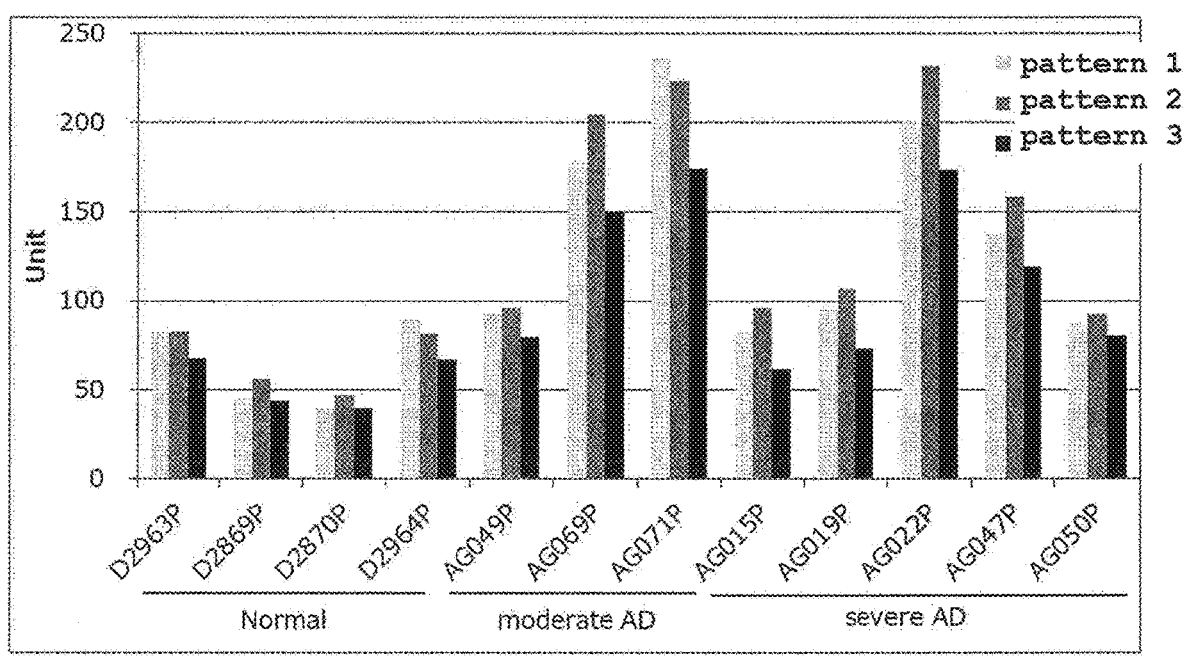
FIG. 14 shows the quantitative values in each sample when S38AA fragment in human plasma is quantified by combining various anti-S38AA fragment antibodies. The combination of antibodies includes 3 patterns of antibody A and antibody B, antibody A and antibody C, and antibody B and antibody C, and ELISA was performed using the combinations. The vertical axis shows the quantitative values of the total amount of S38AA fragment, and the horizontal axis shows each sample. Numbers starting with TSUM indicate healthy individuals, and numbers starting with ASUM indicate AD patients.

Specifically, each plasma derived from 4 healthy subjects and 8 AD patients was quantified by "ELISA (pattern 1, 2, or 3) using an antibody consisting of a combination of two of antibody A, antibody B, and antibody C". Quantification was performed according to the method described in Example 4. The calibration curve of each ELISA was created by the measurement of S38AA long fragment standard protein, and the quantified value of each sample was obtained (FIG. 14).
  pattern 1: ELISA using antibody A and antibody B
  pattern 2: ELISA using antibody A and antibody C
  pattern 3: ELISA using antibody B and antibody C
  As a result of the measurement, the measurement value of "the total amount of "the amount of S38AA short fragment" and "the amount of S38AA long fragment"" was equivalent in each sample, and consistent quantification was obtained regardless of the combination of the antibodies used.

Example 9: Quantification of S38AA Fragment in Human Plasma by Combining Various Anti-S38AA Fragment Antibodies—2

To quantify "the amount of S38AA long fragment" contained in human plasma, ELISA quantification using various anti-S38AA fragment antibodies in combination was performed.

Figure 15:
FIG. 15 shows the quantitative values in each sample when S38AA fragment in human plasma is quantified by combining various anti-S38AA fragment antibodies. The combination of antibodies includes 3 patterns of antibody for long fragment and antibody A, antibody for long fragment and antibody B, and antibody for long fragment and antibody C, and ELISA was performed using the combinations. The vertical axis shows the quantitative value of the S38AA long fragment, and the horizontal axis shows each sample. Numbers starting with TSUM indicate healthy individuals, and numbers starting with ASUM indicate AD patients.

Specifically, each plasma derived from 4 healthy subjects and 8 AD patients was quantified by "ELISA (pattern 4, 5, or 6) using a combination in which one is antibody for Long fragment and the other is one of antibody A, antibody B, and antibody C. Quantification was performed according to the method described in Example 4. The calibration curve of each ELISA was created by the measurement of S38AA long fragment standard protein, and the quantified value of each sample was obtained (FIG. 15).
  pattern 4: ELISA using antibody for Long fragment and antibody A
  pattern 5: ELISA using antibody for Long fragment and antibody B
  pattern 6: ELISA using antibody for Long fragment and antibody C
  As a result of the measurement, the measurement value of "the amount of S38AA long fragment" was equivalent in each sample, and consistent quantitativeness was obtained regardless of the combination of the antibodies used.

Example 10: Quantification of S38AA Short Fragment in Human Plasma Using the Results of Examples 8 and 9

Figure 16:
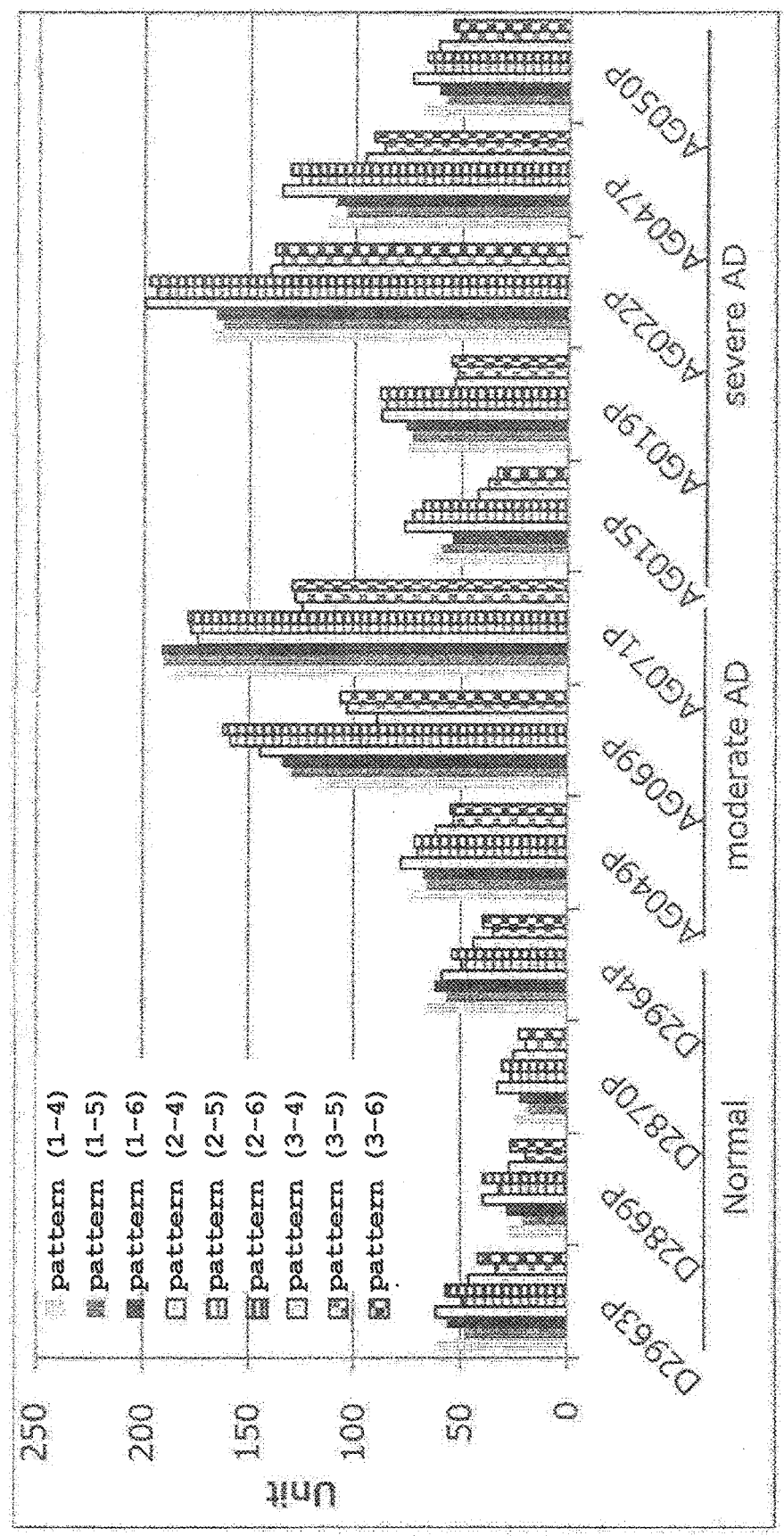
FIG. 16 shows the quantitative values in each sample when the S38AA short fragment in human plasma was quantified by the subtraction method, based on the results of FIGS. 14 and 15. The vertical axis shows the quantitative value of S38AA short fragment, and the horizontal axis shows each sample. Numbers starting with TSUM indicate healthy individuals, and numbers starting with ASUM indicate AD patient.

The "amount of S38AA short fragment" was determined by subtracting "the amount of S38AA long fragment" obtained in Example 9 from "the total amount of "the amount of S38AA short fragment" and "the amount of S38AA long fragment"" obtained in Example 8 (FIG. 16).

Specifically, the subtraction was performed in the following combinations.

pattern 1-4: results obtained by subtracting the "measurement results of pattern 4" from the "measurement results of pattern 1"

pattern 1-5: results obtained by subtracting the "measurement results of pattern 5" from the "measurement results of pattern 1"

pattern 1-6: results obtained by subtracting the "measurement results of pattern 6" from the "measurement results of pattern 1"

pattern 2-4: results obtained by subtracting the "measurement results of pattern 4" from the "measurement results of pattern 2"

pattern 2-5: results obtained by subtracting the "measurement results of pattern 5" from the "measurement results of pattern 2"

pattern 2-6: results obtained by subtracting the "measurement results of pattern 6" from the "measurement results of pattern 2"

pattern 3-4: results obtained by subtracting the "measurement results of pattern 4" from the "measurement results of pattern 3"

pattern 3-5: results obtained by subtracting the "measurement results of pattern 5" from the "measurement results of pattern 3"

pattern 3-6: results obtained by subtracting the "measurement results of pattern 6" from the "measurement results of pattern 3"

The "amount of S38AA short fragment" obtained by the subtraction showed consistent quantitativeness regardless of the combination of the antibodies used.

This application is based on a patent application No. 2018-148924 filed in Japan (filing date: Aug. 7, 2018), the contents of which are incorporated in full herein.

INDUSTRIAL APPLICABILITY

The present invention is useful for the diagnosis and treatment of Alzheimer's disease, and the like.

The invention claimed is:

1. An antibody recognizing a S38AA polypeptide, wherein the S38AA polypeptide consists of the amino acid sequence of SEQ ID NO: 1, or an amino acid sequence resulting from substitution, deletion, addition, or insertion of one to several amino acids in the amino acid sequence of SEQ ID NO: 1, and wherein the antibody is
   (a) an antibody comprising the heavy chain variable region of SEQ ID NO: 4, and the light chain variable region of SEQ ID NO: 5,
   (b) an antibody comprising the heavy chain variable region of SEQ ID NO: 6, and the light chain variable region of SEQ ID NO: 7,
   (c) an antibody comprising the heavy chain variable region of SEQ ID NO: 8, and the light chain variable region of SEQ ID NO: 9,
   (d) an antibody comprising the heavy chain variable region of SEQ ID NO: 10, and the light chain variable region of SEQ ID NO: 11,
   (e) an antibody comprising the heavy chain variable region of SEQ ID NO: 12, and the light chain variable region of SEQ ID NO: 13,
   (f) an antibody comprising the heavy chain variable region of SEQ ID NO: 14, and the light chain variable region of SEQ ID NO: 15,
   (g) an antibody comprising the heavy chain variable region of SEQ ID NO: 16, and the light chain variable region of SEQ ID NO: 17,
   (h) an antibody comprising the heavy chain variable region of SEQ ID NO: 18, and the light chain variable region of SEQ ID NO: 19,
   (i) an antibody comprising the heavy chain variable region of SEQ ID NO: 20, and the light chain variable region of SEQ ID NO: 21, or
   (j) an antibody comprising the heavy chain variable region of SEQ ID NO: 22, and the light chain variable region of SEQ ID NO: 23.

2. The antibody of claim 1, further recognizing the polypeptide of SEQ ID NO: 2.

3. The antibody of claim 1, wherein the S38AA polypeptide consists of the amino acid sequence of SEQ ID NO: 1.

4. The antibody of claim 1, wherein the antibody is an antibody comprising the heavy chain variable region of SEQ ID NO: 4, and the light chain variable region of SEQ ID NO: 5.

5. The antibody of claim 1, wherein the antibody is an antibody comprising the heavy chain variable region of SEQ ID NO: 6, and the light chain variable region of SEQ ID NO: 7.

6. The antibody of claim 1, wherein the antibody is an antibody comprising the heavy chain variable region of SEQ ID NO: 8, and the light chain variable region of SEQ ID NO: 9.

7. The antibody of claim 1, wherein the antibody is an antibody comprising the heavy chain variable region of SEQ ID NO: 10, and the light chain variable region of SEQ ID NO: 11.

8. The antibody of claim 1, wherein the antibody is an antibody comprising the heavy chain variable region of SEQ ID NO: 12, and the light chain variable region of SEQ ID NO: 13.

9. The antibody of claim 1, wherein the antibody is an antibody comprising the heavy chain variable region of SEQ ID NO: 14, and the light chain variable region of SEQ ID NO: 15.

10. The antibody of claim 1, wherein the antibody is an antibody comprising the heavy chain variable region of SEQ ID NO: 16, and the light chain variable region of SEQ ID NO: 17.

11. The antibody of claim 1, wherein the antibody is an antibody comprising the heavy chain variable region of SEQ ID NO: 18, and the light chain variable region of SEQ ID NO: 19.

12. The antibody of claim 1, wherein the antibody is an antibody comprising the heavy chain variable region of SEQ ID NO: 20, and the light chain variable region of SEQ ID NO: 21.

13. The antibody of claim 1, wherein the antibody is an antibody comprising the heavy chain variable region of SEQ ID NO: 22, and the light chain variable region of SEQ ID NO: 23.

14. An agent for determining Alzheimer's disease or the progression of Alzheimer's disease in a subject, comprising the antibody of claim 1.

15. A kit comprising the antibody of claim 1.

16. The kit of claim 15, further comprising a S38AA polypeptide, wherein the S38AA polypeptide consists of the amino acid sequence of SEQ ID NO: 1, or an amino acid sequence resulting from substitution, deletion, addition, or insertion of one to several amino acids in the amino acid sequence of SEQ ID NO: 1.

17. A method for detecting a S38AA polypeptide, wherein the S38AA polypeptide consists of the amino acid sequence of SEQ ID NO: 1, or an amino acid sequence resulting from substitution, deletion, addition, or insertion of one to several amino acids in the amino acid sequence of SEQ ID NO: 1, which method comprises a step of contacting a test sample with the antibody of claim 1.

* * * * *

SEQUENCE LISTING

```
<160> NUMBER OF SEQ ID NOS: 23

<210> SEQ ID NO 1
<211> LENGTH: 433
<212> TYPE: PRT
<213> ORGANISM: Homo sapiens

<400> SEQUENCE: 1

Gly Leu Ala Val Gly Gly Gly Glu Lys Ala Lys Gly Gly Pro Pro Pro
1               5                   10                  15

Gly Asn Ala Ala Gly Asp Thr Gly Gln Pro Ala Glu Asp Ser Asp His
                20                  25                  30

Gly Gly Lys Pro Pro Leu Pro Ala Glu Lys Pro Ala Pro Gly Pro Gly
            35                  40                  45

Leu Pro Pro Glu Pro Arg Glu Gln Arg Asp Val Glu Arg Ala Gly Gly
    50                  55                  60

Asn Gln Ala Ala Ser Gln Leu Glu Glu Ala Gly Arg Ala Glu Met Leu
65                  70                  75                  80

Asp His Ala Val Leu Leu Gln Val Ile Lys Glu Gln Gln Val Gln Gln
                85                  90                  95

Lys Arg Leu Leu Asp Gln Gln Glu Lys Leu Leu Ala Val Ile Glu Glu
                100                 105                 110

Gln His Lys Glu Ile His Gln Gln Arg Gln Glu Asp Glu Glu Asp Lys
            115                 120                 125

Pro Arg Gln Val Glu Val His Gln Glu Pro Gly Ala Ala Val Pro Arg
    130                 135                 140

Gly Gln Glu Ala Pro Glu Gly Lys Ala Arg Glu Thr Val Glu Asn Leu
145                 150                 155                 160

Pro Pro Leu Pro Leu Asp Pro Val Leu Arg Ala Pro Gly Gly Arg Pro
                165                 170                 175

Ala Pro Ser Gln Asp Leu Asn Gln Arg Ser Leu Glu His Ser Glu Gly
            180                 185                 190

Pro Val Gly Arg Asp Pro Ala Gly Pro Pro Asp Gly Gly Pro Asp Thr
    195                 200                 205

Glu Pro Arg Ala Ala Gln Ala Lys Leu Arg Asp Gly Gln Lys Asp Ala
    210                 215                 220

Ala Pro Arg Ala Ala Gly Thr Val Lys Glu Leu Pro Lys Gly Pro Glu
```

```
            225                 230                 235                 240
        Gln Val Pro Val Pro Asp Pro Ala Arg Glu Ala Gly Gly Pro Glu Glu
                        245                 250                 255

Arg Leu Ala Glu Glu Phe Pro Gly Gln Ser Gln Asp Val Thr Gly Gly
                    260                 265                 270

Ser Gln Asp Arg Lys Pro Lys Glu Val Ala Ala Thr Gly Thr
                275                 280                 285

Ser Ile Leu Lys Glu Ala Asn Trp Leu Val Ala Gly Pro Gly Ala Glu
                290                 295                 300

Thr Gly Asp Pro Arg Met Lys Pro Lys Gln Val Ser Arg Asp Leu Gly
        305                 310                 315                 320

Leu Ala Ala Asp Leu Pro Gly Gly Ala Glu Gly Ala Ala Gln Pro
                        325                 330                 335

Gln Ala Val Leu Arg Gln Pro Glu Leu Arg Val Ile Ser Asp Gly Glu
                    340                 345                 350

Gln Gly Gly Gln Gln Gly His Arg Leu Asp His Gly Gly His Leu Glu
                    355                 360                 365

Met Arg Lys Ala Arg Gly Gly Asp His Val Pro Val Ser His Glu Gln
            370                 375                 380

Pro Arg Gly Gly Glu Asp Ala Ala Val Gln Glu Pro Arg Gln Arg Pro
        385                 390                 395                 400

Glu Pro Glu Leu Gly Leu Lys Arg Ala Val Pro Gly Gly Gln Arg Pro
                        405                 410                 415

Asp Asn Ala Lys Pro Asn Arg Asp Leu Lys Leu Gln Ala Gly Ser Asp
                    420                 425                 430

Leu

<210> SEQ ID NO 2
<211> LENGTH: 651
<212> TYPE: PRT
<213> ORGANISM: Homo sapiens

<400> SEQUENCE: 2

Glu Glu Val Pro Glu Asp Leu Ala Glu Ala Pro Gly Gly Arg Leu
        1               5                   10                  15

Gly Glu Ala Glu Gly Leu Met Lys Val Glu Ala Arg Leu Ser Ala
                    20                  25                  30

Gln Asp Pro Val Val Ala Val Ala Glu Asp Gly Arg Glu Lys Pro Lys
                    35                  40                  45

Leu Pro Lys Glu Arg Glu Leu Glu Gln Ala Gln Ile Lys Gly Pro
            50                  55                  60

Val Asp Val Pro Gly Arg Glu Asp Gly Lys Glu Ala Pro Glu Glu Ala
        65                  70                  75                  80

Gln Leu Asp Arg Pro Gly Gln Gly Ile Ala Val Pro Val Gly Glu Ala
                        85                  90                  95

His Arg His Glu Pro Val Pro His Asp Lys Val Val Val Asp Glu
                    100                 105                 110

Gly Gln Asp Arg Glu Val Pro Glu Glu Asn Lys Pro Pro Ser Arg His
                    115                 120                 125

Ala Gly Gly Lys Ala Pro Gly Val Gln Gly Gln Met Ala Pro Pro Leu
                130                 135                 140

Pro Asp Ser Glu Arg Glu Lys Gln Glu Pro Glu Gln Gly Glu Val Gly
        145                 150                 155                 160

Lys Arg Pro Gly Gln Ala Gln Ala Leu Glu Glu Ala Gly Asp Leu Pro
```

-continued

```
                165                 170                 175
Glu Asp Pro Gln Lys Val Pro Glu Ala Asp Gly Gln Pro Ala Val Gln
            180                 185                 190

Pro Ala Lys Glu Asp Leu Gly Pro Gly Asp Arg Gly Leu His Pro Arg
            195                 200                 205

Pro Gln Ala Val Leu Ser Glu Gln Asn Gly Leu Ala Val Gly Gly
            210                 215                 220

Gly Glu Lys Ala Lys Gly Gly Pro Pro Gly Asn Ala Ala Gly Asp
225                 230                 235                 240

Thr Gly Gln Pro Ala Glu Asp Ser Asp His Gly Gly Lys Pro Pro Leu
                245                 250                 255

Pro Ala Glu Lys Pro Ala Pro Gly Pro Gly Leu Pro Pro Glu Pro Arg
            260                 265                 270

Glu Gln Arg Asp Val Glu Arg Ala Gly Gly Asn Gln Ala Ala Ser Gln
            275                 280                 285

Leu Glu Glu Ala Gly Arg Ala Glu Met Leu Asp His Ala Val Leu Leu
            290                 295                 300

Gln Val Ile Lys Glu Gln Gln Val Gln Gln Lys Arg Leu Leu Asp Gln
305                 310                 315                 320

Gln Glu Lys Leu Leu Ala Val Ile Glu Glu Gln His Lys Glu Ile His
                325                 330                 335

Gln Gln Arg Gln Glu Asp Glu Glu Asp Lys Pro Arg Gln Val Glu Val
            340                 345                 350

His Gln Glu Pro Gly Ala Ala Val Pro Arg Gly Gln Glu Ala Pro Glu
            355                 360                 365

Gly Lys Ala Arg Glu Thr Val Glu Asn Leu Pro Pro Leu Pro Leu Asp
            370                 375                 380

Pro Val Leu Arg Ala Pro Gly Gly Arg Pro Ala Pro Ser Gln Asp Leu
385                 390                 395                 400

Asn Gln Arg Ser Leu Glu His Ser Glu Gly Pro Val Gly Arg Asp Pro
                405                 410                 415

Ala Gly Pro Pro Asp Gly Gly Pro Asp Thr Glu Pro Arg Ala Ala Gln
            420                 425                 430

Ala Lys Leu Arg Asp Gly Gln Lys Asp Ala Ala Pro Arg Ala Ala Gly
            435                 440                 445

Thr Val Lys Glu Leu Pro Lys Gly Pro Glu Gln Val Pro Val Pro Asp
            450                 455                 460

Pro Ala Arg Glu Ala Gly Gly Pro Glu Glu Arg Leu Ala Glu Glu Phe
465                 470                 475                 480

Pro Gly Gln Ser Gln Asp Val Thr Gly Gly Ser Gln Asp Arg Lys Lys
                485                 490                 495

Pro Gly Lys Glu Val Ala Ala Thr Gly Thr Ser Ile Leu Lys Glu Ala
            500                 505                 510

Asn Trp Leu Val Ala Gly Pro Gly Ala Glu Thr Gly Asp Pro Arg Met
            515                 520                 525

Lys Pro Lys Gln Val Ser Arg Asp Leu Gly Leu Ala Ala Asp Leu Pro
            530                 535                 540

Gly Gly Ala Glu Gly Ala Ala Gln Pro Gln Ala Val Leu Arg Gln
545                 550                 555                 560

Pro Glu Leu Arg Val Ile Ser Asp Gly Glu Gln Gly Gln Gln Gly
                565                 570                 575

His Arg Leu Asp His Gly Gly His Leu Glu Met Arg Lys Ala Arg Gly
            580                 585                 590
```

```
Gly Asp His Val Pro Val Ser His Glu Gln Pro Arg Gly Gly Glu Asp
            595                 600                 605

Ala Ala Val Gln Glu Pro Arg Gln Arg Pro Glu Pro Glu Leu Gly Leu
            610                 615                 620

Lys Arg Ala Val Pro Gly Gly Gln Arg Pro Asp Asn Ala Lys Pro Asn
625                 630                 635                 640

Arg Asp Leu Lys Leu Gln Ala Gly Ser Asp Leu
            645                 650

<210> SEQ ID NO 3
<211> LENGTH: 1119
<212> TYPE: PRT
<213> ORGANISM: Homo sapiens

<400> SEQUENCE: 3

Met Thr Ala Ala Ala Ser Asn Trp Gly Leu Ile Thr Asn Ile Val
1               5                   10                  15

Asn Ser Ile Val Gly Val Ser Val Leu Thr Met Pro Phe Cys Phe Lys
                20                  25                  30

Gln Cys Gly Ile Val Leu Gly Ala Leu Leu Leu Val Phe Cys Ser Trp
            35                  40                  45

Met Thr His Gln Ser Cys Met Phe Leu Val Lys Ser Ala Ser Leu Ser
50                  55                  60

Lys Arg Arg Thr Tyr Ala Gly Leu Ala Phe His Ala Tyr Gly Lys Ala
65                  70                  75                  80

Gly Lys Met Leu Val Glu Thr Ser Met Ile Gly Leu Met Leu Gly Thr
                85                  90                  95

Cys Ile Ala Phe Tyr Val Val Ile Gly Asp Leu Gly Ser Asn Phe Phe
            100                 105                 110

Ala Arg Leu Phe Gly Phe Gln Val Gly Gly Thr Phe Arg Met Phe Leu
            115                 120                 125

Leu Phe Ala Val Ser Leu Cys Ile Val Leu Pro Leu Ser Leu Gln Arg
            130                 135                 140

Asn Met Met Ala Ser Ile Gln Ser Phe Ser Ala Met Ala Leu Leu Phe
145                 150                 155                 160

Tyr Thr Val Phe Met Phe Val Ile Val Leu Ser Ser Leu Lys His Gly
                165                 170                 175

Leu Phe Ser Gly Gln Trp Leu Arg Arg Val Ser Tyr Val Arg Trp Glu
            180                 185                 190

Gly Val Phe Arg Cys Ile Pro Ile Phe Gly Met Ser Phe Ala Cys Gln
            195                 200                 205

Ser Gln Val Leu Pro Thr Tyr Asp Ser Leu Asp Glu Pro Ser Val Lys
            210                 215                 220

Thr Met Ser Ser Ile Phe Ala Ser Ser Leu Asn Val Val Thr Thr Phe
225                 230                 235                 240

Tyr Val Met Val Gly Phe Phe Gly Tyr Val Ser Phe Thr Glu Ala Thr
                245                 250                 255

Ala Gly Asn Val Leu Met His Phe Pro Ser Asn Leu Val Thr Glu Met
            260                 265                 270

Leu Arg Val Gly Phe Met Met Ser Val Ala Val Gly Phe Pro Met Met
            275                 280                 285

Ile Leu Pro Cys Arg Gln Ala Leu Ser Thr Leu Leu Cys Glu Gln Gln
            290                 295                 300

Gln Lys Asp Gly Thr Phe Ala Ala Gly Gly Tyr Met Pro Pro Leu Arg
```

```
                305                 310                 315                 320
        Phe Lys Ala Leu Thr Leu Ser Val Val Phe Gly Thr Met Val Gly Gly
                        325                 330                 335
        Ile Leu Ile Pro Asn Val Glu Thr Ile Leu Gly Leu Thr Gly Ala Thr
                        340                 345                 350
        Met Gly Ser Leu Ile Cys Phe Ile Cys Pro Ala Leu Ile Tyr Lys Lys
                        355                 360                 365
        Ile His Lys Asn Ala Leu Ser Ser Gln Val Val Leu Trp Val Gly Leu
                        370                 375                 380
        Gly Val Leu Val Val Ser Thr Val Thr Thr Leu Ser Val Ser Glu Glu
        385                 390                 395                 400
        Val Pro Glu Asp Leu Ala Glu Ala Pro Gly Gly Arg Leu Gly Glu
                        405                 410                 415
        Ala Glu Gly Leu Met Lys Val Glu Ala Ala Arg Leu Ser Ala Gln Asp
                        420                 425                 430
        Pro Val Val Ala Val Ala Glu Asp Gly Arg Glu Lys Pro Lys Leu Pro
                        435                 440                 445
        Lys Glu Arg Glu Glu Leu Glu Gln Ala Gln Ile Lys Gly Pro Val Asp
                        450                 455                 460
        Val Pro Gly Arg Glu Asp Gly Lys Glu Ala Pro Glu Glu Ala Gln Leu
        465                 470                 475                 480
        Asp Arg Pro Gly Gln Gly Ile Ala Val Pro Val Gly Glu Ala His Arg
                        485                 490                 495
        His Glu Pro Pro Val Pro His Asp Lys Val Val Asp Glu Gly Gln
                        500                 505                 510
        Asp Arg Glu Val Pro Glu Asn Lys Pro Pro Ser Arg His Ala Gly
                        515                 520                 525
        Gly Lys Ala Pro Gly Val Gln Gly Gln Met Ala Pro Pro Leu Pro Asp
                        530                 535                 540
        Ser Glu Arg Glu Lys Gln Glu Pro Glu Gln Gly Glu Val Gly Lys Arg
        545                 550                 555                 560
        Pro Gly Gln Ala Gln Ala Leu Glu Glu Ala Gly Asp Leu Pro Glu Asp
                        565                 570                 575
        Pro Gln Lys Val Pro Glu Ala Asp Gly Gln Pro Ala Val Gln Pro Ala
                        580                 585                 590
        Lys Glu Asp Leu Gly Pro Gly Asp Arg Gly Leu His Pro Arg Pro Gln
                        595                 600                 605
        Ala Val Leu Ser Glu Gln Gln Asn Gly Leu Ala Val Gly Gly Gly Glu
                        610                 615                 620
        Lys Ala Lys Gly Gly Pro Pro Gly Asn Ala Ala Gly Asp Thr Gly
        625                 630                 635                 640
        Gln Pro Ala Glu Asp Ser Asp His Gly Lys Pro Pro Leu Pro Ala
                        645                 650                 655
        Glu Lys Pro Ala Pro Gly Pro Gly Leu Pro Pro Glu Pro Arg Glu Gln
                        660                 665                 670
        Arg Asp Val Glu Arg Ala Gly Gly Asn Gln Ala Ala Ser Gln Leu Glu
                        675                 680                 685
        Glu Ala Gly Arg Ala Glu Met Leu Asp His Ala Val Leu Leu Gln Val
                        690                 695                 700
        Ile Lys Glu Gln Gln Val Gln Gln Lys Arg Leu Leu Asp Gln Gln Glu
        705                 710                 715                 720
        Lys Leu Leu Ala Val Ile Glu Glu Gln His Lys Glu Ile His Gln Gln
                        725                 730                 735
```

Arg Gln Glu Asp Glu Glu Asp Lys Pro Arg Gln Val Glu Val His Gln
                740                 745                 750

Glu Pro Gly Ala Ala Val Pro Arg Gly Gln Glu Ala Pro Glu Gly Lys
        755                 760                 765

Ala Arg Glu Thr Val Glu Asn Leu Pro Pro Leu Pro Leu Asp Pro Val
770                 775                 780

Leu Arg Ala Pro Gly Gly Arg Pro Ala Pro Ser Gln Asp Leu Asn Gln
785                 790                 795                 800

Arg Ser Leu Glu His Ser Glu Pro Val Gly Arg Asp Pro Ala Gly
        805                 810                 815

Pro Pro Asp Gly Gly Pro Asp Thr Glu Pro Arg Ala Ala Gln Ala Lys
        820                 825                 830

Leu Arg Asp Gly Gln Lys Asp Ala Ala Pro Arg Ala Ala Gly Thr Val
        835                 840                 845

Lys Glu Leu Pro Lys Gly Pro Glu Gln Val Pro Val Pro Asp Pro Ala
        850                 855                 860

Arg Glu Ala Gly Gly Pro Glu Glu Arg Leu Ala Glu Glu Phe Pro Gly
865                 870                 875                 880

Gln Ser Gln Asp Val Thr Gly Gly Ser Gln Asp Arg Lys Lys Pro Gly
                885                 890                 895

Lys Glu Val Ala Ala Thr Gly Thr Ser Ile Leu Lys Glu Ala Asn Trp
        900                 905                 910

Leu Val Ala Gly Pro Gly Ala Glu Thr Gly Asp Pro Arg Met Lys Pro
        915                 920                 925

Lys Gln Val Ser Arg Asp Leu Gly Leu Ala Ala Asp Leu Pro Gly Gly
        930                 935                 940

Ala Glu Gly Ala Ala Ala Gln Pro Gln Ala Val Leu Arg Gln Pro Glu
945                 950                 955                 960

Leu Arg Val Ile Ser Asp Gly Glu Gln Gly Gly Gln Gln Gly His Arg
                965                 970                 975

Leu Asp His Gly Gly His Leu Glu Met Arg Lys Ala Arg Gly Gly Asp
        980                 985                 990

His Val Pro Val Ser His Glu Gln Pro Arg Gly Gly Glu Asp Ala Ala
        995                 1000                1005

Val Gln Glu Pro Arg Gln Arg Pro Glu Pro Glu Leu Gly Leu Lys
        1010                1015                1020

Arg Ala Val Pro Gly Gly Gln Arg Pro Asp Asn Ala Lys Pro Asn
        1025                1030                1035

Arg Asp Leu Lys Leu Gln Ala Gly Ser Asp Leu Arg Arg Arg Arg
        1040                1045                1050

Arg Asp Leu Gly Pro His Ala Glu Gly Gln Leu Ala Pro Arg Asp
        1055                1060                1065

Gly Val Ile Ile Gly Leu Asn Pro Leu Pro Asp Val Gln Val Asn
        1070                1075                1080

Asp Leu Arg Gly Ala Leu Asp Ala Gln Leu Arg Gln Ala Ala Gly
        1085                1090                1095

Gly Ala Leu Gln Val Val His Ser Arg Gln Leu Arg Gln Ala Pro
        1100                1105                1110

Gly Pro Pro Glu Glu Ser
        1115

<210> SEQ ID NO 4
<211> LENGTH: 114

```
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 4

Gly Ser Leu Asp Gln Ser Asn Cys Leu Gly Tyr Ile Phe Ser Ser Ala
1               5                   10                  15

Pro Ser Arg Phe Leu Ser Tyr Ser Ser Gly Leu Leu Ser Arg Thr
            20                  25                  30

Val His Val Ala Ser Cys Trp Arg Pro Gln Gln Gly Met Thr Glu Gly
        35                  40                  45

Leu His Arg Val Trp Gly Arg Ser Lys Lys Thr Glu Leu Lys Asn Gln
    50                  55                  60

Asp Asn Pro Glu Gln Thr Val Arg Asp Met Leu Ser Ile Tyr Arg Gly
65                  70                  75                  80

Cys Thr Lys Thr Thr Ala Pro Ser Val Tyr Pro Leu Ala Pro Val Cys
                85                  90                  95

Gly Asp Thr Thr Gly Ser Ser Val Thr Leu Gly Cys Leu Val Lys Gly
            100                 105                 110

Tyr Phe

<210> SEQ ID NO 5
<211> LENGTH: 194
<212> TYPE: PRT
<213> ORGANISM: Artificial Sequence
<220> FEATURE:
<223> OTHER INFORMATION: Synthetic Sequence -variable region
      (light chain) of anti-S38AA antibody

<400> SEQUENCE: 5

Asp Ser Lys Val Leu Met Arg Ile Val Val Ile Ser Gly Pro Lys Phe
1               5                   10                  15

Lys Asp Lys Met Asp Phe Gln Val Gln Ile Phe Ser Phe Leu Leu Ile
            20                  25                  30

Ser Ala Ser Val Ile Leu Ser Arg Gly Gln Ile Val Leu Thr Gln Ser
        35                  40                  45

Pro Pro Ile Met Ser Ala Ser Pro Gly Glu Lys Val Ile Met Thr Cys
    50                  55                  60

Ser Ala Ser Ser Ser Ile Ser Tyr Met Phe Trp Tyr Gln Gln Lys Pro
65                  70                  75                  80

Gly Ser Ser Pro Arg Leu Leu Ile Tyr Asp Thr Ser Asn Leu Ala Ser
                85                  90                  95

Gly Val Pro Val Arg Phe Ser Gly Ser Gly Ser Gly Thr Ser Tyr Ser
            100                 105                 110

Leu Thr Ile Ser Arg Met Glu Ala Glu Asp Ala Ala Thr Tyr Tyr Cys
        115                 120                 125

Gln Gln Trp Ser Tyr Tyr Pro Pro Ile Thr Phe Gly Thr Gly Thr Lys
    130                 135                 140

Leu Glu Leu Lys Arg Ala Asp Ala Ala Pro Thr Val Ser Ile Phe Pro
145                 150                 155                 160

Pro Ser Ser Glu Gln Leu Thr Ser Gly Gly Ala Ser Val Val Cys Phe
                165                 170                 175

Leu Asn Asn Phe Tyr Pro Lys Asp Ile Asn Val Lys Trp Lys Ile Asp
            180                 185                 190

Gly Ser
```

<210> SEQ ID NO 6
<211> LENGTH: 184
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 6

Lys Asn Asn Thr Cys Pro Met Ser Ser Pro Gln Thr Leu Asn Thr Leu
1               5                   10                  15

Thr Pro Thr Met Gly Trp Ser Trp Ile Phe Leu Phe Leu Leu Ser Gly
            20                  25                  30

Thr Gly Gly Val Leu Ser Glu Val Leu Leu Gln Gln Ser Gly Pro Glu
        35                  40                  45

Leu Val Lys Pro Gly Ala Ser Val Lys Met Ser Cys Lys Ala Ser Gly
    50                  55                  60

Tyr Thr Phe Thr Asp Tyr Ser Met Lys Trp Val Arg Gln Ser His Gly
65                  70                  75                  80

Lys Ser Leu Glu Trp Ile Gly Asp Ile Asp Pro Asn Asn Gly Asp Thr
                85                  90                  95

Leu Tyr Asn Gln Met Phe Lys Gly Lys Ala Thr Leu Thr Val Asp Lys
            100                 105                 110

Ser Ser Thr Thr Ala Tyr Ile Gln Leu Asn Ser Leu Thr Ser Glu Asp
        115                 120                 125

Ser Ala Val Tyr Tyr Cys Val Arg Ser Asn Gly Tyr Trp Gly Gln Gly
    130                 135                 140

Thr Thr Leu Thr Val Ser Ser Ala Lys Thr Thr Ala Pro Ser Val Tyr
145                 150                 155                 160

Pro Leu Ala Pro Val Cys Gly Asp Thr Thr Gly Ser Ser Val Thr Leu
                165                 170                 175

Gly Cys Leu Val Lys Gly Tyr Phe
            180

<210> SEQ ID NO 7
<211> LENGTH: 194
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 7

Gly Val Thr Asp Gln Ser Pro Gln Ala Val Ser Ser Gly Cys Leu Leu
1               5                   10                  15

Lys Met Lys Leu Pro Val Arg Leu Leu Val Leu Met Phe Trp Ile Pro
            20                  25                  30

Ala Ser Ser Ser Asp Val Leu Met Thr Gln Thr Pro Leu Ser Leu Pro
        35                  40                  45

Val Ser Leu Gly Asp Gln Ala Ser Ile Ser Cys Arg Ser Ser Gln Ser
    50                  55                  60

Ile Val His Ser Asn Gly Asn Thr Tyr Leu Glu Trp Tyr Leu Gln Lys
65                  70                  75                  80

Pro Gly Gln Ser Pro Lys Leu Leu Ile Tyr Lys Val Ser Lys Arg Phe
                85                  90                  95

Ser Gly Val Pro Asp Arg Phe Ser Gly Ser Gly Ser Gly Thr Asp Phe
            100                 105                 110

Thr Leu Lys Ile Ser Arg Val Glu Ala Glu Asp Leu Gly Val Tyr Tyr
            115                 120                 125

Cys Phe Gln Gly Ser His Val Pro Trp Thr Phe Gly Gly Gly Thr Lys
            130                 135                 140

Leu Glu Ile Lys Arg Ala Asp Ala Ala Pro Thr Val Ser Ile Phe Pro
145                 150                 155                 160

Pro Ser Ser Glu Gln Leu Thr Ser Gly Gly Ala Ser Val Val Cys Phe
            165                 170                 175

Leu Asn Asn Phe Tyr Pro Lys Asp Ile Asn Val Lys Trp Lys Ile Asp
            180                 185                 190

Gly Ser

<210> SEQ ID NO 8
<211> LENGTH: 193
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 8

Asn Asn Thr Cys Pro Met Ser Ser Pro Gln Thr Leu Asn Thr Leu Thr
1               5                   10                  15

Pro Thr Met Gly Trp Ser Trp Ile Phe Leu Phe Leu Leu Ser Gly Thr
            20                  25                  30

Gly Gly Val His Ser Glu Val Gln Leu Gln Gln Ser Gly Pro Glu Leu
            35                  40                  45

Val Lys Pro Gly Ala Ser Val Lys Met Ser Cys Lys Ala Ser Gly Tyr
50                  55                  60

Thr Phe Thr Asp Tyr Thr Met Lys Trp Val Lys Gln Ser His Gly Lys
65                  70                  75                  80

Ser Leu Glu Trp Ile Gly Asp Ile Lys Ser Leu Glu Trp Ile Gly Asp
            85                  90                  95

Ile Asp Pro Asn Asn Gly Asp Asn Leu Tyr Asn Gln Lys Phe Lys Gly
            100                 105                 110

Lys Ala Thr Leu Thr Val Asp Lys Ser Ser Thr Ala Tyr Met Gln
            115                 120                 125

Phe Asn Ser Leu Thr Ser Glu Asp Ser Ala Val Tyr Tyr Cys Val Arg
            130                 135                 140

Ser Asn Gly Tyr Trp Gly Gln Gly Thr Thr Leu Thr Val Ser Ser Ala
145                 150                 155                 160

Lys Thr Thr Ala Pro Ser Val Tyr Pro Leu Ala Pro Val Cys Gly Asp
            165                 170                 175

Thr Thr Gly Ser Ser Val Thr Leu Gly Cys Leu Val Lys Gly Tyr Phe
            180                 185                 190

Pro

<210> SEQ ID NO 9
<211> LENGTH: 202
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 9

Ser Ser Gly Ile Asn Ala Glu Tyr Met Gly Thr Asp Gln Ser Pro Gln

```
                1               5                  10                 15
            Ala Val Ser Ser Gly Cys Leu Leu Lys Met Lys Leu Pro Val Arg Leu
                            20                  25                  30

Leu Val Leu Met Phe Trp Ile Pro Ala Ser Thr Ser Asp Val Leu Met
                            35                  40                  45

Thr Gln Thr Pro Leu Ser Leu Pro Val Ser Leu Gly Asp Gln Ala Ser
                        50                  55                  60

Ile Ser Cys Arg Ser Ser Gln Asn Ile Val His Ser Asn Gly Asn Thr
             65                 70                  75                  80

Tyr Leu Glu Trp Tyr Leu Gln Lys Pro Gly Gln Ser Pro Lys Leu Leu
                            85                  90                  95

Ile Tyr Lys Val Ser Asn Arg Phe Ser Gly Val Pro Asp Arg Phe Ser
                            100                 105                 110

Gly Ser Gly Ser Gly Thr Asp Phe Thr Leu Lys Ile Ser Arg Val Glu
                            115                 120                 125

Ala Glu Asp Leu Gly Val Tyr Tyr Cys Phe Gln Gly Ser His Val Pro
                        130                 135                 140

Trp Thr Phe Gly Gly Gly Thr Lys Leu Glu Ile Lys Arg Ala Asp Ala
            145                 150                 155                 160

Ala Pro Thr Val Ser Ile Phe Pro Pro Ser Ser Glu Gln Leu Thr Ser
                            165                 170                 175

Gly Gly Ala Ser Val Val Cys Phe Leu Asn Asn Phe Tyr Pro Lys Asp
                        180                 185                 190

Ile Asn Val Lys Trp Lys Ile Asp Gly Ser
                        195                 200
```

<210> SEQ ID NO 10
<211> LENGTH: 190
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 10

```
            Glu Gly Tyr Gln His Pro Glu His Asn Thr Cys Pro Met Ser Ser Pro
             1               5                  10                  15

Gln Thr Leu Asn Thr Leu Thr Pro Thr Met Gly Trp Ser Trp Ile Phe
                            20                  25                  30

Leu Phe Leu Leu Ser Gly Thr Gly Gly Val Leu Ser Glu Val Gln Leu
                            35                  40                  45

Gln Gln Ser Gly Pro Glu Leu Val Lys Pro Gly Ala Ser Val Lys Met
                        50                  55                  60

Ser Cys Lys Ala Ser Gly Tyr Ile Leu Thr Asp Tyr Thr Met Lys Trp
             65                 70                  75                  80

Val Lys Gln Ser His Gly Lys Ser Leu Glu Trp Ile Gly Asp Ile Asp
                            85                  90                  95

Pro Asn Asn Gly Asp Thr Leu Tyr Asn Gln Lys Phe Lys Gly Lys Ala
                            100                 105                 110

Thr Leu Thr Val Asp Lys Ser Ser Thr Ala Tyr Met Gln Leu Asn
                            115                 120                 125

Ser Leu Thr Ser Glu Asp Ser Ala Thr Tyr Tyr Cys Val Arg Ser Asn
                        130                 135                 140

Gly Tyr Trp Gly Gln Gly Thr Leu Thr Val Ser Ser Ala Lys Thr
            145                 150                 155                 160
```

```
Thr Pro Pro Ser Val Tyr Pro Leu Ala Pro Gly Ser Ala Ala Gln Thr
                165                 170                 175

Asn Ser Met Val Thr Leu Gly Cys Leu Val Lys Gly Tyr Phe
            180                 185                 190

<210> SEQ ID NO 11
<211> LENGTH: 192
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 11

Thr Asp Gln Ser Pro Gln Ala Val Ser Ser Gly Cys Leu Leu Lys Met
1               5                   10                  15

Lys Leu Pro Val Arg Leu Leu Val Leu Met Phe Trp Ile Pro Ala Ser
                20                  25                  30

Ser Ser Asp Val Leu Met Thr Gln Thr Pro Val Ser Leu Pro Val Ser
            35                  40                  45

Leu Gly Asp Gln Ala Ser Ile Ser Cys Arg Ser Ser Gln Ser Ile Val
        50                  55                  60

His Ser Asn Gly Asn Thr Tyr Leu Glu Trp Tyr Leu Gln Lys Pro Gly
65                  70                  75                  80

Gln Ser Pro Lys Leu Leu Ile Tyr Lys Val Ser Asn Arg Phe Ser Gly
                85                  90                  95

Val Pro Asp Arg Phe Ile Ala Thr Gly Ser Gly Thr Asp Phe Thr Leu
                100                 105                 110

Lys Ile Ser Arg Val Glu Ala Glu Asp Leu Gly Leu Tyr Tyr Cys Phe
            115                 120                 125

Gln Gly Ser His Val Pro Trp Thr Phe Gly Gly Gly Thr Lys Leu Glu
        130                 135                 140

Ile Thr Arg Ala Asp Ala Ala Pro Thr Val Ser Ile Phe Pro Pro Ser
145                 150                 155                 160

Ser Glu Gln Leu Thr Ser Gly Gly Ala Ser Val Val Cys Phe Leu Asn
                165                 170                 175

Asn Phe Tyr Pro Lys Asp Ile Asn Val Lys Trp Lys Ile Asp Gly Ser
                180                 185                 190

<210> SEQ ID NO 12
<211> LENGTH: 193
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 12

Val Gly Ser Cys Pro Glu Phe Pro Asn Leu His Ile Gln Lys Ser Ala
1               5                   10                  15

Leu Ser Pro Val Thr Met Lys Leu Trp Leu Asn Trp Val Phe Leu Leu
                20                  25                  30

Thr Leu Leu His Gly Ile Gln Cys Glu Val Arg Leu Val Glu Ser Gly
            35                  40                  45

Gly Gly Leu Val Gln Pro Gly Gly Ser Leu Arg Leu Ser Cys Ala Thr
        50                  55                  60

Ser Gly Phe Thr Phe Ser Asp Phe Tyr Met Glu Trp Val Arg Gln Pro
65                  70                  75                  80
```

```
Pro Gly Lys Arg Leu Glu Trp Ile Ala Ala Ser Arg Asn Lys Ala Asn
                85                  90                  95

Asp Tyr Thr Thr Glu Tyr Ser Ala Ser Val Lys Gly Arg Phe Ile Val
            100                 105                 110

Ser Arg Asp Thr Ser Gln Ser Ile Leu Tyr Leu Gln Met Asn Ala Leu
            115                 120                 125

Arg Ala Glu Asp Thr Ala Ile Tyr Tyr Cys Thr Arg Asp Ala Leu Thr
            130                 135                 140

Ser Ala Phe Ala Tyr Trp Gly Gln Gly Thr Leu Val Thr Val Ser Ala
145                 150                 155                 160

Ala Thr Thr Thr Ala Pro Ser Val Tyr Pro Leu Val Pro Gly Cys Ser
                165                 170                 175

Asp Thr Ser Gly Ser Ser Val Thr Leu Gly Cys Leu Val Lys Gly Tyr
            180                 185                 190

Phe

<210> SEQ ID NO 13
<211> LENGTH: 192
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 13

Ser Cys Gln Glu Pro Lys Lys His Pro Leu Phe Gln Leu Ser Glu Met
1               5                   10                  15

Glu Thr Asp Thr Leu Leu Leu Trp Val Leu Leu Leu Trp Val Pro Gly
            20                  25                  30

Ser Thr Gly Asp Ile Val Leu Thr Gln Ser Pro Ala Ser Leu Ala Val
            35                  40                  45

Ser Leu Gly Gln Arg Ala Thr Ile Ser Cys Arg Ala Ser Lys Ser Val
50                  55                  60

Thr Thr Ser Gly Tyr Ser Tyr Met His Trp Tyr Gln Gln Lys Pro Gly
65                  70                  75                  80

Gln Pro Pro Lys Leu Leu Ile Tyr Leu Ala Ser Asn Leu Glu Ser Gly
                85                  90                  95

Val Pro Ala Arg Phe Ser Gly Ser Gly Ser Gly Thr Asp Phe Thr Leu
            100                 105                 110

Asn Ile His Pro Val Glu Glu Glu Asp Ala Ala Thr Tyr Tyr Cys Gln
            115                 120                 125

His Ser Arg Glu Leu Pro Pro Thr Phe Gly Ala Gly Thr Lys Leu Glu
            130                 135                 140

Leu Lys Arg Ala Asp Ala Ala Pro Thr Val Ser Ile Phe Pro Pro Ser
145                 150                 155                 160

Ser Glu Gln Leu Thr Ser Gly Gly Ala Ser Val Val Cys Phe Leu Asn
                165                 170                 175

Asn Phe Tyr Pro Lys Asp Ile Asn Val Lys Trp Lys Ile Asp Gly Ser
            180                 185                 190

<210> SEQ ID NO 14
<211> LENGTH: 195
<212> TYPE: PRT
<213> ORGANISM: Artificial Sequence
<220> FEATURE:
<223> OTHER INFORMATION: Synthetic Sequence - variable region
      (heavy chain) of anti-S38AA antibody
```

```
<400> SEQUENCE: 14

Leu Ala Val Gly Ser Cys Pro Glu Phe Pro Asn Leu His Ile Gln Lys
1               5                   10                  15

Ser Ala Leu Ser Pro Val Thr Met Lys Leu Trp Leu Asn Trp Val Phe
            20                  25                  30

Leu Leu Thr Leu Leu His Gly Ile Gln Cys Glu Val Lys Leu Val Glu
        35                  40                  45

Ser Gly Gly Gly Leu Val Gln Pro Gly Gly Ser Leu Arg Leu Ser Cys
    50                  55                  60

Ala Thr Ser Gly Phe Thr Phe Ser Asp Phe Tyr Met Glu Trp Val Arg
65                  70                  75                  80

Gln Pro Pro Gly Lys Arg Leu Glu Trp Ile Ala Ala Ser Arg Asn Lys
                85                  90                  95

Ala Asn Asp Tyr Thr Thr Glu Tyr Ser Ala Ser Val Lys Gly Arg Phe
            100                 105                 110

Ile Val Ser Arg Asp Thr Ser Gln Ser Ile Leu Tyr Leu Gln Met Asn
        115                 120                 125

Ala Leu Arg Thr Glu Asp Thr Ala Ile Tyr Tyr Cys Thr Arg Asp Ala
    130                 135                 140

Leu Asn Ser Ala Phe Ala Tyr Trp Gly Gln Gly Thr Leu Val Thr Val
145                 150                 155                 160

Ser Ala Ala Lys Thr Thr Pro Pro Ser Val Tyr Pro Leu Ala Pro Gly
                165                 170                 175

Ser Ala Ala Gln Thr Asn Ser Met Val Thr Leu Gly Cys Leu Val Lys
            180                 185                 190

Gly Tyr Phe
        195

<210> SEQ ID NO 15
<211> LENGTH: 201
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 15

Ser Ser Gly Gln Arg Arg Val His Gly Ser Cys Gln Glu Pro Lys Lys
1               5                   10                  15

His Pro Leu Phe Gln Leu Ser Glu Met Glu Thr Asp Thr Leu Leu Leu
            20                  25                  30

Trp Val Leu Leu Leu Trp Val Pro Gly Ser Thr Gly Asp Ile Val Leu
        35                  40                  45

Ala Gln Ser Pro Ala Ser Leu Ala Val Ser Leu Gly Gln Arg Ala Thr
    50                  55                  60

Ile Ser Cys Arg Ala Ser Lys Ser Val Thr Thr Ser Gly Tyr Ser Tyr
65                  70                  75                  80

Met His Trp Tyr Gln Gln Lys Pro Gly Gln Pro Pro Lys Leu Leu Ile
                85                  90                  95

Tyr Leu Ala Ser Asn Leu Glu Ser Gly Val Pro Ala Arg Phe Ser Gly
            100                 105                 110

Ser Gly Ser Gly Thr Asp Phe Thr Leu Asn Ile His Pro Val Glu Glu
        115                 120                 125

Glu Asp Ala Ala Thr Tyr Tyr Cys Gln His Ser Arg Glu Leu Pro Pro
    130                 135                 140
```

-continued

```
Thr Phe Gly Ala Gly Thr Lys Leu Glu Leu Lys Arg Ala Asp Ala Ala
145                 150                 155                 160

Pro Thr Val Ser Ile Phe Pro Pro Ser Ser Glu Gln Leu Thr Ser Gly
                165                 170                 175

Gly Ala Ser Val Val Cys Phe Leu Asn Asn Phe Tyr Pro Lys Asp Ile
                180                 185                 190

Asn Val Lys Trp Lys Ile Asp Gly Ser
                195                 200
```

<210> SEQ ID NO 16
<211> LENGTH: 186
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 16

```
Ile Ala Leu Ser Ser Leu Gln Thr Leu Asn Leu Lys Val Leu Thr Met
1               5                   10                  15

Lys Cys Ser Trp Val Ile Phe Phe Leu Met Ala Val Val Thr Gly Val
                20                  25                  30

Asn Ser Glu Val Gln Leu Gln Gln Ser Gly Ala Glu Leu Val Lys Pro
            35                  40                  45

Gly Ala Ser Leu Lys Leu Ser Cys Thr Ala Ser Gly Phe Asn Ile Lys
        50                  55                  60

Asp Thr Tyr Ile His Trp Val Lys Gln Arg Pro Glu Gln Gly Leu Glu
65                  70                  75                  80

Trp Ile Gly Arg Ile Asp Pro Ala Asn Gly Ile Thr Lys Tyr Asp Pro
                85                  90                  95

Lys Phe Gln Gly Lys Ala Thr Ile Thr Ala Asp Thr Ser Ser Asn Thr
                100                 105                 110

Ala Tyr Leu Gln Leu Ser Ser Leu Thr Ser Glu Asp Thr Ala Val Tyr
            115                 120                 125

Tyr Cys Ser Asp Tyr Tyr Arg Tyr Asp Asp Ser Met Asp Phe Trp Gly
        130                 135                 140

Gln Gly Thr Ser Val Thr Val Ser Ser Ala Lys Thr Thr Pro Pro Ser
145                 150                 155                 160

Val Tyr Pro Leu Ala Pro Gly Ser Ala Ala Gln Thr Asn Ser Met Val
                165                 170                 175

Thr Leu Gly Cys Leu Val Lys Gly Tyr Phe
                180                 185
```

<210> SEQ ID NO 17
<211> LENGTH: 185
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 17

```
Leu Ser Leu Ser Leu Gln Ser Gly Leu Ser Met Asp Met Arg Ala Pro
1               5                   10                  15

Ala Gln Ile Phe Gly Phe Leu Leu Leu Phe Pro Gly Thr Arg Cys
            20                  25                  30

Asp Ile Gln Met Thr Gln Ser Pro Ser Ser Leu Ser Ala Ser Leu Gly
            35                  40                  45
```

Glu Arg Val Ser Leu Thr Cys Arg Ala Ser Gln Asp Ile Gly Ser Asn
 50                  55                  60

Leu Asn Trp Leu Gln Gln Glu Pro Asp Gly Thr Ile Arg Arg Leu Ile
 65                  70                  75                  80

Tyr Asp Thr Ser Thr Leu Asp Ser Gly Val Pro Lys Arg Phe Ser Gly
                 85                  90                  95

Ser Arg Ser Gly Ser Asp Tyr Ser Leu Thr Ile Ser Ser Leu Glu Ser
                100                 105                 110

Glu Asp Phe Val Asp Tyr Tyr Cys Leu Gln Tyr Ala Thr Ser Pro Tyr
            115                 120                 125

Thr Phe Gly Gly Gly Thr Lys Leu Glu Ile Lys Arg Ala Asp Ala Ala
130                 135                 140

Pro Thr Val Ser Ile Phe Pro Pro Ser Ser Glu Gln Leu Thr Ser Gly
145                 150                 155                 160

Gly Ala Ser Val Val Cys Phe Leu Asn Asn Phe Tyr Pro Lys Asp Ile
                165                 170                 175

Asn Val Lys Trp Lys Ile Asp Gly Ser
            180                 185

<210> SEQ ID NO 18
<211> LENGTH: 186
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 18

Ile Ala Leu Ser Ser Leu Gln Thr Leu Asn Leu Lys Val Leu Thr Met
 1               5                  10                  15

Lys Cys Ser Trp Val Ile Phe Phe Leu Met Ala Val Val Thr Gly Val
                 20                  25                  30

Asn Ser Glu Val His Leu Gln Gln Ser Gly Thr Glu Leu Val Lys Pro
             35                  40                  45

Gly Ala Ser Val Lys Leu Ser Cys Thr Ala Ser Gly Phe Asn Ile Lys
 50                  55                  60

Asp Thr Tyr Ile His Trp Val Lys Gln Ser Pro Glu Gln Gly Leu Glu
 65                  70                  75                  80

Trp Ile Gly Arg Ile Asp Pro Ala Asn Gly Asn Thr Lys Tyr Asp Pro
                 85                  90                  95

Lys Phe Gln Gly Lys Ala Thr Ile Thr Ala Asp Thr Ser Ser Asn Thr
                100                 105                 110

Ala Tyr Leu Gln Leu Ser Ser Leu Thr Ser Glu Asp Thr Ala Val Tyr
            115                 120                 125

Tyr Cys Ser Asn Tyr Tyr Arg Tyr Asp Asp Thr Met Asp Tyr Trp Gly
        130                 135                 140

Gln Gly Thr Ser Val Thr Val Ser Ser Ala Lys Thr Thr Pro Pro Ser
145                 150                 155                 160

Val Tyr Pro Leu Ala Pro Gly Ser Ala Ala Gln Thr Asn Ser Met Val
                165                 170                 175

Thr Leu Gly Cys Leu Val Lys Gly Tyr Phe
            180                 185

<210> SEQ ID NO 19
<211> LENGTH: 184
<212> TYPE: PRT
<213> ORGANISM: Artificial Sequence

```
<220> FEATURE:
<223> OTHER INFORMATION: Synthetic Sequence - variable region
      (light chain) of anti-S38AA antibody

<400> SEQUENCE: 19

Ala Leu Ser Leu Gln Ser Gly Leu Ser Met Asp Met Arg Ala Pro Ala
1               5                   10                  15

Gln Thr Phe Gly Phe Leu Leu Leu Phe Pro Gly Thr Arg Cys Asp
            20                  25                  30

Ile Gln Met Thr Gln Ser Pro Ser Leu Ser Ala Ser Leu Gly Glu
        35                  40                  45

Arg Val Ser Leu Thr Cys Arg Ala Ser Gln Asp Ile Gly Ser Ser Leu
    50                  55                  60

Asn Trp Leu Gln Gln Glu Pro Asp Gly Thr Ile Lys Arg Leu Ile Tyr
65              70                  75                  80

Asp Thr Ser Thr Leu Asp Ser Gly Val Pro Lys Arg Phe Ser Gly Ser
                85                  90                  95

Arg Ser Gly Ser Asp Tyr Ser Leu Thr Ile Ser Ser Leu Glu Ser Glu
                100                 105                 110

Asp Phe Val Asp Tyr Tyr Cys Leu Gln Tyr Ala Ser Ser Pro Tyr Thr
            115                 120                 125

Phe Gly Gly Gly Thr Lys Leu Glu Ile Lys Arg Ala Asp Ala Ala Pro
        130                 135                 140

Thr Val Ser Ile Phe Pro Pro Ser Ser Glu Gln Leu Thr Ser Gly Gly
145                 150                 155                 160

Ala Ser Val Val Cys Phe Leu Asn Asn Phe Tyr Pro Lys Asp Ile Asn
                165                 170                 175

Val Lys Trp Lys Ile Asp Gly Ser
                180

<210> SEQ ID NO 20
<211> LENGTH: 193
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 20

Asp Arg Arg Thr Thr Leu Asp Ser Gln Val Phe Leu Phe Ser Asp Lys
1               5                   10                  15

His Arg Asn Arg Thr Phe Thr Met Tyr Leu Gly Leu Asn Cys Val Phe
            20                  25                  30

Ile Val Phe Leu Leu Lys Gly Val Gln Ser Glu Val Lys Leu Glu Glu
        35                  40                  45

Ser Gly Gly Gly Leu Val Gln Pro Gly Gly Ser Met Lys Leu Ser Cys
    50                  55                  60

Val Ala Ser Gly Phe Thr Phe Ser Asn Tyr Trp Met Asn Trp Val Arg
65              70                  75                  80

Gln Ser Pro Asp Lys Gly Leu Glu Trp Val Ala Glu Ile Arg Leu Lys
                85                  90                  95

Ser Asn Asn Tyr Ala Thr His Tyr Ala Glu Ser Val Lys Gly Arg Phe
                100                 105                 110

Thr Ile Ser Arg Asp Asp Ser Lys Ser Ser Val Tyr Leu Gln Met Asn
            115                 120                 125

Asn Leu Arg Ala Glu Asp Thr Gly Ile Tyr Tyr Cys Glu Leu Gly Pro
        130                 135                 140
```

-continued

```
Ala Trp Phe Ala Phe Trp Gly Gln Gly Ala Leu Val Thr Val Ser Ala
145                 150                 155                 160

Ala Lys Thr Thr Pro Pro Ser Val Tyr Pro Leu Ala Pro Gly Ser Ala
                165                 170                 175

Ala Gln Thr Asn Ser Met Val Thr Leu Gly Cys Leu Val Lys Gly Tyr
            180                 185                 190

Phe

<210> SEQ ID NO 21
<211> LENGTH: 183
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 21

Asn Gln Phe Leu Pro Gly His Ser Leu Asp Met Arg Phe Gln Val Gln
1               5                   10                  15

Val Leu Gly Leu Leu Leu Leu Trp Ile Ser Gly Ala Gln Cys Asp Val
                20                  25                  30

Gln Ile Thr Gln Ser Pro Ser Tyr Leu Ala Ala Ser Pro Gly Glu Thr
            35                  40                  45

Ile Thr Ile Asn Cys Arg Ala Ser Lys Ser Ile Ser Lys Tyr Leu Ala
    50                  55                  60

Trp Tyr Gln Glu Lys Pro Gly Lys Thr Asn Lys Leu Leu Ile Tyr Ser
65                  70                  75                  80

Gly Ser Thr Leu Lys Ser Gly Ile Pro Ser Arg Phe Ser Gly Ser Gly
                85                  90                  95

Ser Gly Thr Asp Phe Thr Leu Thr Ile Ser Thr Leu Glu Pro Glu Asp
            100                 105                 110

Phe Ala Met Tyr Tyr Cys Gln Gln His Asn Glu Tyr Pro Leu Thr Phe
        115                 120                 125

Gly Ala Gly Thr Lys Leu Glu Leu Lys Arg Ala Asp Ala Ala Pro Thr
    130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser
            180

<210> SEQ ID NO 22
<211> LENGTH: 191
<212> TYPE: PRT
<213> ORGANISM: Artificial Sequence
<220> FEATURE:
<223> OTHER INFORMATION: Synthetic Sequence - variable region
      (heavy chain) of anti-S38AA antibody

<400> SEQUENCE: 22

Val Thr Tyr Gln Gln Gly Ser Asp Gln Leu Val Leu Arg His His Ala
1               5                   10                  15

Gln Val Leu Asp Ile Met Ala Trp Val Trp Thr Leu Leu Phe Leu Met
                20                  25                  30

Ala Ala Ala Gln Ser Ile Gln Ala Gln Ile Gln Leu Val Gln Ser Gly
            35                  40                  45
```

```
Pro Glu Leu Lys Lys Pro Gly Glu Thr Val Lys Ile Ser Cys Lys Ala
        50                  55                  60

Ser Gly Tyr Thr Phe Thr Asp Tyr Ser Met His Trp Val Lys Gln Ala
 65                  70                  75                  80

Pro Gly Lys Gly Leu Lys Trp Met Gly Trp Ile Asn Thr Glu Thr Gly
                 85                  90                  95

Glu Pro Thr Tyr Ala Asp Asp Phe Lys Gly Arg Phe Ala Phe Ser Leu
                100                 105                 110

Glu Thr Ser Ala Ser Thr Ala Tyr Leu Gln Ile Asn Asn Leu Lys Asn
            115                 120                 125

Glu Asp Thr Ala Thr Tyr Phe Cys Ala Arg Tyr Gly Pro Leu Tyr Val
        130                 135                 140

Met Asp Tyr Trp Gly Gln Gly Thr Ser Val Thr Val Ser Ser Ala Lys
145                 150                 155                 160

Thr Thr Pro Pro Ser Val Tyr Pro Leu Ala Pro Gly Cys Gly Asp Thr
                165                 170                 175

Thr Gly Ser Ser Val Thr Leu Gly Cys Leu Val Lys Gly Tyr Phe
            180                 185                 190

<210> SEQ ID NO 23
<211> LENGTH: 187
<212> TYPE: PRT
<213> ORGANISM: Artificial Sequence
<220> FEATURE:
<223> OTHER INFORMATION: Synthetic Sequence - variable region
      (light chain) of anti-S38AA antibody

<400> SEQUENCE: 23

Gln Leu Pro Gly Ala Glu Ala Ser Ser Leu Pro Ala Leu Arg Asp Gly
1               5                  10                  15

Asp Arg His Thr Pro Val Met Gly Thr Ala Ala Leu Gly Ser Arg Phe
            20                  25                  30

His Trp His Cys Ala Asp Thr Val Ser Cys Phe Leu Ser Cys Ile Ser
        35                  40                  45

Gly Ala Glu Gly His His Leu Ile Gln Gly Gln Gln Lys Cys Gln Tyr
 50                  55                  60

Ile Trp Leu Leu Tyr Ala Leu Glu Pro Thr Glu Thr Arg Thr Ala Thr
 65                  70                  75                  80

Gln Thr Pro His Leu Ser Cys Ile Gln Pro Arg Ile Trp Gly Pro Cys
                 85                  90                  95

Gln Val Gln Trp Gln Trp Val Trp Asp Arg Leu His Pro Gln His Pro
                100                 105                 110

Ser Cys Gly Gly Gly Cys Cys Asn Leu Leu Leu Ser Ala His Gly
            115                 120                 125

Ala Tyr Thr Phe Gly Gly Gly Thr Lys Leu Glu Ile Lys Arg Ala Asp
        130                 135                 140

Ala Ala Pro Thr Val Ser Ile Phe Pro Pro Ser Ser Glu Gln Leu Thr
145                 150                 155                 160

Ser Gly Gly Ala Ser Val Val Cys Phe Leu Asn Asn Phe Tyr Pro Lys
                165                 170                 175

Asp Ile Asn Val Lys Trp Lys Ile Asp Gly Ser
            180                 185
```